(12) United States Patent
Mischke

(10) Patent No.: US 9,409,888 B2
(45) Date of Patent: Aug. 9, 2016

(54) DIMERIC COMPOUNDS

(71) Applicant: Hoffmann-La Roche Inc., Nutley, NJ (US)

(72) Inventor: Steven Gregory Mischke, Waltham, MA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/648,282

(22) PCT Filed: Dec. 9, 2013

(86) PCT No.: PCT/EP2013/075874
§ 371 (c)(1),
(2) Date: Sep. 21, 2015

(87) PCT Pub. No.: WO2014/090709
PCT Pub. Date: Jun. 19, 2014

(65) Prior Publication Data
US 2016/0024055 A1   Jan. 28, 2016

Related U.S. Application Data

(60) Provisional application No. 61/735,684, filed on Dec. 11, 2012.

(51) Int. Cl.
| | |
|---|---|
| C07D 403/12 | (2006.01) |
| C07D 401/14 | (2006.01) |
| C07D 403/14 | (2006.01) |
| C07D 243/12 | (2006.01) |
| C07D 243/00 | (2006.01) |

(52) U.S. Cl.
CPC .......... C07D 403/14 (2013.01); C07D 243/00 (2013.01); C07D 243/12 (2013.01); C07D 401/14 (2013.01); C07D 403/12 (2013.01)

(58) Field of Classification Search
CPC .. C07D 403/12; C07D 401/14; C07D 403/14; C07D 243/12
See application file for complete search history.

(56) References Cited

U.S. PATENT DOCUMENTS

2015/0225449 A1* 8/2015 Donnell ................. A61K 38/05
514/19.3

* cited by examiner

Primary Examiner — Bruck Kifle

(57) ABSTRACT

Disclosed are compounds of Formula (I), or pharmaceutically acceptable salts thereof, wherein Z, X, Q and $R^1$ are as described in this application, and methods of using the compounds in the treatment of cancer.

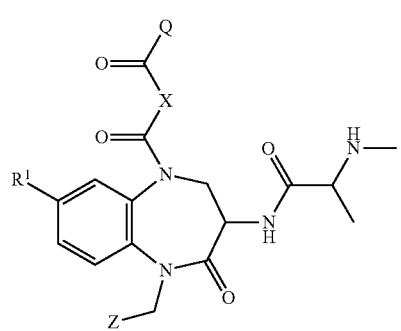

14 Claims, No Drawings

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: TR-FRET peptide

<400> SEQUENCE: 1

Ala Val Pro Ile Ala Gln Lys Ser Glu Lys
1               5                   10

<210> SEQ ID NO 2
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 2

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
            20                  25                  30
```

```
Asp Ile Ser Asp Thr Ile Tyr Pro Arg Asn Pro Ala Met Tyr Ser Glu
             35                  40                  45

Glu Ala Arg Leu Lys Ser Phe Gln Asn Trp Pro Asp Tyr Ala His Leu
 50                  55                  60

Thr Pro Arg Glu Leu Ala Ser Ala Gly Leu Tyr Tyr Thr Gly Ile Gly
 65                  70                  75                  80

Asp Gln Val Gln Cys Phe Ala Cys Gly Gly Lys Leu Lys Asn Trp Glu
             85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
            115                 120                 125

<210> SEQ ID NO 3
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 3

Met Arg His His His His His His Arg Ser Asp Ala Val Ser Ser Asp
 1               5                  10                  15

Arg Asn Phe Pro Asn Ser Thr Asn Leu Pro Arg Asn Pro Ser Met Ala
             20                  25                  30

Asp Tyr Glu Ala Arg Ile Phe Thr Phe Gly Thr Trp Ile Tyr Ser Val
             35                  40                  45

Asn Lys Glu Gln Leu Ala Arg Ala Gly Phe Tyr Ala Leu Gly Glu Gly
 50                  55                  60

Asp Lys Val Lys Cys Phe His Cys Gly Gly Gly Leu Thr Asp Trp Lys
 65                  70                  75                  80

Pro Ser Glu Asp Pro Trp Glu Gln His Ala Lys Trp Tyr Pro Gly Cys
             85                  90                  95

Lys Tyr Leu Leu Glu Gln Lys Gly Gln Glu Tyr Ile Asn Asn Ile His
            100                 105                 110

Leu Thr His Ser Leu Glu Glu Cys Leu Val Arg Thr Thr
            115                 120                 125
```

DIMERIC COMPOUNDS

CROSS-REFERENCE TO RELATED APPLICATIONS

This application is a National Stage Application of PCT/EP2013/075874 filed Dec. 9, 2013, which claims priority from U.S. Provisional Patent Application No. 61/735,684, filed on Dec. 11, 2012. The priority of both said PCT and U.S. Provisional Patent Application are claimed. Each of the prior mentioned applications is hereby incorporated by reference herein in its entirety.

FIELD OF THE INVENTION

The present invention relates to dimeric compounds which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors.

These compounds bind to the BIR2 or BIR2 and BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.1007/82_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPs: From caspase inhibitors to modulators of NF-κB, inflammation and cancer," Nature Review/Cancer, August 2010, Vol 10:561-574.

SUMMARY OF THE INVENTION

One aspect of the present invention is a compound of Formula I

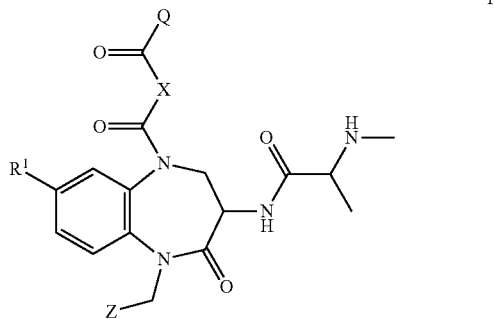

or pharmaceutically acceptable salts thereof, wherein and are as described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

"Alkyl" means a monovalent linear or branched saturated hydrocarbon of 1 to 12 carbon atoms. In particular embodiments, alkyl has 1 to 6 carbon atoms, and in more particular embodiments 1 to 4 carbon atoms ($C_{1-4}$-alkyl). As used herein, "lower alkyl" denotes an alkyl group having from 1-6 carbon atoms ($C_{1-6}$-alkyl). The term "$C_{1-6}$-alkyl" is used alone or in combination with other terms. Examples of alkyl include methyl, ethyl, propyl, isopropyl, butyl (also known as n-butyl), iso-butyl, sec-butyl, tert-butyl, pentyl, hexyl, and the like. The alkyl group can be optionally enriched in deuterium, e.g., —$CD_3$, —$CD_2CD_3$ and the like.

"Aryl" means a monovalent aromatic carbocyclic mono-, bi- or tricyclic ring system comprising 6 to 19 carbon ring atoms. The term "aryl" is used alone or in combination with other terms. Examples of aryl moieties include, but are not limited to, phenyl, naphthyl (also known as naphthalenyl), tolyl, xylyl, pyridinyl, quinolinyl, pyrimidinyl, imidazolyl, thiazolyl, anthracenyl, tetrazolyl, and fluorenyl. Particular aryl groups are phenyl and naphthyl.

"Cyano" means —C≡N.

"Cycloalkyl" means a substituted on unsubstituted stable monovalent saturated monocyclic, bicyclic or tricyclic system which consists of 3 to 10 ring carbon atoms. In particular embodiments, cycloalkyl denotes a monovalent saturated monocyclic hydrocarbon group of 3 to 7 ring carbon atoms ("$C_{3-7}$-cycloalkyl"). The term "$C_{3-7}$-cycloalkyl" is used alone or in combination with other terms. Particular cycloalkyl groups are monocyclic. Examples for monocyclic cycloalkyl are cyclopropyl, cyclobutnyl, cyclopentyl, cyclohexyl or cycloheptyl. Bicyclic means consisting of two saturated carbocycles having one or more carbon atoms in common. Examples of bicyclic cycloalkyl include bicyclo[2.2.1]heptanyl, or bicyclo[2.2.2]octanyl. Tricyclic means consisting of three saturated carbocycles having two or more carbon atoms in common. Examples of tricyclic cycloalkyl include adamantane.

"Fused" when referring to two or more rings, e.g. cycloalkyl fused with aryl, means that the rings have at least two atoms in common. An example of cycloalkyl fused with aryl is tetrahydronaphthalene (also known as tetralin).

"Halogen" or "Halo" means at atom selected from F, Cl, Br or I. In particular embodiments Halogen means F and Cl.

"Heteroatom" means at atom selected from N, O or S.

"Heteroaryl" means a substituted or unsubstituted aromatic heterocyclic ring system containing up to two rings, at least one ring of which includes 1, 2, or 3 heteroatoms, the remaining ring atoms being carbon. Examples of heteroaryl groups include, but are not limited to, thienyl (also known as thiophenyl), furyl (also known as furanyl), indolyl, pyrrolyl, pyridinyl, pyrazinyl, oxazolyl, isoxazolyl, oxadiazolyl, thiazolyl, quinolinyl, isoquinolinyl, indazolyl, pyrimidinyl, imidazolyl, triazolyl, tetrazolyl, triazinyl, pyrazolyl, benzo[d]isoxazolyl, benzothiazolyl, 2-oxo-2H-chromen-4-yl, benzo[d]isoxazolyl, benzothiophenyl, benzoimidazolyl, naphthyridinyl and cinnolinyl. Particular heteroaryl groups are pyrazinyl and pyridinyl.

In the case of a heteroaryl that is bicyclic it should be understood that one ring may be aryl while the other is heteroaryl and both may be independently substituted or unsubstituted.

"$IC_{50}$" refers to the concentration of a particular compound required to inhibit 50% of a specific measured activity. $IC_{50}$ can be measured, inter alia, as is described subsequently in Example 29.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, aryl or heteroaryl means that the substitution (i.e. replacement of one hydrogen atom) can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

In one embodiment, the present invention relates to compounds of Formula I

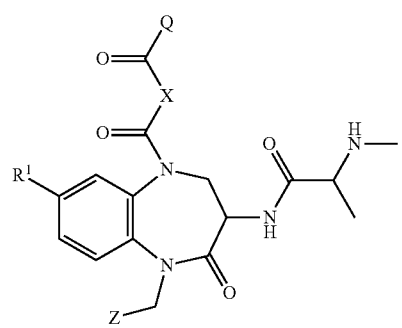

wherein
Z is selected from the group
a) aryl that optionally is substituted with $OR^3$, halogen and lower alkyl, and
b) heteroaryl that optionally is substituted with aryl that optionally is substituted with cyano;
X is selected from the group
a) lower alkyl,
b) lower alkyl-aryl-lower alkyl
c) aryl that optionally is substituted with lower alkyl and —O-aryl, and
d) heteroaryl;
Q is selected from

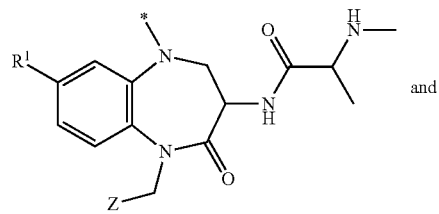

and

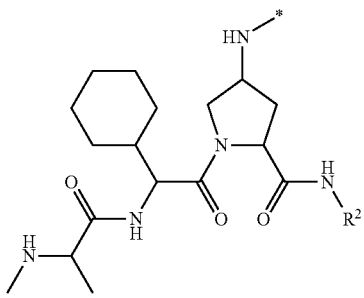

R¹ is selected from the group H and cyano;
R² is selected from the group
a) alkyl that optionally is substituted with aryl,
b) cycloalkyl that optionally is fused with phenyl,
c) phenyl, and
d) cycloalkylaryl; and
R³ is lower alkyl;
or a pharmaceutically acceptable salt thereof.

The asterisk in substituent Q in the above definition denotes the point of attachment of group Q to the rest of the compound of Formula I.

One embodiment of the invention relates to compounds of Formula I wherein
Z is selected from the group
a) aryl that optionally is substituted with O—$C_{1-6}$-alkyl, halogen and $C_{1-6}$-alkyl, and
b) heteroaryl that optionally is substituted with cyanophenyl;
X is selected from the group
a) $C_{1-6}$-alkyl,
b) $C_{1-6}$-alkyl-aryl-$C_{1-6}$-alkyl
c) aryl that optionally is substituted with $C_{1-6}$-alkyl and —O-aryl, and
d) heteroaryl;
Q is selected from

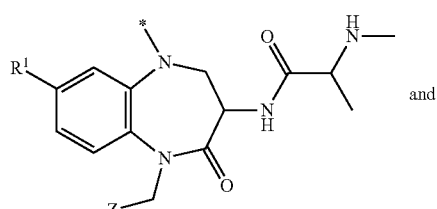

A and

B

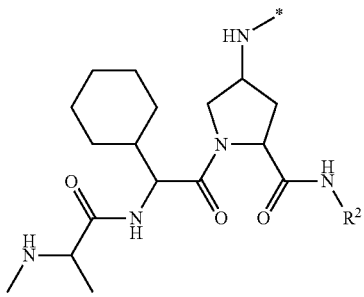

R¹ is selected from the group H and cyano;
R² is selected from the group
a) $C_{1-6}$-alkyl that optionally is substituted with aryl,
b) $C_{3-7}$-cycloalkyl,
c) phenyl, and
d) tetralinyl, and
or a pharmaceutically acceptable salt thereof.

One embodiment of the invention relates to compounds of Formula I wherein Z is aryl that optionally is substituted with O—$C_{1-6}$-alkyl, halogen and $C_{1-6}$-alkyl.

One embodiment of the invention relates to compounds of Formula I wherein Z is naphthyl that optionally is substituted with bromo, methoxy and methyl.

One embodiment of the invention relates to compounds of Formula I wherein Z is 6-bromo-2-methoxy-1-naphthyl.

One embodiment of the invention relates to compounds of Formula I wherein X is $C_{1-6}$-alkyl, heteroaryl, aryl, aryl substituted by $C_{1-6}$-alkyl, $C_{1-6}$-alkyl-phenyl-$C_{1-6}$-alkyl or phenyl-O-phenyl.

One embodiment of the invention relates to compounds of Formula I wherein X is phenyl or naphthyl.

One embodiment of the invention relates to compounds of Formula I wherein X is pyrazinyl or pyridinyl.

One embodiment of the invention relates to compounds of Formula I wherein Q is A.

One embodiment of the invention relates to compounds of Formula I wherein R¹ is H.

One embodiment of the invention relates to compounds of Formula I wherein Z is naphthyl that optionally is substituted with bromo, methoxy and methy, X is $C_{1-6}$-alkyl, heteroaryl, aryl, aryl substituted by $C_{1-6}$-alkyl, $C_{1-6}$-alkyl-phenyl-$C_{1-6}$-alkyl or phenyl-O-phenyl, Q is A and R¹ is H.

One embodiment of the invention relates to compounds of Formula I wherein Q is B.

One embodiment of the invention relates to compounds of Formula I wherein R² is tetralinyl.

One embodiment of the invention relates to a compound of Formula I wherein it is selected from the group consisting of
(2S)-2-(Methylamino)-N-[(3S)-1-[4-[(3S)-3-[[(2S)-2-(methylamino)propanoyl]amino]-5-[(2-methyl-1-naphthyl)methyl]-4-oxo-2,3-dihydro-1,5-benzodiazepine-1-carbonyl]benzoyl]-5-[(2-methyl-1-naphthyl)methyl]-4-oxo-2,3-dihydro-1,5-benzodiazepin-3-yl]propanamide,
(2S)-2-Amino-N-[(3S)-5-[(6-bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-2,5-dimethyl-benzoyl]-4-oxo-2,3-dihydro-1,5-benzodiazepin-3-yl]propanamide,
(2S)-N-[(3S)-1-[(6-Bromo-2-methoxy-1-naphthyl)methyl]-5-[4-[(3S)-1-[(6-bromo-2-methoxy-1-naphthyl)methyl]-7-cyano-3-[[(2S)-2-(methylamino)propanoyl]amino]-2-oxo-3,4-dihydro-1,5-benzodiazepine-5-carbonyl]benzoyl]-7-cyano-2-oxo-3,4-dihydro-1,5-benzodiazepin-3-yl]-2-(methylamino)propanamide,
(2S)-N-[(3S)-5-[(2-Methoxy-1-naphthyl)methyl]-1-[4-[(3S)-5-[(2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide,
(2S)-N-[(3S)-5-[(5-Bromo-2-methoxy-1-naphthyl)methyl]-1-[4-[(3S)-5-[(5-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide,
(2S)-N-[(3S)-5-[(6-Bromo-2-methoxy-1-naphthyl)methyl]-1-[2-[3-[2-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-2-oxo-ethyl]phenyl]acetyl]-4-oxo-2,3-dihydro-1,5-benzodiazepin-3-yl]-2-(methylamino)propanamide,
(2S)-N-[(3S)-5-[(6-Bromo-2-methoxy-1-naphthyl)methyl]-1-[3-[(3S)-5-[(6-bromo-2-methoxy-1-naphthyl)methyl]-

3-[[(2S)-2-(methylamino)propanoyl]amino]-4-oxo-2,3-dihydro-1,5-benzodiazepin-1-yl]-3-oxo-propanoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-4-oxo-butanoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-3-methyl-benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]phenoxy]benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-6-oxo-hexanoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-7-oxo-heptanoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[8-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-8-oxo-octanoyl]-4-oxo-2,3-dihydro-1,5-benzodiazepin-3-yl]-2-(methylamino)propanamide, (2S)-N-[(3S)-5-[[1-(2-Cyanophenyl)indazol-3-yl]methyl]-1-[4-[(3S)-5-[[1-(2-cyanophenyl)indazol-3-yl]methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide, (2S)-N-[(3S)-7-Cyano-5-[4-[(3S)-7-cyano-3-[[(2S)-2-(methylamino)propanoyl]amino]-1-[(2-methyl-1-naphthyl)methyl]-2-oxo-3,4-dihydro-1,5-benzodiazepine-5-carbonyl]benzoyl]-1-[(2-methyl-1-naphthyl)methyl]-2-oxo-3,4-dihydro-1,5-benzodiazepin-3-yl]-2-(methylamino)propanamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1R)-tetralin-1-yl]pyrrolidine-2-carboxamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1S)-tetralin-1-yl]pyrrolidine-2-carboxamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-N-cyclohexyl-1-[(2S)-2-cyclohexyl-2-[[(2S)-2-(methylamino)propanoyl]amino]acetyl]pyrrolidine-2-carboxamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-isopropyl-pyrrolidine-2-carboxamide, and (2S,4S)-N-Benzyl-4-[[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]pyrrolidine-2-carboxamide, or a pharmaceutically acceptable salt thereof.

One embodiment of the invention relates to compounds of Formula I wherein Z is aryl that optionally is substituted with $OR^3$, halogen and $C_{1-6}$-alkyl, or a pharmaceutically acceptable salt of said compound.

One embodiment of the invention relates to compounds of Formula I wherein Z is naphthalenyl.

One embodiment of the invention relates to compounds of Formula I wherein Z is heteroaryl that optionally is substituted with aryl that optionally is substituted by cyano, or a pharmaceutically acceptable salt of said compound.

One embodiment of the invention relates to compounds of Formula I wherein Z is indazolyl that optionally is substituted with cyanophenyl.

One embodiment of the invention relates to compounds of Formula I wherein X is $C_{1-6}$-alkyl, or a pharmaceutically acceptable salt of said compound.

One embodiment of the invention relates to compounds of Formula I wherein X is aryl that optionally is substituted with $C_{1-6}$-alkyl, or a pharmaceutically acceptable salt of said compound.

One embodiment of the invention relates to compounds of Formula I wherein X is phenyl that optionally is substituted with methyl, or a pharmaceutically acceptable salt of said compound.

One embodiment of the invention relates to compounds of Formula I wherein X is naphthalenyl, or a pharmaceutically acceptable salt of said compound.

One embodiment of the invention relates to compounds of Formula I wherein X is heteroaryl, or a pharmaceutically acceptable salt of said compound.

One embodiment of the invention relates to compounds of Formula I wherein X is selected from pyridinyl and pyrazinyl.

One embodiment of the invention relates to compounds of Formula I wherein Q is group A, or a pharmaceutically acceptable salt of said compound.

One embodiment of the invention relates to compounds of Formula I wherein Q is group B, or a pharmaceutically acceptable salt of said compound.

One embodiment of the invention relates to compounds of Formula I wherein $R^1$ is H, or a pharmaceutically acceptable salt of said compound.

One embodiment of the invention relates to compounds of Formula I wherein $R^2$ is lower alkyl that optionally is substituted with phenyl, or a pharmaceutically acceptable salt of said compound.

One embodiment of the invention relates to compounds of Formula I wherein $R^2$ is $C_{3-7}$-cycloalkyl, or a pharmaceutically acceptable salt of said compound.

One embodiment of the invention relates to compounds of Formula I wherein $R^2$ is cyclohexyl.

One embodiment of the invention relates to compounds of Formula I wherein $R^2$ is $C_{3-7}$-cycloalkyl that is fused with phenyl, or a pharmaceutically acceptable salt of said compound.

One embodiment of the invention relates to compounds of Formula I wherein $R^2$ is tetralin.

One embodiment of the invention relates to compounds of Formula I wherein Z is napthalenyl that optionally is substituted with $OCH_3$, halogen, and $C_{1-6}$-alkyl; X is phenyl or naphthalenyl, each of which optionally is substituted with $C_{1-6}$-alkyl; Q is group A; and $R^1$ is H; or a pharmaceutically acceptable salt of said compound.

One embodiment of the invention relates to compounds of Formula I wherein Z is naphtalenyl that is substituted with $OCH_3$ and Br; X is phenyl; Q is group A; and $R^1$ is H; or a pharmaceutically acceptable salt of said compound.

One embodiment of the invention relates to compounds of Formula I wherein Z is naphtalenyl that is substituted with $CH_3$; X is phenyl; Q is group A; and $R^1$ is H; or a pharmaceutically acceptable salt of said compound.

One embodiment of the invention relates to compounds of Formula I wherein Z is naphtalenyl that is substituted with $OCH_3$ and Br; X is phenyl; Q is group A; and $R^1$ is cyano, or a pharmaceutically acceptable salt of said compound.

One embodiment of the invention relates to compounds of Formula I wherein Z is naphtalenyl that optionally is substituted with $OCH_3$ and halogen; X is phenyl; Q is group B; $R^1$ is H; and $R^2$ is selected from $C_{3-7}$-cyclohexyl, $C_{3-7}$-cyclohexyl fused with phenyl, and $C_{1-6}$-alkyl that optionally is substituted with phenyl; or a pharmaceutically acceptable salt of said compound.

One embodiment of the invention relates to compounds of Formula I wherein Z is naphtalenyl that is substituted with $OCH_3$ and Br; X is phenyl, Q is group B; $R^1$ is H; and $R^2$ is selected from $C_{3-7}$-cyclohexyl, $C_{3-7}$-cyclohexyl fused with phenyl, and $C_{1-6}$-alkyl that optionally is substituted with phenyl, or a pharmaceutically acceptable salt of said compound.

One embodiment of the invention relates to compounds of Formula I wherein it is selected from the group consisting of:

(2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-2-carbonyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-3-methyl-benzoyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[4-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]phenoxy]benzoyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide;

(2S)-2-Amino-N-[(3S)-5-[(6-bromo-2-methoxy-1-naphthyl)methyl]-1-[4-[(3S)-5-[(6-bromo-2-methoxy-1-naphthyl)methyl]-3-[[(2S)-2-(methylamino)propanoyl]
amino]-4-oxo-2,3-dihydro-1,5-benzodiazepine-1-
carbonyl]-2,5-dimethyl-benzoyl]-4-oxo-2,3-dihydro-1,5-
benzodiazepin-3-yl]propanamide;
(2S)-N-[(3S)-5-[(6-Bromo-2-methoxy-1-naphthyl)methyl]-
1-[3-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepin-1-yl]-3-oxo-propanoyl]-4-
oxo-2,3-dihydro-1,5-benzodiazepin-3-yl]-2-
(methylamino)propanamide;
(2S)-N-[(3S)-5-[(6-Bromo-2-methoxy-1-naphthyl)methyl]-
1-[4-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepin-1-yl]-4-oxo-butanoyl]-4-oxo-
2,3-dihydro-1,5-benzodiazepin-3-yl]-2-(methylamino)
propanamide;
(2S)-N-[(3S)-5-[(6-Bromo-2-methoxy-1-naphthyl)methyl]-
1-[6-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepin-1-yl]-6-oxo-hexanoyl]-4-
oxo-2,3-dihydro-1,5-benzodiazepin-3-yl]-2-
(methylamino)propanamide;
(2S)-N-[(3S)-5-[(6-Bromo-2-methoxy-1-naphthyl)methyl]-
1-[7-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepin-1-yl]-7-oxo-heptanoyl]-4-
oxo-2,3-dihydro-1,5-benzodiazepin-3-yl]-2-
(methylamino)propanamide;
(2S)-N-[(3S)-5-[(6-Bromo-2-methoxy-1-naphthyl)methyl]-
1-[8-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepin-1-yl]-8-oxo-octanoyl]-4-oxo-
2,3-dihydro-1,5-benzodiazepin-3-yl]-2-(methylamino)
propanamide;
(2S)-N-[(3S)-5-[(6-Bromo-2-methoxy-1-naphthyl)methyl]-
1-[5-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepine-1-carbonyl]pyrazine-2-
carbonyl]-4-oxo-2,3-dihydro-1,5-benzodiazepin-3-yl]-2-
(methylamino)propanamide;
(2S)-N-[(3S)-5-[(6-Bromo-2-methoxy-1-naphthyl)methyl]-
1-[7-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepine-1-carbonyl]naphthalene-2-
carbonyl]-4-oxo-2,3-dihydro-1,5-benzodiazepin-3-yl]-2-
(methylamino)propanamide;
(2S)-N-[(3S)-5-[(6-Bromo-2-methoxy-1-naphthyl)methyl]-
1-[2-[3-[2-[(3S)-5-[(6-bromo-2-methoxy-1-naphthyl)me-
thyl]-3-[[(2S)-2-(methylamino)propanoyl]amino]-4-oxo-
2,3-dihydro-1,5-benzodiazepin-1-yl]-2-oxo-ethyl]
phenyl]acetyl]-4-oxo-2,3-dihydro-1,5-benzodiazepin-3-
yl]-2-(methylamino)propanamide;
(2S-N-[(3S)-5-[(5-Bromo-2-methoxy-1-naphthyl)methyl]-
1-[4-[(3S)-5-[(5-bromo-2-methoxy-1-naphthyl)methyl]-
3-[[(2S)-2-(methylamino)propanoyl]amino]-4-oxo-2,3-
dihydro-1,5-benzodiazepine-1-carbonyl]benzoyl]-4-oxo-
2,3-dihydro-1,5-benzodiazepin-3-yl]-2-(methylamino)
propanamide;
(2S)-2-(Methylamino)-N-[(3S)-1-[4-[(3S)-3-[[(2S)-2-(me-
thylamino)propanoyl]amino]-5-[(2-methyl-1-naphthyl)
methyl]-4-oxo-2,3-dihydro-1,5-benzodiazepine-1-carbo-
nyl]benzoyl]-5-[(2-methyl-1-naphthyl)methyl]-4-oxo-2,
3-dihydro-1,5-benzodiazepin-3-yl]propanamide;
(2S)-N-[(3S)-5-[[1-(2-Cyanophenyl)indazol-3-yl]methyl]-
1-[4-[(3S)-5-[[1-(2-cyanophenyl)indazol-3-yl]methyl]-3-
[[(2S)-2-(methylamino)propanoyl]amino]-4-oxo-2,3-di-
hydro-1,5-benzodiazepine-1-carbonyl]benzoyl]-4-oxo-2,
3-dihydro-1,5-benzodiazepin-3-yl]-2-(methylamino)
propanamide;
(2S)-N-[(3S)-5-[(2-Methoxy-1-naphthyl)methyl]-1-[4-
[(3S)-5-[(2-methoxy-1-naphthyl)methyl]-3-[[(2S)-2-(me-
thylamino)propanoyl]amino]-4-oxo-2,3-dihydro-1,5-ben-
zodiazepine-1-carbonyl]benzoyl]-4-oxo-2,3-dihydro-1,5-
benzodiazepin-3-yl]-2-(methylamino)propanamide;
(2S)-N-[(3S)-7-Cyano-5-[4-[(3S)-7-cyano-3-[[(2S)-2-(me-
thylamino)propanoyl]amino]-1-[(2-methyl-1-naphthyl)
methyl]-2-oxo-3,4-dihydro-1,5-benzodiazepine-5-carbo-
nyl]benzoyl]-1-[(2-methyl-1-naphthyl)methyl]-2-oxo-3,
4-dihydro-1,5-benzodiazepin-3-yl]-2-(methylamino)
propanamide;
(2S)-N-[(3S)-1-[(6-Bromo-2-methoxy-1-naphthyl)methyl]-
5-[4-[(3S)-1-[(6-bromo-2-methoxy-1-naphthyl)methyl]-
7-cyano-3-[[(2S)-2-(methylamino)propanoyl]amino]-2-
oxo-3,4-dihydro-1,5-benzodiazepine-5-carbonyl]
benzoyl]-7-cyano-2-oxo-3,4-dihydro-1,5-benzodiazepin-
3-yl]-2-(methylamino)propanamide; and
(2S)-N-[(3S)-5-[(6-Bromo-2-methoxy-1-naphthyl)methyl]-
1-[4-[(3S)-5-[(6-bromo-2-methoxy-1-naphthyl)methyl]-
3-[[(2S)-2-(methylamino)propanoyl]amino]-4-oxo-2,3-
dihydro-1,5-benzodiazepine-1-carbonyl]benzoyl]-4-oxo-
2,3-dihydro-1,5-benzodiazepin-3-yl]-2-(methylamino)
propanamide;
or a pharmaceutically acceptable salt of any of the forego-
ing compounds.

One embodiment of the invention relates to compounds of Formula I wherein it is selected from the group consisting of:
(2S,4S)-N-Benzyl-4-[[4-[(3S)-5-[(6-bromo-2-methoxy-1-
naphthyl)methyl]-3-[[(2S)-2-(methylamino)propanoyl]
amino]-4-oxo-2,3-dihydro-1,5-benzodiazepine-1-carbo-
nyl]benzoyl]amino]-1-[(2S)-2-cyclohexyl-2-[[(2S)-2-
(methylamino)propanoyl]amino]acetyl]pyrrolidine-2-
carboxamide dihydrochloride;
(2S,4S)-4-[[4-[(3S)-5-[(6-Bromo-2-methoxy-1-naphthyl)
methyl]-3-[[(2S)-2-(methylamino)propanoyl]amino]-4-
oxo-2,3-dihydro-1,5-benzodiazepine-1-carbonyl]ben-
zoyl]amino]-1-[(2S)-2-cyclohexyl-2-[[(2S)-2-
(methylamino)propanoyl]amino]acetyl]-N-[(1R)-tetralin-
1-yl]pyrrolidine-2-carboxamide;
(2S,4S)-4-[[4-[(3S)-5-[(6-Bromo-2-methoxy-1-naphthyl)
methyl]-3-[[(2S)-2-(methylamino)propanoyl]amino]-4-
oxo-2,3-dihydro-1,5-benzodiazepine-1-carbonyl]ben-
zoyl]amino]-1-[(2S)-2-cyclohexyl-2-[[(2S)-2-
(methylamino)propanoyl]amino]acetyl]-N-[(1S)-tetralin-
1-yl]pyrrolidine-2-carboxamide;
(2S,4S)-4-[[4-[(3S)-5-[(6-Bromo-2-methoxy-1-naphthyl)
methyl]-3-[[(2S)-2-(methylamino)propanoyl]amino]-4-
oxo-2,3-dihydro-1,5-benzodiazepine-1-carbonyl]ben-
zoyl]amino]-N-cyclohexyl-1-[(2S)-2-cyclohexyl-2-
[[(2S)-2-(methylamino)propanoyl]amino]acetyl]
pyrrolidine-2-carboxamide; and
(2S,4S)-4-[[4-[(3S)-5-[(6-Bromo-2-methoxy-1-naphthyl)
methyl]-3-[[(2S)-2-(methylamino)propanoyl]amino]-4-
oxo-2,3-dihydro-1,5-benzodiazepine-1-carbonyl]ben-
zoyl]amino]-1-[(2S)-2-cyclohexyl-2-[[(2S)-2-
(methylamino)propanoyl]amino]acetyl]-N-isopropyl-
pyrrolidine-2-carboxamide;
or a pharmaceutically acceptable salt of any of the forego-
ing compounds.

One embodiment of the invention relates to compounds of Formula I wherein it is selected from the group consisting of:
(2S,4S)-N-Benzyl-4-[[4-[(3S)-5-[(6-bromo-2-methoxy-1-
naphthyl)methyl]-3-[[(2S)-2-(methylamino)propanoyl]
amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]pyrrolidine-2-carboxamide dihydrochloride;

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1R)-tetralin-1-yl]pyrrolidine-2-carboxamide;

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1S)-tetralin-1-yl]pyrrolidine-2-carboxamide;

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-N-cyclohexyl-1-[(2S)-2-cyclohexyl-2-[[(2S)-2-(methylamino)propanoyl]amino]acetyl]pyrrolidine-2-carboxamide; and (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-isopropyl-pyrrolidine-2-carboxamide;

or a pharmaceutically acceptable salt of any of the foregoing compounds.

One embodiment of the invention relates to compounds of Formula I wherein it is selected from the group consisting of:

(2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-4-oxo-butanoyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-6-oxo-hexanoyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-7-oxo-heptanoyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[8-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-8-oxo-octanoyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide;

(2S)-N-[(3S)-5-[(6-Bromo-2-methoxy-1-naphthyl)methyl]-1-[2-[3-[2-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-2-oxo-ethyl]phenyl]acetyl]-4-oxo-2,3-dihydro-1,5-benzodiazepin-3-yl]-2-(methylamino)propanamide;

(2S)-N-[(3S)-5-[(5-Bromo-2-methoxy-1-naphthyl)methyl]-1-[4-[(3S)-5-[(5-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide;

(2S)-2-(Methylamino)-N-[(3S)-1-[4-[(3S)-3-[[(2S)-2-(methylamino)propanoyl]amino]-5-[(2-methyl-1-naphthyl)methyl]-4-oxo-2,3-dihydro-1,5-benzodiazepine-1-carbonyl]benzoyl]-5-[(2-methyl-1-naphthyl)methyl]-4-oxo-2,3-dihydro-1,5-benzodiazepin-3-yl]propanamide;

(2S)-N-[(3S)-5-[[1-(2-Cyanophenyl)indazol-3-yl]methyl]-1-[4-[(3S)-5-[[1-(2-cyanophenyl)indazol-3-yl]methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide;

(2S)-N-[(3S)-5-[(2-Methoxy-1-naphthyl)methyl]-1-[4-[(3S)-5-[(2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide;

(2S)-N-[(3S)-7-Cyano-5-[4-[(3S)-7-cyano-3-[[(2S)-2-(methylamino)propanoyl]amino]-1-[(2-methyl-1-naphthyl)methyl]-2-oxo-3,4-dihydro-1,5-benzodiazepine-5-carbonyl]benzoyl]-1-[(2-methyl-1-naphthyl)methyl]-2-oxo-3,4-dihydro-1,5-benzodiazepin-3-yl]-2-(methylamino)propanamide;

(2S)-N-[(3S)-1-[(6-Bromo-2-methoxy-1-naphthyl)methyl]-5-[4-[(3S)-1-[(6-bromo-2-methoxy-1-naphthyl)methyl]-7-cyano-3-[[(2S)-2-(methylamino)propanoyl]amino]-2-oxo-3,4-dihydro-1,5-benzodiazepine-5-carbonyl]benzoyl]-7-cyano-2-oxo-3,4-dihydro-1,5-benzodiazepin-3-yl]-2-(methylamino)propanamide; and (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide;

or a pharmaceutically acceptable salt of any of the foregoing compounds.

One embodiment of the invention relates to a pharmaceutical composition comprising any of the compounds as described herein, or a pharmaceutically acceptable salt thereof, as an active ingredient together with a pharmaceutically acceptable carrier or excipient.

One embodiment of the invention relates to compounds of Formula I as described herein for use as a therapeutically active substance.

One embodiment of the invention relates to compounds of Formula I as described herein for use in the therapeutic and/or prophylactic treatment of cancer.

One embodiment of the invention relates to compounds the use of a compound as described herein, or a pharmaceutically acceptable salt thereof, for the manufacture of a medicament for the therapeutic and/or prophylactic treatment of cancer.

One embodiment of the invention relates to compounds of Formula I wherein Z is aryl that optionally is substituted with $OR^3$, halogen and lower alkyl, or a pharmaceutically acceptable salt of said compound. In a particular embodiment Z is naphthalenyl that optionally is substituted as described immediately above.

Another embodiment of the invention relates to compounds of Formula I wherein Z is heteroaryl that optionally is substituted by aryl that optionally is substituted by cyano, or a pharmaceutically acceptable salt of said compound. In a particular embodiment Z is indazolyl that optionally is substituted with cyanophenyl.

Another embodiment of the invention relates to compounds of Formula I wherein X is lower alkyl, or a pharmaceutically acceptable salt of said compound.

Another embodiment of the invention relates to compounds of Formula I wherein X is aryl that optionally is substituted with lower alkyl, or a pharmaceutically acceptable salt of said compound. In a particular embodiment X is phenyl that optionally is substituted with methyl. In another embodiment X is naphthalenyl.

Another embodiment of the invention relates to compounds of Formula I wherein X is heteroaryl, or a pharmaceutically acceptable salt of said compound. In a particular embodiment X is pyridinyl. In another embodiment X is pyrazinyl.

Another embodiment of the invention relates to compounds of Formula I wherein Q is A, or a pharmaceutically acceptable salt of said compound.

Another embodiment of the invention relates to compounds of Formula I wherein Q is B, or a pharmaceutically acceptable salt of said compound.

Another embodiment of the invention relates to compounds of Formula I wherein $R^1$ is H, or a pharmaceutically acceptable salt of said compound.

Another embodiment of the invention relates to compounds of Formula I wherein $R^2$ is lower alkyl that optionally is substituted with phenyl, or a pharmaceutically acceptable salt of said compound.

Another embodiment of the invention relates to compounds of Formula I wherein $R^2$ is cycloalkyl, or a pharmaceutically acceptable salt of said compound.

In another embodiment $R^2$ is cycloalkyl that is fused with phenyl, or a pharmaceutically acceptable salt of said compound. In a particular embodiment $R^2$ is tetralin.

Another embodiment of the invention relates to compounds of Formula I wherein Z is napthalenyl that optionally is substituted with $OCH_3$, halogen, and lower alkyl; X is phenyl or naphthalenyl, each of which optionally is substituted with lower alkyl; Q is A; and $R^1$ is H; or a pharmaceutically acceptable salt of said compound.

In a particular embodiment of the invention Z is naphtalenyl that is substituted with $OCH_3$ and Br; X is phenyl; Q is A; and $R^1$ is H; or a pharmaceutically acceptable salt of said compound.

In a particular embodiment of the invention Z is naphtalenyl that is substituted with $CH_3$; X is phenyl; Q is A; and $R^1$ is H; or a pharmaceutically acceptable salt of said compound.

In another particular embodiment of the invention, Z is naphtalenyl that is substituted with $OCH_3$ and Br; X is phenyl; Q is group A; and $R^1$ is cyanno; or a pharmaceutically acceptable salt of said compound.

Another embodiment of the invention relates to compounds of Formula I wherein Z is naphtalenyl that optionally is substituted with $OCH_3$ and halogen; X is phenyl; Q is group B; $R^1$ is H; and $R^2$ is selected from cyclohexyl, cyclohexyl fused with phenyl, and lower alkyl that optionally is substituted with phenyl; or a pharmaceutically acceptable salt of said compound.

In a particular embodiment of the invention Z is naphtalenyl that is substituted with $OCH_3$ and Br; X is phenyl; Q is group B; $R^1$ is H; and $R^2$ is selected from cyclohexyl, cyclohexyl fused with phenyl, and lower alkyl that optionally is substituted with phenyl; or a pharmaceutically acceptable salt of said compound.

Compounds according to the invention wherein Q is A, include:

(2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 6);

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-2-carbonyl]-4-oxo-2,3-dihydro-1,5-benzodiazepin-3-yl]-2-(methylamino)propanamide (Example 7);

(2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide (Example 8);

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide (Example 9);

(2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-3-methyl-benzoyl]-4-oxo-2,3-dihydro-1,5-benzodiazepin-3-yl]-2-(methylamino)propanamide (Example 10);

(2S)-N-[(3S)-5-[(6-Bromo-2-methoxy-1-naphthyl)methyl]-1-[4-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]phenoxy]benzoyl]-4-oxo-2,3-dihydro-1,5-benzodiazepin-3-yl]-2-(methylamino)propanamide (Example 11);

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide (Example 12);

(2S)-2-Amino-N-[(3S)-5-[(6-bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-2,5-dimethyl-benzoyl]-4-oxo-2,3-dihydro-1,5-benzodiazepin-3-yl]propanamide (Example 13);

(2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-3-oxo-propanoyl]-4-oxo-2,3-dihydro-1,5-benzodiazepin-3-yl]-2-(methylamino)propanamide (Example 14);

(2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-4-oxo-butanoyl]-4-oxo-2,3-dihydro-1,5-benzodiazepin-3-yl]-2-(methylamino)propanamide (Example 15);

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-6-oxo-hexanoyl]-4-oxo-2,3-dihydro-1,5-benzodiazepin-3-yl]-2-(methylamino)propanamide (Example 16);

(2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-7-oxo-heptanoyl]-4-oxo-2,3-dihydro-1,5-benzodiazepin-3-yl]-2-(methylamino)propanamide (Example 17);

(2S)-N-[(3S)-5-[(6-Bromo-2-methoxy-1-naphthyl)methyl]-1-[8-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-8-oxo-octanoyl]-4-oxo-2,3-dihydro-1,5-benzodiazepin-3-yl]-2-(methylamino)propanamide (Example 18);

(2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]-2-(methylamino)propanamide (Example 19);

(2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide (Example 20);

(2S)-N-[(3S)-5-[(6-Bromo-2-methoxy-1-naphthyl)methyl]-1-[2-[3-[2-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-2-oxo-ethyl]phenyl]acetyl]-4-oxo-2,3-dihydro-1,5-benzodiazepin-3-yl]-2-(methylamino)propanamide (Example 21);

(2S)-N-[(3S)-5-[(5-Bromo-2-methoxy-1-naphthyl)methyl]-1-[4-[(3S)-5-[(5-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 22);

(2S)-2-(Methylamino)-N-[(3S)-1-[4-[(3S)-3-[[(2S)-2-(methylamino)propanoyl]amino]-5-[(2-methyl-1-naphthyl)methyl]-4-oxo-2,3-dihydro-1,5-benzodiazepine-1-carbonyl]benzoyl]-5-[(2-methyl-1-naphthyl)methyl]-4-oxo-2,3-dihydro-1,5-benzodiazepin-3-yl]propanamide (Example 23);

(2S)-N-[(3S)-5-[[1-(2-Cyanophenyl)indazol-3-yl]methyl]-1-[4-[(3S)-5-[[1-(2-cyanophenyl)indazol-3-yl]methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 24);

(2S)-N-[(3S)-5-[(2-Methoxy-1-naphthyl)methyl]-1-[4-[(3S)-5-[(2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 25);

(2S)-N-[(3S)-7-Cyano-5-[4-[(3S)-7-cyano-3-[[(2S)-2-(methylamino)propanoyl]amino]-1-[(2-methyl-1-naphthyl)methyl]-2-oxo-3,4-dihydro-1,5-benzodiazepine-5-carbonyl]benzoyl]-1-[(2-methyl-1-naphthyl)methyl]-2-oxo-3,4-dihydro-1,5-benzodiazepin-3-yl]-2-(methylamino)propanamide (Example 26);

(2S)-N-[(3S)-1-[(6-Bromo-2-methoxy-1-naphthyl)methyl]-5-[4-[(3S)-1-[(6-bromo-2-methoxy-1-naphthyl)methyl]-7-cyano-3-[[(2S)-2-(methylamino)propanoyl]amino]-2-oxo-3,4-dihydro-1,5-benzodiazepine-5-carbonyl]benzoyl]-7-cyano-2-oxo-3,4-dihydro-1,5-benzodiazepin-3-yl]-2-(methylamino)propanamide (Example 27); and (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 28);

or a pharmaceutically acceptable salt of any of the foregoing compounds.

Compounds according to the invention wherein Q is B, include:

(2S,4S)-N-Benzyl-4-[[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]pyrrolidine-2-carboxamide dihydrochloride (Example 1);

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1R)-tetralin-1-yl]pyrrolidine-2-carboxamide (Example 2);

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1S)-tetralin-1-yl]pyrrolidine-2-carboxamide (Example 3);

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-N-cyclohexyl-1-[(2S)-2-cyclohexyl-2-[[(2S)-2-(methylamino)propanoyl]amino]acetyl]pyrrolidine-2-carboxamide (Example 4); and (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-isopropyl-pyrrolidine-2-carboxamide (Example 5);

or a pharmaceutically acceptable salt of any of the foregoing compounds.

Another embodiment of the invention relates to a compound selected from:

(2S,4S)-N-Benzyl-4-[[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]pyrrolidine-2-carboxamide dihydrochloride (Example 1);

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1R)-tetralin-1-yl]pyrrolidine-2-carboxamide (Example 2);

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-

(methylamino)propanoyl]amino]acetyl]-N-[(1S)-tetralin-1-yl]pyrrolidine-2-carboxamide (Example 3);

(2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-N-cyclohexyl-1-[(2S)-2-cyclohexyl-2-[[(2S)-2-(methylamino)propanoyl]amino]acetyl]pyrrolidine-2-carboxamide (Example 4); and (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-isopropyl-pyrrolidine-2-carboxamide (Example 5);

(2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-4-oxo-butanoyl]-4-oxo-2,3-dihydro-1,5-benzodiazepin-3-yl]-2-(methylamino)propanamide (Example 15);

(2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-6-oxo-hexanoyl]-4-oxo-2,3-dihydro-1,5-benzodiazepin-3-yl]-2-(methylamino)propanamide (Example 16);

(2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-7-oxo-heptanoyl]-4-oxo-2,3-dihydro-1,5-benzodiazepin-3-yl]-2-(methylamino)propanamide (Example 17);

(2S)-N-[(3S)-5-[(6-Bromo-2-methoxy-1-naphthyl)methyl]-1-[8-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-8-oxo-octanoyl]-4-oxo-2,3-dihydro-1,5-benzodiazepin-3-yl]-2-(methylamino)propanamide (Example 18);

(2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]-2-(methylamino)propanamide (Example 19);

(2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide (Example 20);

(2S)-N-[(3S)-5-[(6-Bromo-2-methoxy-1-naphthyl)methyl]-1-[2-[3-[2-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-2-oxo-ethyl]phenyl]acetyl]-4-oxo-2,3-dihydro-1,5-benzodiazepin-3-yl]-2-(methylamino)propanamide (Example 21);

(2S)-N-[(3S)-5-[(5-Bromo-2-methoxy-1-naphthyl)methyl]-1-[4-[(3S)-5-[(5-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 22);

(2S)-2-(Methylamino)-N-[(3S)-1-[4-[(3S)-3-[[(2S)-2-(methylamino)propanoyl]amino]-5-[(2-methyl-1-naphthyl)methyl]-4-oxo-2,3-dihydro-1,5-benzodiazepine-1-carbonyl]benzoyl]-5-[(2-methyl-1-naphthyl)methyl]-4-oxo-2,3-dihydro-1,5-benzodiazepin-3-yl]propanamide (Example 23);

(2S)-N-[(3S)-5-[[1-(2-Cyanophenyl)indazol-3-yl]methyl]-1-[4-[(3S)-5-[[1-(2-cyanophenyl)indazol-3-yl]methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 24);

(2S)-N-[(3S)-5-[(2-Methoxy-1-naphthyl)methyl]-1-[4-[(3S)-5-[(2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 25);

(2S)-N-[(3S)-7-Cyano-5-[4-[(3S)-7-cyano-3-[[(2S)-2-(methylamino)propanoyl]amino]-1-[(2-methyl-1-naphthyl)methyl]-2-oxo-3,4-dihydro-1,5-benzodiazepine-5-carbonyl]benzoyl]-1-[(2-methyl-1-naphthyl)methyl]-2-oxo-3,4-dihydro-1,5-benzodiazepin-3-yl]-2-(methylamino)propanamide (Example 26);

(2S)-N-[(3S)-1-[(6-Bromo-2-methoxy-1-naphthyl)methyl]-5-[4-[(3S)-1-[(6-bromo-2-methoxy-1-naphthyl)methyl]-7-cyano-3-[[(2S)-2-(methylamino)propanoyl]amino]-2-oxo-3,4-dihydro-1,5-benzodiazepine-5-carbonyl]benzoyl]-7-cyano-2-oxo-3,4-dihydro-1,5-benzodiazepin-3-yl]-2-(methylamino)propanamide (Example 27); and (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide (Example 28);

or a pharmaceutically acceptable salt of any of the foregoing compounds.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by Formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of Formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a Formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, $H_2O$, polyols, saccharose, invert sugar, glucose, etc. Suitable adjuvants for injection solutions are, for example, $H_2O$, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in the schemes below.

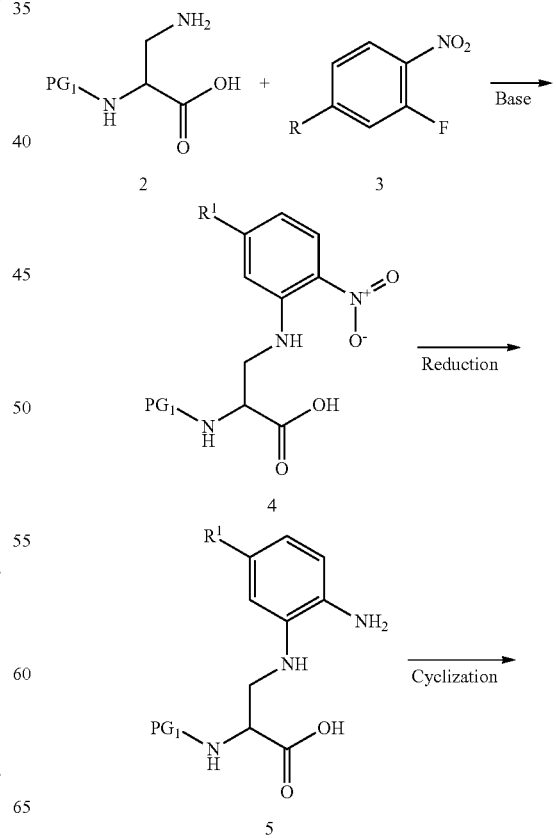

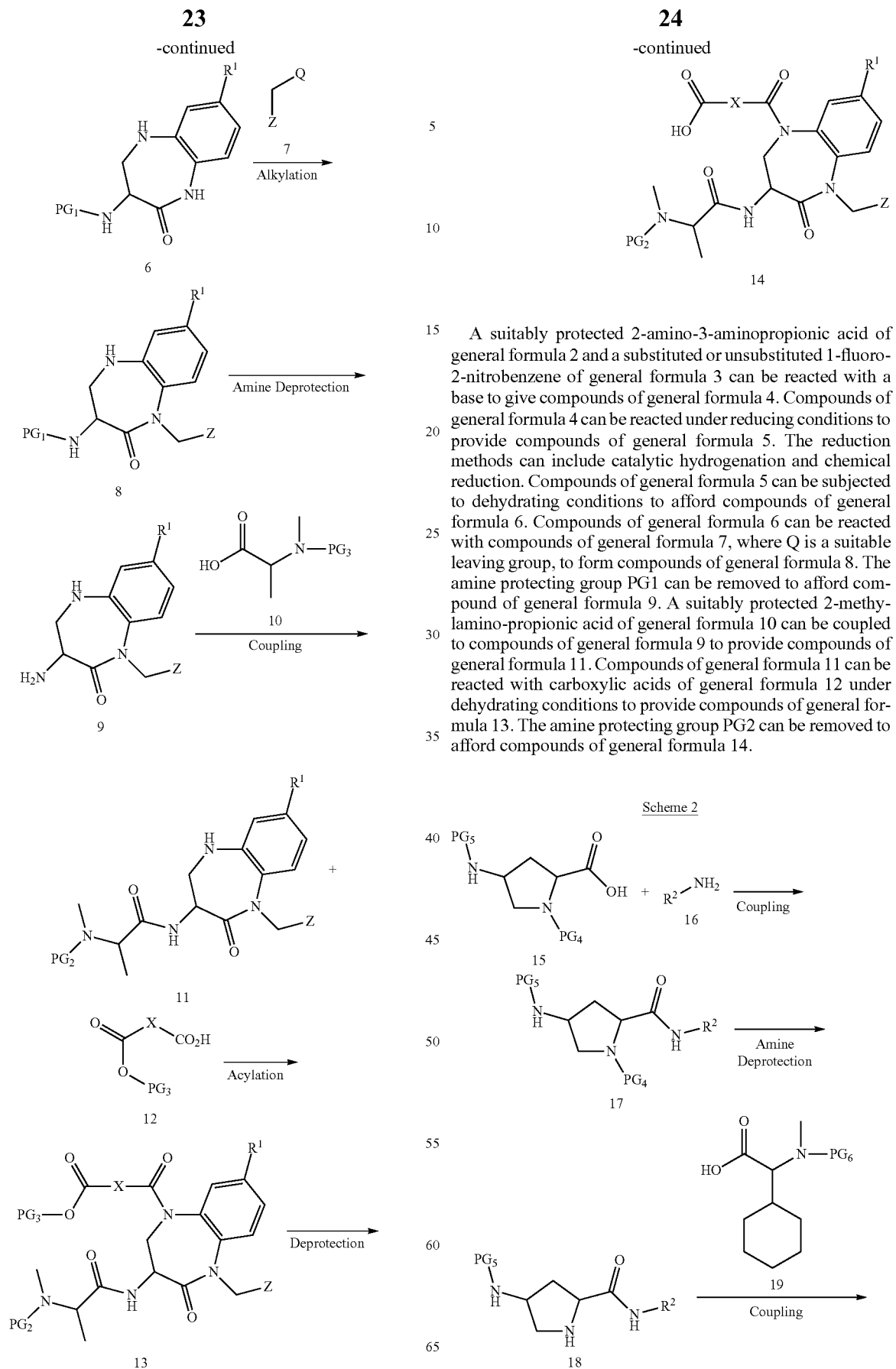

A suitably protected 2-amino-3-aminopropionic acid of general formula 2 and a substituted or unsubstituted 1-fluoro-2-nitrobenzene of general formula 3 can be reacted with a base to give compounds of general formula 4. Compounds of general formula 4 can be reacted under reducing conditions to provide compounds of general formula 5. The reduction methods can include catalytic hydrogenation and chemical reduction. Compounds of general formula 5 can be subjected to dehydrating conditions to afford compounds of general formula 6. Compounds of general formula 6 can be reacted with compounds of general formula 7, where Q is a suitable leaving group, to form compounds of general formula 8. The amine protecting group PG1 can be removed to afford compound of general formula 9. A suitably protected 2-methylamino-propionic acid of general formula 10 can be coupled to compounds of general formula 9 to provide compounds of general formula 11. Compounds of general formula 11 can be reacted with carboxylic acids of general formula 12 under dehydrating conditions to provide compounds of general formula 13. The amine protecting group PG2 can be removed to afford compounds of general formula 14.

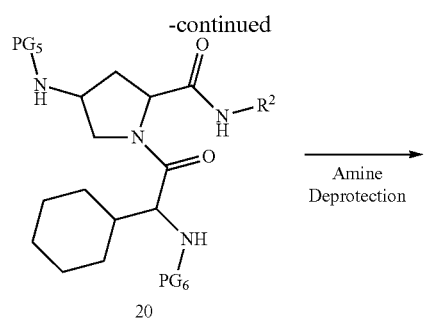
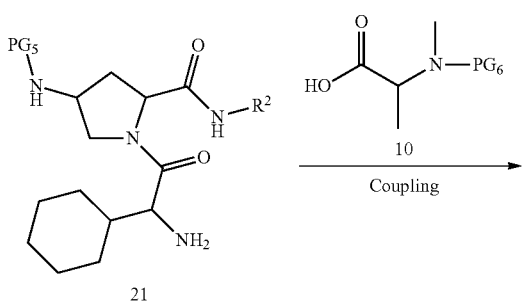
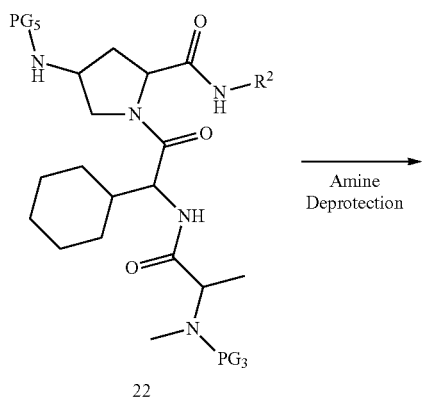
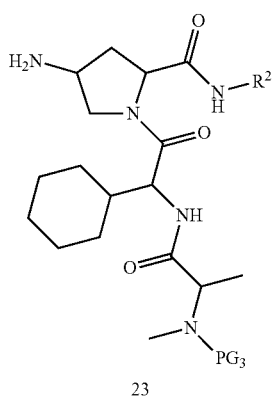

eral formula 17. The protecting group PG4 of compounds of general formula 17 can be removed to afford compounds of general formula 18. A suitably protected α-(methylamino)-cyclohexaneacetic acid of general formula 19 can be coupled to compounds of general formula 18 to provide compounds of general formula 20. The protecting group PG6 in compounds of general formula 20 can be removed to give compounds of general formula 21. Compounds of general formula 21 can be coupled with a suitably protected 2-methylamino-propionic acid of general formula 10 to provide compounds of general formula 22. The protecting group PG5 in compounds of general formula 22 can be removed to yield compounds of general formula 23.

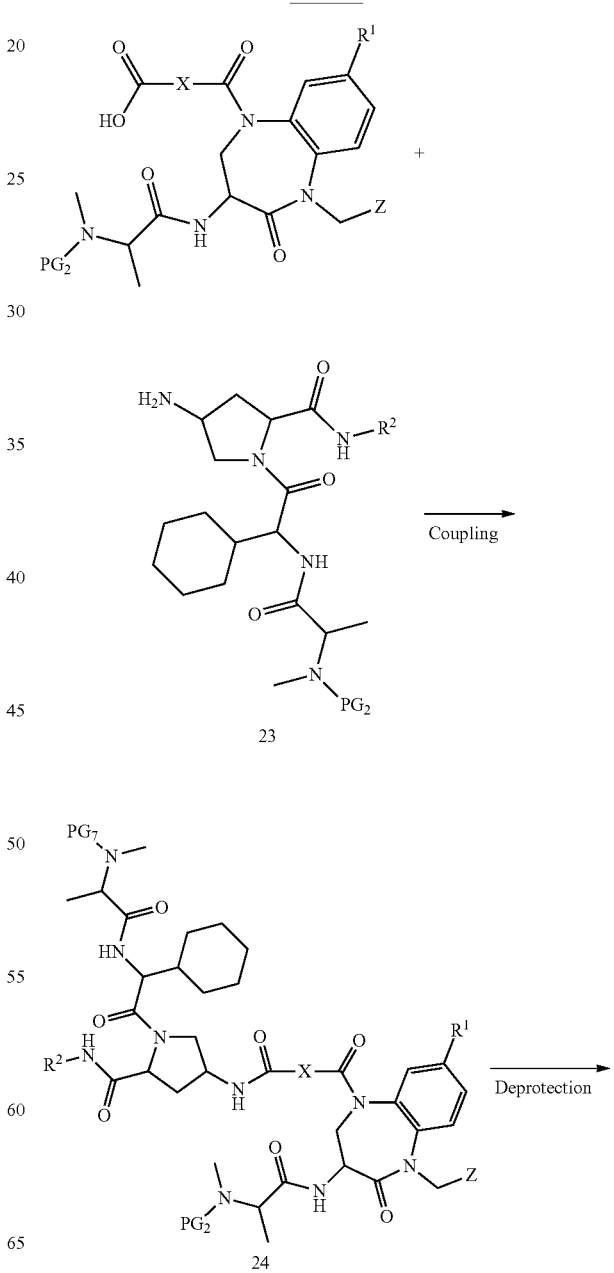

Scheme 3

A suitably protected 4-amino-pyrrolidine-2-carboxylic acid of general formula 15, where the protecting groups PG4 and PG5 are selected so that each can be removed independently, can be reacted with an amine of general formula 16 under dehydrating conditions to provide compounds of gen-

27

-continued

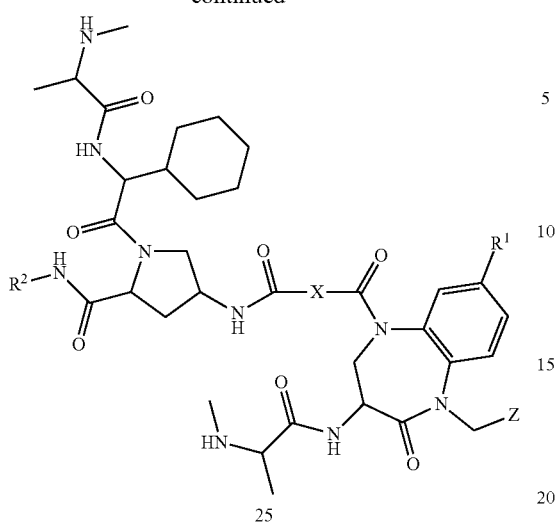

25

Compounds of general formula 14 can be coupled with compounds of general formula 23 under dehydrating conditions to afford compounds of general formula 24. The protecting groups PG2 and PG7 can be removed to afford compounds of general formula 25.

Sheme 4

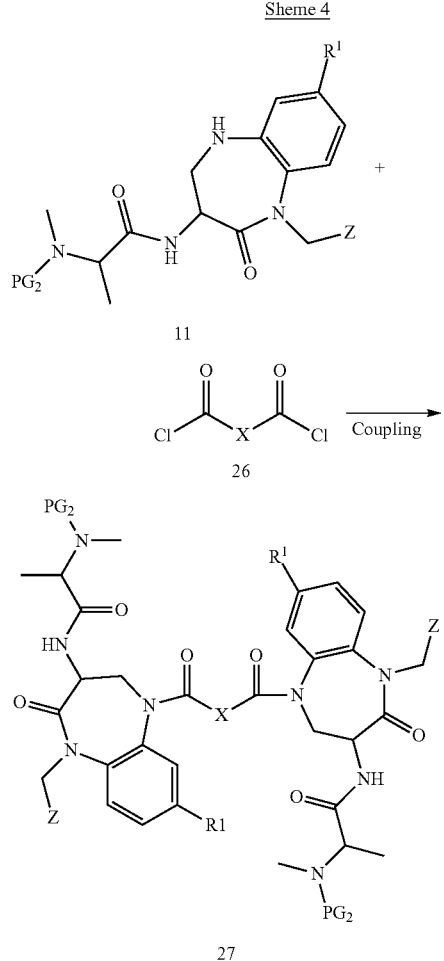

28

-continued

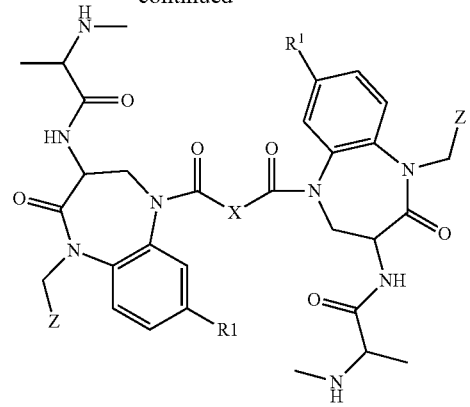

28

Compounds of general formula 11 can be treated with dicarbonyl chlorides of general formula 26 to afford compounds of general formula 27. The protecting groups PG2 can be removed from compounds of general formula 27 to provide compounds of general formula 28.

Scheme 5

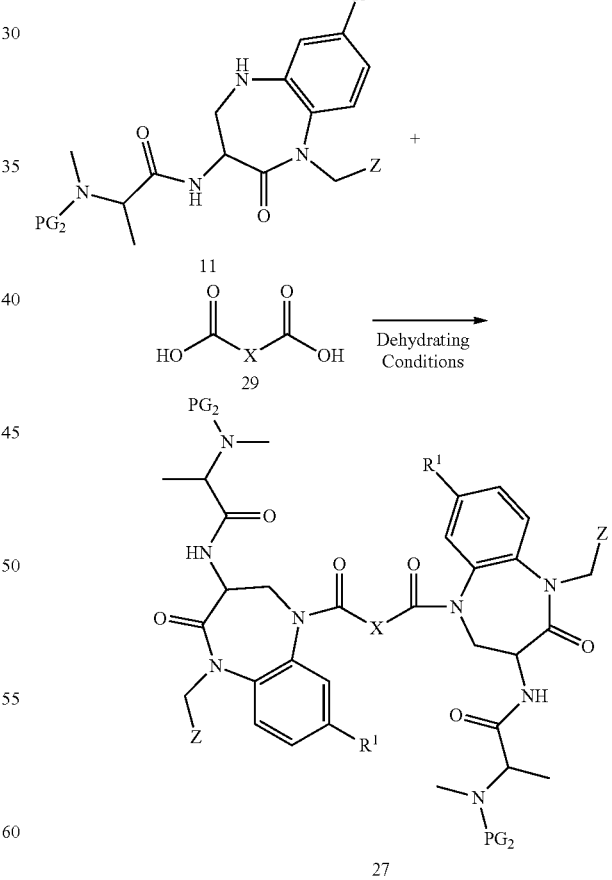

In cases where a suitable dicarbonyl chloride is not commercially available or known in the literature, compounds of general formula 27 can be prepared by treating compounds of general structure 11 and dicarboxylic acids of general formula 29 under dehydrating condition. Such conditions include, but are not limited to, reactions with POCl$_3$, SOCl$_2$ or other dehydrating reagents that would be known to those skilled in the art.

Those skilled in the art will recognize there may be alternate synthetic paths to provide intermediates described above. For example, an alternate route to compounds of general formula 22 is described in Scheme 6.

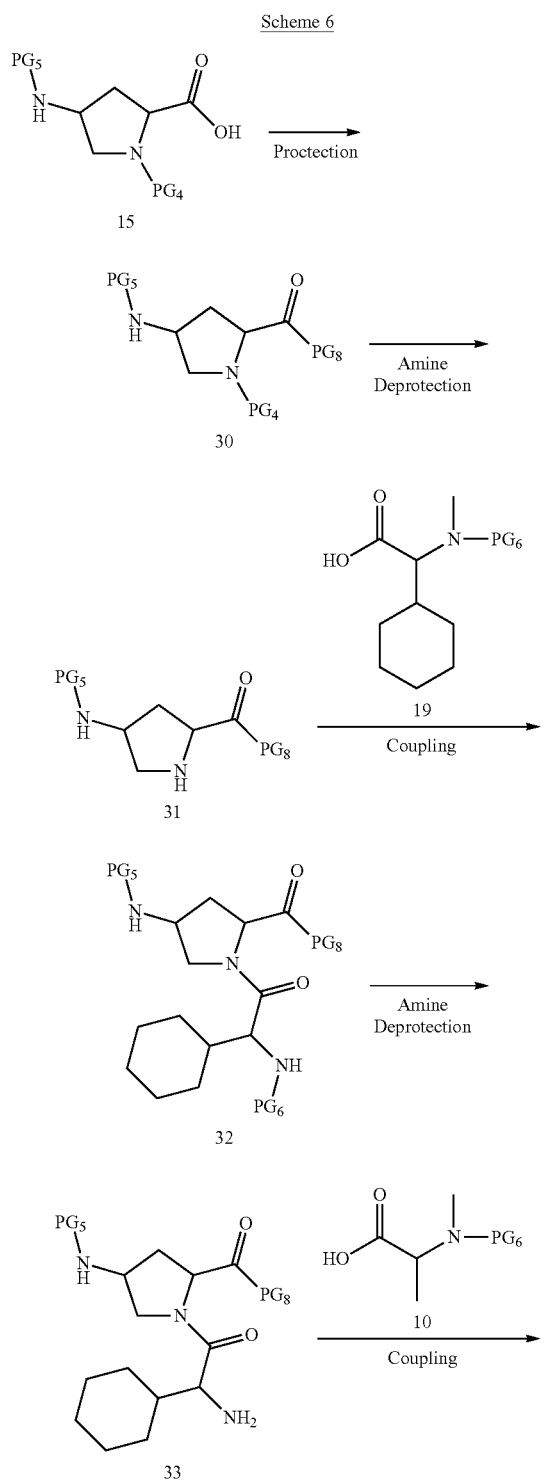

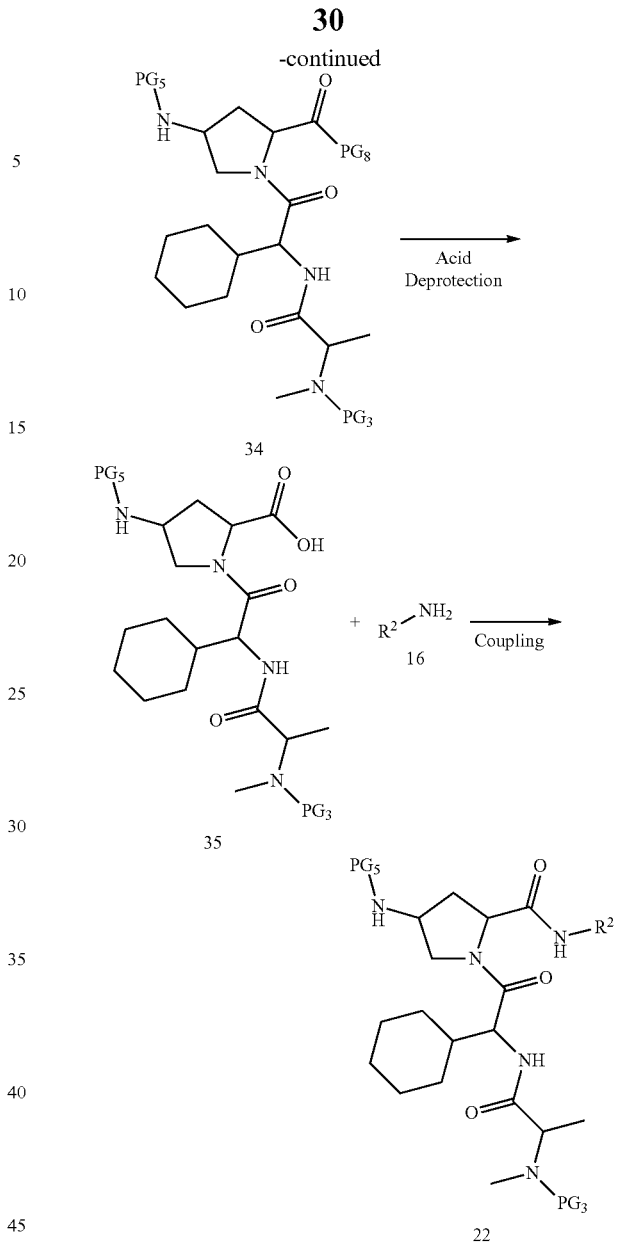

The carboxylic acid in compounds of general structure 15 can be protected with a protecting group, PG8, to provide compounds of general formula 30 where PG8 is a group that renders the carboxylic acid inert to reaction conditions used in the rest of the synthetic sequence. Preferred choices for protecting group PG8 may be made by reference to organic chemistry text books (e.g. Protective Groups in Organic Synthesis, Theodora W. Greene et al.), the original chemistry literature, or would be generally known to one knowledgeable in the art of organic synthesis. The protecting group PG4 of compounds of general formula 30 can be removed to afford compounds of general formula 31. A suitably protected α-(methylamino)-cyclohexaneacetic acid of general formula 19 can be coupled to compounds of general formula 31 to provide compounds of general formula 32. The protecting group PG6 in compounds of general formula 32 can be removed to give compounds of general formula 33. Compounds of general formula 33 can be coupled with a suitably protected 2-methylamino-propionic acid of general structure 10 to provide compounds of general formula 34. The carboxylic acid protecting group PG8 in compounds of general formula 34 can be removed to yield compounds of general formula 35. Compounds of general formula 35 can be reacted with an amine of general structure 16 under dehydrating conditions to provide compounds of general structure 22.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

Examples

The compounds of the present invention may be synthesized according to known techniques. The following examples and references are provided to aid the understanding of the present invention. The examples are not intended, however, to limit the invention, the true scope of which is set forth in the appended claims. The names of the reactants and final products in the examples were generated using AutoNom 2000 Add-in v4.0 SP2 (function in ISIS Draw, Elsevier/MDL), or AutoNom 2000 TT v4.01.305 (Elsevier/MDL), or functions available in ChemDraw Pro Control 11.0.2 (CambridgeSoft Corp.), or Struct=Name feature of electronic notebooks, or Accelrys Draw 4.0.

EXAMPLES

Preparation of Intermediates

Intermediate 1

2-(3-(Bromomethyl)-1H-indazol-1-yl)benzonitrile

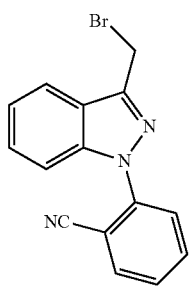 [SMILES: N#Cc1ccccc1-n1nc(CBr)c2ccccc21]

Step 1: $Cs_2CO_3$ (1.56 g, 4.8 mmol) was added to a solution of 3-methyl indazole (0.634 g, 4.8 mmol) and 2-fluorobenzonitrile (1 mL, 9.6 mmol) in DMF (20 mL). After 12 h the mixture was diluted with sat. $NH_4Cl$ and a precipitate formed. The solid was filtered, washed with $H_2O$, hexane and dried under vacuum to give 2-(3-methyl-1H-indazol-1-yl)benzonitrile (1 g, 89%) which was used without purification.

Step 2: AIBN (141 mg, 0.857 mmol) and NBS (839 mg, 4.72 mmol) were added to a suspension of 2-(3-methyl-1H-indazol-1-yl)benzonitrile (1 g, 4.29 mmol) in $CCl_4$ (20 mL) and the mixture heated to reflux for 2 h. The mixture was concentrated and the residue purified by silica gel chromatography to give the title compound (1.25 g, 93%) as an off white solid.

Intermediate 2

((S)-2-Oxo-2,3,4,5-tetrahydro-1H-benzo[b][1,4]diazepin-3-yl)-carbamic acid tert-butyl ester

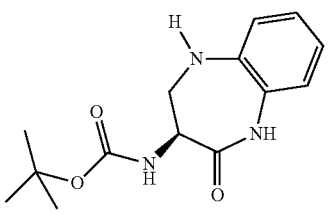 [SMILES: CC(C)(C)OC(=O)N[C@H]1CNc2ccccc2NC1=O]

Step 1: To a solution of (S)-3-amino-2-tert-butoxycarbonylamino-propionic acid (Aldrich) (5 g, 24.48 mmol) in DMF (75 mL) was added 1-fluoro-2-nitro-benzene (2.92 mL, 26.93 mmol) and sodium bicarbonate (6.17 g, 73.44 mmol) at RT and the resulting mixture was heated at 80° C. for 18 h under nitrogen atmosphere. Water was added and the aqueous layer was washed with ethyl acetate. The pH of the aqueous solution was adjusted to 3 with the addition of 10% aqueous sodium bisulfate solution and extracted with ethyl acetate. The combined organic extracts were washed with brine, dried ($Na_2SO_4$) and concentrated under reduced pressure to give crude mass which was triturated with hexanes to afford (S)-2-tert-butoxycarbonylamino-3-(2-nitro-phenylamino)-propionic acid (5 g, 63%) as an orange yellow solid. LC-MS: 326.2 (M+H).

Step 2: A solution of (S)-2-tert-butoxycarbonylamino-3-(2-nitro-phenylamino)-propionic acid (Aldrich) (10 g, 30.76 mmol) in MeOH (100 mL) was purged with argon for 30 min, and 10% Pd—C (1 g) was added to the solution. The resulting mixture was hydrogenated using a balloon for 18 h at RT. The mixture was filtered through Celite and the filtrate was concentrated and the resulting material was triturated with hexane to afford (S)-3-(2-amino-phenylamino)-2-tert-butoxycarbonylamino-propionic acid (8.5 g, 93%) as brown solid. LC-MS: 296 (M+H).

Step 3: To an ice cold solution of (S)-3-(2-amino-phenylamino)-2-tert-butoxycarbonylamino-propionic acid (4 g, 13.54 mmol) in DMF (40 mL) was added EDCI.HCl (2.86 g, 14.89 mmol), HOBT (2.01 g, 14.89 mmol) and DIPEA (7.19 mL, 40.63 mmol). The resulting mixture was stirred for 16 h at RT. The mixture was diluted with ethyl acetate and washed with water and brine. The organic layer was concentrated and the resulting material was purified by silica gel chromatography using to afford the title compound (2.9 g, 77%) as an off white solid. LC-MS: 278 (M+H).

Intermediate 3

((S)-7-Cyano-2-oxo-2,3,4,5-tetrahydro-1H-benzo[b][1,4]diazepin-3-yl)-carbamic acid tert-butyl ester

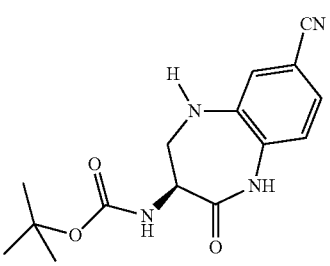 [SMILES: CC(C)(C)OC(=O)N[C@H]1CNc2cc(C#N)ccc2NC1=O]

Step 1: To a solution of (S)-3-amino-2-tert-butoxycarbonylamino-propionic acid (Aldrich) (3 g, 14.706 mmol) in DMF (60 mL) was added cesium carbonate (14.34 g, 44.118 mmol) and 3-fluoro-4-nitro-benzonitrile (2.685 mL, 16.176 mmol) at RT and the resulting mixture was stirred for 3 h at RT under nitrogen atmosphere. The reaction mixture was diluted with ethyl acetate, washed with ice cold water, brine, dried and concentrated to give a material which was purified by silica gel chromatography to provide (S)-2-tert-butoxycarbonyl amino-3-(5-cyano-2-nitro-phenylamino)-propionic acid (4.4 g, 85.4%) as an orange yellow solid. LC-MS: 350.8 (M+H).

Step 2: A solution of (S)-2-tert-butoxycarbonylamino-3-(5-cyano-2-nitro-phenylamino)-propionic acid (4.4 g, 12.57 mmol) in ethyl acetate (70 mL) was purged with argon for 15 min and 10% Pd—C (1 g) was added. The resulting mixture was hydrogenated under a balloon for 16 h at RT. The mixture was filtered through Celite and the filtrate was concentrated to give a material which was triturated with hexane to afford (S)-3-(2-amino-5-cyano-phenylamino)-2-tert-butoxycarbonyl amino-propionic acid (4.16 g, 94.69%) as a brown solid. LC-MS: 321.0 (M+H).

Step 3: To an ice cold solution of (S)-3-(2-amino-5-cyano-phenylamino)-2-tert-butoxycarbonyl amino-propionic acid (4.1 g, 12.812 mmol) in DMF (40 mL) was added EDCI.HCl (2.89 g, 15.125 mmol), HOBT (2.05 g, 15.125 mmol) and DIPEA (7.1 mL, 41.25 mmol). The resulting mixture was stirred for 16 h at RT and mixture was diluted with ethyl acetate and washed with water, brine and the organic solution was concentrated to give a material which was purified by silica gel chromatography to afford the title compound (1.4 g, 36.26%) as a light pink solid. LC-MS: 303.2 (M+H).

Intermediate 4

[(S)-1-(6-Bromo-2-methoxy-naphthalen-1-ylmethyl)-2-oxo-2,3,4,5-tetrahydro-1H-benzo[b][1,4]diazepin-3-yl]-carbamic acid tert-butyl ester

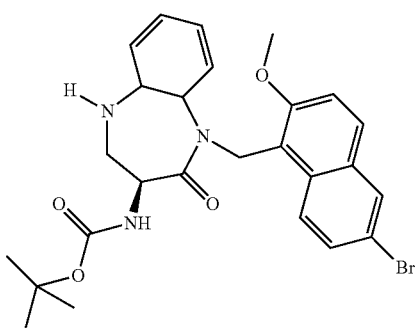 [SMILES: COc1ccc2cc(Br)ccc2c1CN1C(=O)[C@@H](NC(=O)OC(C)(C)C)CNC2C=CC=CC21]

To a solution of ((S)-2-oxo-2,3,4,5-tetrahydro-1H-benzo[b][1,4]diazepin-3-yl)-carbamic acid tert-butyl ester (Intermediate 2) (6.5 g, 23.48 mmol) in THF (100 mL) at −78° C. was added 1 M LiHMDS (4.7 g, 28 mL, 28 mmol). The cooling bath was removed and the mixture stirred at RT for 1 h. The mixture was cooled to −78° C. and a mixture of 6-bromo-1-chloromethyl-2-methoxy-naphthalene (8.0 g, 28.12 mmol) and NaI (4.2 g, 28.12 mmol) in dry THF (30 mL) was added dropwise. The cooling bath was removed and the mixture stirred at RT for 18 h. The mixture was diluted with saturated NH₄Cl, extracted with ethyl acetate and the organic layer washed with water, brine, dried (Na₂SO₄) and concentrated to give a material which was purified by silica gel chromatography to afford the title compound (9 g, 72%) as a yellow solid. LC-MS: 528.0 (M+H).

Intermediate 5

[(S)-1-(5-Bromo-2-methoxy-naphthalen-1-ylmethyl)-2-oxo-2,3,4,5-tetrahydro-1H-benzo[b][1,4]diazepin-3-yl]-carbamic acid tert-butyl ester

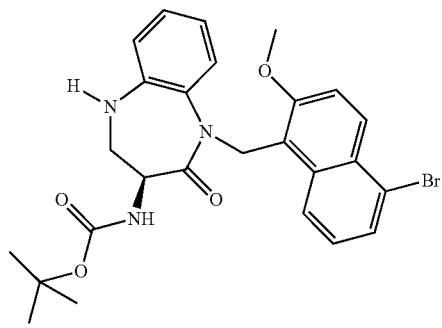 [SMILES: COc1ccc2c(Br)cccc2c1CN1C(=O)[C@@H](NC(=O)OC(C)(C)C)CNc2ccccc21]

To a stirred solution of ((S)-2-oxo-2,3,4,5-tetrahydro-1H-benzo[b][1,4]diazepin-3-yl)-carbamic acid tert-butyl ester (Intermediate 2) (500 mg, 1.805 mmol) in THF (10 mL) at −78° C. was added LiHMDS (1 M in THF, 2.3 mL, 2.3 mmol) dropwise over 5 min. The mixture was stirred at −78° C. for 20 min. and a mixture of sodium iodide (295.8 mg, 1.986 mmol) and 5-bromo-1-chloromethyl-2-methoxy-naphthalene (617.3 mg, 2.166 mmol) in THF (5 mL), was added dropwise over 5 min. The mixture was stirred at −78° C. for 50 min. and the cooling bath was removed. After 16 h, aqueous citric acid was added and the mixture extracted with ethyl acetate. The extract was washed with saturated sodium carbonate solution, dried and concentrated to give a material which was purified by silica gel chromatography to provide the title compound (780 mg, 82%) as a white solid. LC-MS: 528 (M+H).

Intermediate 6

[(S)-1-(2-Methoxy-naphthalen-1-ylmethyl)-2-oxo-2,3,4,5-tetrahydro-1H-benzo[b][1,4]diazepin-3-yl]-carbamic acid tert-butyl ester

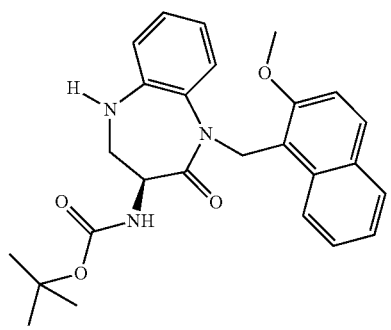 [SMILES: COc1ccc2ccccc2c1CN1C(=O)[C@@H](NC(=O)OC(C)(C)C)CNc2ccccc21]

In a similar manner to that described for the preparation of [(S)-1-(5-bromo-2-methoxy-naphthalen-1-ylmethyl)-2-oxo-2,3,4,5-tetrahydro-1H-benzo[b][1,4]diazepin-3-yl]-carbamic acid tert-butyl ester (Intermediate 5), ((S)-2-oxo-2,3,4,5-tetrahydro-1H-benzo[b][1,4]diazepin-3-yl)-carbamic acid tert-butyl ester (Intermediate 4)(400 mg, 1.44 mmol) and 1-bromomethyl-2-methoxy-naphthalene (435.15 mg, 1.733 mmol) were converted to the title compound (450 mg, 69.6%) which was obtained as a white solid. LC-MS 448 (M+H).

Intermediate 7

{(S)-1-[1-(2-Cyano-phenyl)-1H-indazol-3-ylmethyl]-2-oxo-2,3,4,5-tetrahydro-1H-benzo[b][1,4]diazepin-3-yl}-carbamic acid tert-butyl ester

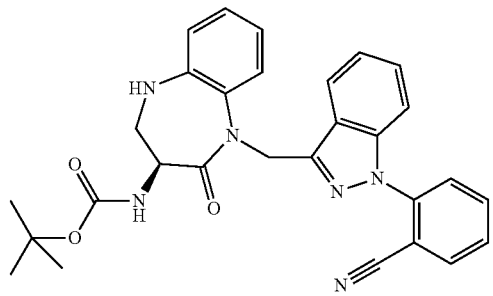 [SMILES: CC(C)(C)OC(=O)N[C@H]1CNc2ccccc2N(Cc2nn(-c3ccccc3C#N)c3ccccc23)C1=O]

In a similar manner to that described for the preparation of [(S)-1-(5-bromo-2-methoxy-naphthalen-1-ylmethyl)-2-oxo-2,3,4,5-tetrahydro-1H-benzo[b][1,4]diazepin-3-yl]-carbamic acid tert-butyl ester (Intermediate 5), ((S)-2-oxo-2,3,4,5-tetrahydro-1H-benzo[b][1,4]diazepin-3-yl)-carbamic acid tert-butyl ester (Intermediate 2)(500 mg, 1.8 mmol) and 2-(3-bromomethyl-indazol-1-yl)-benzonitrile (Intermediate 1) (676.18 mg, 2.16 mmol) were converted to the title compound (670 mg, 72.9%) which was obtained as light yellow solid. LC-MS: 509 (M+H).

Intermediate 8

[(S)-1-(2-Methyl-naphthalen-1-ylmethyl)-2-oxo-2,3,4,5-tetrahydro-1H-benzo[b][1,4]diazepin-3-yl]-carbamic acid tert-butyl ester

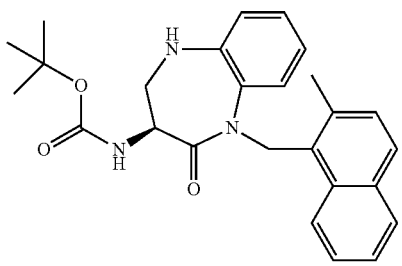 [SMILES: Cc1ccc2ccccc2c1CN1C(=O)[C@@H](NC(=O)OC(C)(C)C)CNc2ccccc21]

To a solution of 3.0 g (10.83 mmol) ((S)-2-oxo-2,3,4,5-tetrahydro-1H-benzo[b][1,4]diazepin-3-yl)-carbamic acid tert-butyl ester (Intermediate 2) in 55 mL of anhydrous tetrahydrofuran at −78° C. was added slowly a solution of 1 M lithium bis(trimethylsilyl)amide in tetrahydrofuran (24 mL, 24 mmol). The solution was stirred at −78° C. for 30 min. A solution of 5.35 g (28.2 mmol) 1-chloromethyl-2-methyl-naphthalene in 15 mL of tetrahydrofuran was slowly added. The reaction mixture was stirred at −78° C. for 10 min, the cooling bath was removed and the mixture stirred overnight. Potassium iodide (1.8 g, 10.83 mmol) was added to the mixture. After 2 h, water and ethyl acetate were added to the mixture, the organic layer was washed with 10% aqueous sodium bisulfate, brine, dried over anhydrous sodium sulfate, filtered and the filtrate concentrated. The residue was purified by silica gel chromatography to afford the title compound (3.2 g) as a light yellow solid. LC-MS: 432 (M+H).

Intermediate 9

[(S)-7-Cyano-1-(2-methyl-naphthalen-1-ylmethyl)-2-oxo-2,3,4,5-tetrahydro-1H-benzo[b][1,4]diazepin-3-yl]-carbamic acid tert-butyl ester

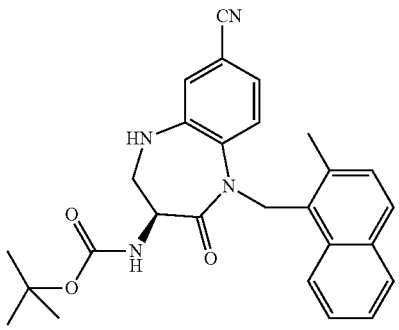 [SMILES: Cc1ccc2ccccc2c1CN1C(=O)[C@@H](NC(=O)OC(C)(C)C)CNc2cc(C#N)ccc21]

To a stirred solution of (S)-7-cyano-2-oxo-2,3,4,5-tetrahydro-1H-benzo[b][1,4]diazepin-3-yl)-carbamic acid tert-butyl ester (Intermediate 3) (300 mg, 0.993 mmol) in THF (10 mL) at −78° C. was added LiHMDS (1 M in THF, 1.19 mL, 1.19 mmol). After 20 min. 1-chloromethyl-2-methyl-naphthalene (227.289 mg, 1.192 mmol) and NaI (178.677 mg, 1.192 mmol) in THF (5 mL) was added to the mixture. After 1 h the cooling bath was removed, the mixture stirred for 16 h, diluted with citric acid solution (1 N) and extracted with ethyl acetate. The combined extracts were washed with water, brine, dried over Na$_2$SO$_4$ and concentrated. The residue was purified by silica gel chromatography to afford the title compound (400 mg, 88.2%) as an off white solid.
LC-MS: 457.2 (M+H).

Intermediate 10

[(S)-1-(6-Bromo-2-methoxy-naphthalen-1-ylmethyl)-7-cyano-2-oxo-2,3,4,5-tetrahydro-1H-benzo[b][1,4]diazepin-3-yl]-carbamic acid tert-butyl ester

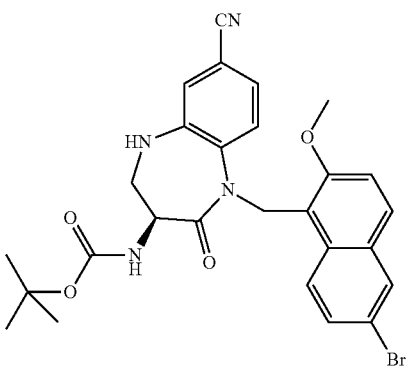 [SMILES: COc1ccc2cc(Br)ccc2c1CN1C(=O)[C@@H](NC(=O)OC(C)(C)C)CNc2cc(C#N)ccc21]

To a solution of (S)-7-cyano-2-oxo-2,3,4,5-tetrahydro-1H-benzo[b][1,4]diazepin-3-yl)-carbamic acid tert-butyl ester (Intermediate 3)(500 mg, 1.656 mmol) in THF at −78° C. was added LiHMDS (1.98 mL, 1.987 mmol). After 20 min. a mixture of 6-bromo-1-chloromethyl-2-methoxy-naphthalene (519 mg, 1.821 mmol) and NaI (297.8 mg, 1.987 mmol) in THF (10 mL) was added. After 1 h, the cooling bath was removed, the mixture stirred for 16 h, diluted with citric acid solution (1 N) and extracted with ethyl acetate. The combined extracts were washed with water, brine, dried over Na₂SO₄ and concentrated. The combined extracts were washed with water, brine, dried over Na₂SO₄ and concentrated. The residue was purified by silica gel chromatography to afford the title compound (638 mg, 69.88%) as an off white solid. LC-MS: 550.9 (M+H).

Intermediate 11

{(S)-1-[(S)-1-(6-Bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester

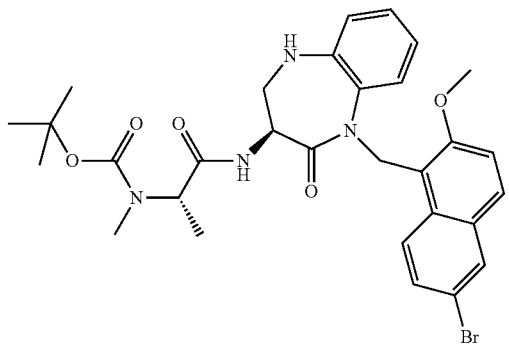 [SMILES: COc1ccc2cc(Br)ccc2c1CN1C(=O)[C@@H](NC(=O)[C@H](C)N(C)C(=O)OC(C)(C)C)CNc2ccccc21]

Step 1: To a stirred solution of [(S)-1-(6-bromo-2-methoxy-naphthalen-1-ylmethyl)-2-oxo-2,3,4,5-tetrahydro-1H-benzo[b][1,4]diazepin-3-yl]-carbamic acid tert-butyl ester (Intermediate 4)(100 mg, 0.19 mmol) in DCM (2 mL) at 0° C. was added 50% TFA in DCM (4 mL) dropwise. After 2 h the mixture was evaporated and the residue was washed with ether to afford (S)-3-amino-1-(6-bromo-2-methoxy-naphthalen-1-ylmethyl)-1,3,4,5-tetrahydro-benzo[b][1,4]diazepin-2-one trifluoroacetate (72 mg, 70.58%). LC-MS: 426 (M+H).

Step 2: Boc-N-Me-Ala-OH (650 mg, 3.19 mmol), HATU (1.32 g, 3.48 mmol) and DIPEA (1.52 mL, 8.72 mmol) were added to a solution of (S)-3-amino-1-(6-bromo-2-methoxy-naphthalen-1-ylmethyl)-1,3,4,5-tetrahydro-benzo[b][1,4]diazepin-2-one trifluoroacetate (1.6 g, 2.90 mmol) in DMF (10 mL). After 18 the mixture was evaporated and the mixture diluted with ethyl acetate. The mixture was washed with water, brine, dried (Na₂SO₄) and concentrated. The residue was purified by silica gel chromatography to afford the title compound (1.6 g, 88%) as a yellow solid. LC-MS: 611 (M+H).

Intermediate 12

{(S)-1-[(S)-1-(5-Bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester

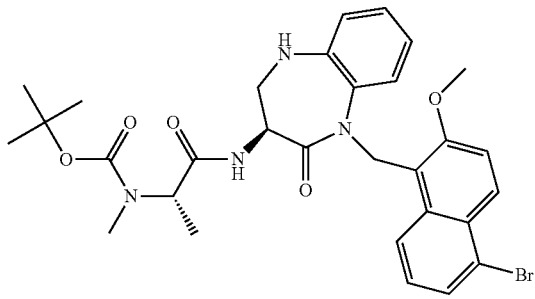 [SMILES: COc1ccc2c(Br)cccc2c1CN1C(=O)[C@@H](NC(=O)[C@H](C)N(C)C(=O)OC(C)(C)C)CNc2ccccc21]

Step 1: To a solution of [(S)-1-(5-bromo-2-methoxy-naphthalen-1-ylmethyl)-2-oxo-2,3,4,5-tetrahydro-1H-benzo[b][1,4]diazepin-3-yl]-carbamic acid tert-butyl ester (Intermediate 5) (480 mg, 0.913 mmol) in DCM (8 mL) at 0° C. was added TFA (1.9 mL) dropwise. The mixture was stirred for 2 h at RT and evaporated. The residue was triturated with hexane to afford (S)-3-amino-1-(5-bromo-2-methoxy-naphthalen-1-ylmethyl)-1,3,4,5-tetrahydro-benzo[b][1,4]diazepin-2-one trifluoroacetate (260 mg) as brown solid. LC-MS: 428 (M+H).

Step 2: Boc-N-Me-Ala-OH (107.91 mg, 0.532 mmol), DIPEA (0.251 mL, 1.45 mmol) and HATU (220.37 mg, 0.58 mmol) were added to a solution of (S)-3-amino-1-(5-bromo-2-methoxy-naphthalen-1-ylmethyl)-1,3,4,5-tetrahydro-benzo[b][1,4]diazepin-2-one trifluoroacetate (260 mg) in DMF (4 mL) at 0° C. After 3 h the mixture was diluted with water and extracted with ethyl acetate. The extracts were washed with 1 M aqueous citric acid solution, brine, saturated aqueous sodium carbonate solution, dried and concentrated. The residue was purified by silica gel chromatography to afford the title compound (282 mg, 51%) as an off white solid. LC-MS: 613.2 (M+H).

Intermediate 13

{(S)-1-[(S)-1-(2-Methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester

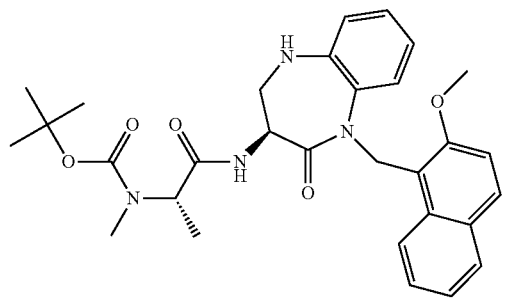 [SMILES: COc1ccc2ccccc2c1CN1C(=O)[C@@H](NC(=O)[C@H](C)N(C)C(=O)OC(C)(C)C)CNc2ccccc21]

Step 1: In a similar manner to that described for the preparation of (S)-3-amino-1-(5-bromo-2-methoxy-naphthalen-1-ylmethyl)-1,3,4,5-tetrahydro-benzo[b][1,4]diazepin-2-one trifluoroacetate (Intermediate 12, Step 1), [(S)-1-(2-methoxy-naphthalen-1-ylmethyl)-2-oxo-2,3,4,5-tetrahydro-1H-benzo[b][1,4]diazepin-3-yl]-carbamic acid tert-butyl ester (Intermediate 6) (450 mg, 1.007 mmol) was converted to (S)-3-amino-1-(2-methoxy-naphthalen-1-ylmethyl)-1,3,4,5-tetrahydro-benzo[b][1,4]diazepin-2-one trifluoroacetate (460 mg, crude) obtained as brown solid. LC-MS: 348.2 (M+H).

Step 2: In a similar manner to that described for the preparation of {(S)-1-[(S)-1-(5-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 12), (S)-3-amino-1-(2-methoxy-naphthalen-1-ylmethyl)-1,3,4,5-tetrahydro-benzo[b][1,4]diazepin-2-one trifluoroacetate salt (Step 1 above) (460 mg) and Boc-N-Me-Ala-OH (223.3 mg, 1.1 mmol) were converted to the title compound (390 mg, 73.2%) obtained as a white solid. LC-MS: 533 (M+H).

Intermediate 14

((S)-1-{(S)-1-[1-(2-Cyano-phenyl)-1H-indazol-3-ylmethyl]-2-oxo-2,3,4,5-tetrahydro-1H-benzo[b][1,4]diazepin-3-ylcarbamoyl}-ethyl)-methyl-carbamic acid tert-butyl ester

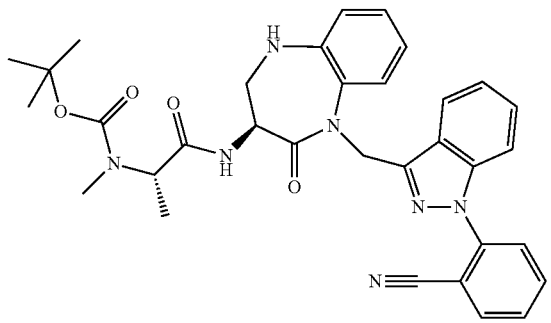 [SMILES: C[C@@H](C(=O)N[C@H]1CNc2ccccc2N(Cc2nn(-c3ccccc3C#N)c3ccccc23)C1=O)N(C)C(=O)OC(C)(C)C]

Step 1: In a similar manner to that described for the preparation of (S)-3-amino-1-(5-bromo-2-methoxy-naphthalen-1-ylmethyl)-1,3,4,5-tetrahydro-benzo[b][1,4]diazepin-2-one trifluoroacetate (Intermediate 12, Step 1), {(S)-1-[1-(2-cyano-phenyl)-1H-indazol-3-ylmethyl]-2-oxo-2,3,4,5-tetrahydro-1H-benzo[b][1,4]diazepin-3-yl}-carbamic acid tert-butyl ester (Intermediate 7) (670 mg, 1.319 mmol) was converted to 2-[3-((S)-3-amino-2-oxo-2,3,4,5-tetrahydro-benzo[b][1,4]diazepin-1-ylmethyl)-indazol-1-yl]-benzonitrile trifluoroacetate (680 mg) obtained as yellow solid. LC-MS: 408.8 (M+H).

Step 2: In a similar manner to that described for the preparation of {(S)-1-[(S)-1-(5-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 12), 2-[3-((S)-3-amino-2-oxo-2,3,4,5-tetrahydro-benzo[b][1,4]diazepin-1-ylmethyl)-indazol-1-yl]-benzonitrile trifluoroacetate (step 1 above) (680 mg, 1.30 mmol) and Boc-N-Me-Ala-OH (290.88 mg, 1.43 mmol) were converted to the title compound (570 mg, 72.8%) obtained as white solid. LC-MS: 594 (M+H).

Intermediate 15

Methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester

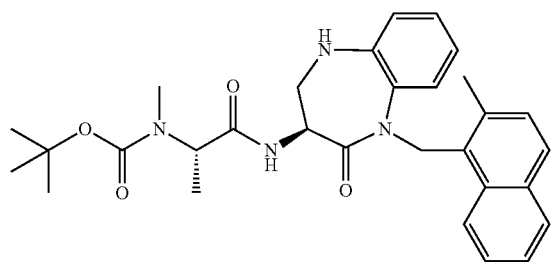 [SMILES: Cc1ccc2ccccc2c1CN1C(=O)[C@@H](NC(=O)[C@H](C)N(C)C(=O)OC(C)(C)C)CNc2ccccc21]

Step 1: [(S)-1-(2-Methyl-naphthalen-1-ylmethyl)-2-oxo-2,3,4,5-tetrahydro-1H-benzo[b][1,4]diazepin-3-yl)-carbamic acid tert-butyl ester (intermediate 8)(1.29 g, 3.0 mmol) in 20 mL of 4.0M HCl in 1,4-dioxane was stirred at room temperature overnight. The solvent was removed and the residue was lyophilized for to give (S)-3-amino-1-(2-methyl-naphthalen-1-ylmethyl)-1,3,4,5-tetrahydro-benzo[[b][1,4]diazepin-2-one hydrochloride (1.10 g) as a white solid which was used without purification.

Step 2: To a mixture of (S)-3-amino-1-(2-methyl-naphthalen-1-ylmethyl)-1,3,4,5-tetrahydro-benzo[[b][1,4]diazepin-2-one hydrochloride (1.10 g, 3 mmol), 1-hydroxybenzotriazole hydrate (0.50 g, 3.3 mmol), Boc-N-Me-Ala-OH (0.64 g, 3.15 mmol), diisopropylethylamine (2.1 mL, 12.0 mmol) in dimethylformamide (18 mL) at 0° C. was added O-(benzotriazol-1-yl)-N,N,N',N'-bis(tetramethylene)uronium hexafluorophosphate (1.25 g, 3.3 mmol). The mixture was stirred at room temperature for 4 h, diluted with ethyl acetate, washed with aqueous sodium carbonate, brine, 1M citric acid, brine, dried over anhydrous sodium sulfate, filtered and the filtrate concentrated. The residue was purified by silica gel chromatography to provide the title compound as a white solid. LC-MS: 517 (M+H).

Intermediate 16

{(S)-1-[(S)-7-Cyano-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester

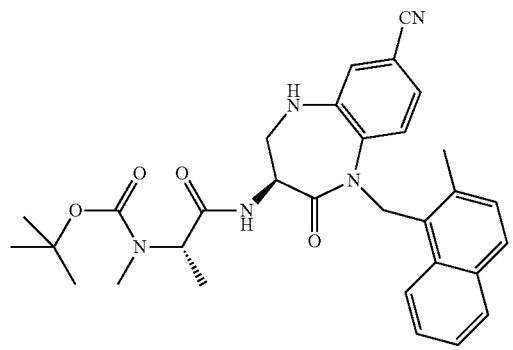 [SMILES: Cc1ccc2ccccc2c1CN1C(=O)[C@@H](NC(=O)[C@H](C)N(C)C(=O)OC(C)(C)C)CNc2cc(C#N)ccc21]

Step 1: To a solution of [(S)-7-cyano-1-(2-methyl-naphthalen-1-ylmethyl)-2-oxo-2,3,4,5-tetrahydro-1H-benzo[b][1,4]diazepin-3-yl]-carbamic acid tert-butyl ester (Intermediate 9) (400 mg, 0.877 mmol) in 1,4 dioxane (3 mL) at 0° C. was added 4 N HCl in dioxane solution (0.7 mL) dropwise. The mixture was stirred for 16 h at RT. The mixture was concentrated and the residue was triturated with diethyl ether to provide (S)-3-amino-1-(2-methyl-naphthalen-1-ylmethyl)-2-oxo-2,3,4,5-tetrahydro-1H-benzo[b][1,4]diazepine-7-carbonitrile hydrochloride (310 mg, 90.15%) obtained as an off white solid. LC-MS: 357.2 (M+H).

Step 2: To a stirred solution of (S)-3-amino-1-(2-methyl-naphthalen-1-ylmethyl)-2-oxo-2,3,4,5 tetrahydro-1H-benzo[b][1,4]diazepine-7-carbonitrile hydrochloride (305 mg, 0.778 mmol) in DMF (10 mL) was added Boc-N-Me-Ala-OH (173.912 mg, 0.856 mmol), HOBT (115.645 mg, 0.856 mmol) and DIPEA (0.67 mL, 3.89 mmol). After 10 min, the mixture was cooled to 0° C. and HBTU (324.63 mg, 0.856 mmol) was added. After 2 h, the mixture was diluted with ethyl acetate, washed with water, brine, dried over Na$_2$SO$_4$ and concentrated. The residue was purified by silica gel chromatography to afford the title compound (390 mg, 92.54%) as an off white solid. LC-MS: 542.0 (M+H).

Intermediate 17

{(S)-1-[(S)-1-(6-Bromo-2-methoxy-naphthalen-1-ylmethyl)-7-cyano-2-oxo-2,3,4,5-tetrahydro-1H-benzo[b][1,4]diazepin-3-ylcarbamoyl]-ethyl}-methyl-carbamic acid tert-butyl ester

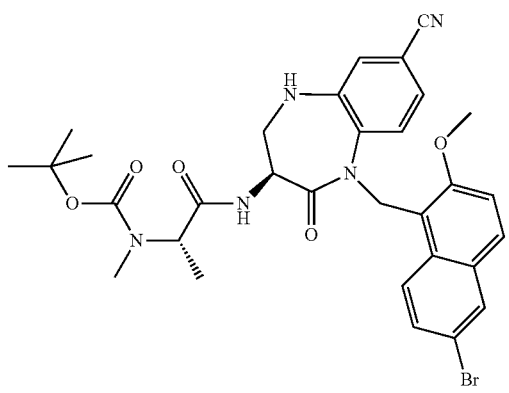 [SMILES: COc1ccc2cc(Br)ccc2c1CN1C(=O)[C@@H](NC(=O)[C@H](C)N(C)C(=O)OC(C)(C)C)CNc2cc(C#N)ccc21]

Step 1: In a similar manner to that described for the preparation of (S)-3-amino-1-(2-methyl-naphthalen-1-ylmethyl)-2-oxo-2,3,4,5-tetrahydro-1H-benzo[b][1,4]diazepine-7-carbonitrile hydrochloride (Intermediate 16, Step 1) except the mixture was triturated with ether followed by hexane, [(S)-1-(6-bromo-2-methoxy-naphthalen-1-ylmethyl)-7-cyano-2-oxo-2,3,4,5-tetrahydro-1Hbenzo[b][1,4]diazepin-3-yl]-carbamic acid tert-butyl ester (Intermediate 10) (630 mg, 1.143 mmol) was converted to (S)-3-amino-1-(6-bromo-2-methoxy-naphthalen-1-ylmethyl)-2-oxo-2,3,4,5-tetrahydro-1H-benzo[b][1,4]diazepine-7-carbonitrile hydrochloride (510 mg, 91.53%) obtained as white solid. LC-MS: 450.8 (M+H).

Step 2: To a solution of (S)-3-amino-1-(6-bromo-2-methoxy-naphthalen-1-ylmethyl)-2-oxo-2,3,4,5-tetrahydro-1Hbenzo[b][1,4]diazepine-7-carbonitrile hydrochloride (510 mg, 1.047 mmol) in DMF (10 mL) were added Boc-N-Me-Ala-OH (234 mg, 1.15 mmol), HOBT (155.62 mg, 1.15 mmol) and DIPEA (0.943 mL, 5.236 mmol). After 10 min, the mixture was cooled to 0° C. and HBTU (436.7 mg, 1.152 mmol) was added portion wise. The resulting mixture was stirred for 2 h. The mixture was diluted with water and extracted with EtOAc. The extracts were washed with 1 M aqueous citric acid solution, brine, saturated aqueous sodium carbonate solution, dried over Na$_2$SO$_4$ and concentrated. The residue was purified by silica gel column chromatography to afford the title compound (570 mg, 85.58%) as an off-white solid. LC-MS: 636.0 (M+H).

Intermediate 18a

Trans-1,4-cyclohexane-dicarbonyl dichloride

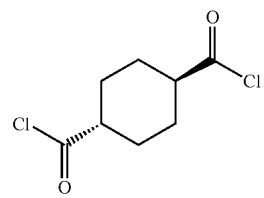 [SMILES: O=C(Cl)[C@H]1CC[C@H](C(=O)Cl)CC1]

To trans-1,4-cyclohexane-dicarboxylic acid (500 mg, 2.9 mmol) at 0° C. was added SOCl$_2$ (8 mL) followed by the addition of a catalytic amount DMF. The resulting mixture was refluxed for 3 h and the mixture was concentrated under inert atmosphere to give trans-1,4-cyclohexane-dicarbonyl dichloride (510 mg) which was used without purification.

The compounds shown in Table 1 were prepared following the procedure described for the preparation of trans-1,4-cyclohexane-dicarbonyl dichloride.

TABLE 1

| Compound | Name |
|---|---|
| ![pyridine-3,5] | Pyridine-3,5-dicarbonyl dichloride (Intermediate 18b) |
| ![2-methyl-terephthaloyl] | 2-Methyl-terephthaloyl dichloride (Intermediate 18c) |
| ![pyridine-2,5] | Pyridine-2,5-dicarbonyl dichloride (Intermediate 18d) |

TABLE 1-continued

| Compound | Name |
|---|---|
| 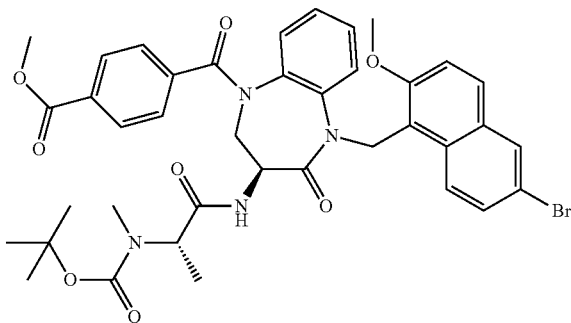 [SMILES: COC(=O)c1ccc(C(=O)N2C[C@H](NC(=O)[C@H](C)N(C)C(=O)OC(C)(C)C)C(=O)N(Cc3c(OC)ccc4cc(Br)ccc34)c3ccccc32)cc1] | 2,5-Dimethyl-terephthaloyl dichloride (Intermediate 18e) |

Intermediate 19

4-{(S)-5-(6-Bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepine-1-carbonyl}-benzoic acid methyl ester

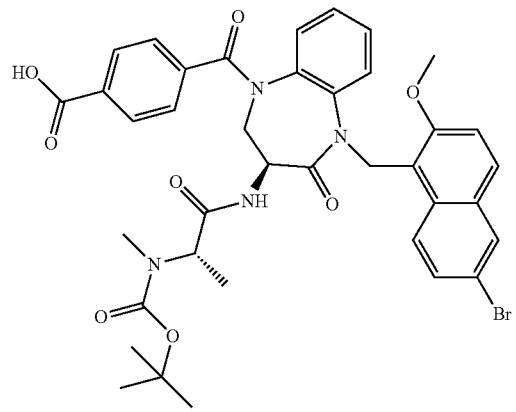 [SMILES: COc1ccc2cc(Br)ccc2c1CN1C(=O)[C@@H](NC(=O)[C@H](C)N(C)C(=O)OC(C)(C)C)CN(C(=O)c2ccc(C(=O)O)cc2)c2ccccc21]

To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 11) (1.5 g, 2.455 mmol) in pyridine (20 mL) at 0° C. was added terephthalic acid monomethyl ester (884 mg, 4.91 mmol). The mixture was stirred for 10 min at 0° C. and POCl₃ (0.472 mL, 5.155 mmol) was slowly added, the cooling bath removed and the mixture stirred at RT. After 16 h the mixture was evaporated and the residue diluted with ice water and extracted with ethyl acetate. The combined extracts were washed with water, brine, dried over Na₂SO₄ and concentrated. The residue was purified by silica gel chromatography to give the title compound. The sequence was repeated to provide a total of 4.2 g of the title compound from as an off white solid. LC-MS: 773 (M+H).

Intermediate 20

4-{(S)-5-(6-Bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepine-1-carbonyl}-benzoic acid To a solution of 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepine-1-carbonyl}-benzoic acid methyl ester (Intermediate 19) (4 g, 5.175 mmol) in THF-MeOH-water 1:1:1 (90 mL) were slowly added a solution of LiOH.H₂O solution (574 mg, 13.6 m mol) in water. After 4 h the mixture was concentrated, the residue was diluted with water and acidified to pH~3 with 1 N HCl. The mixture was extracted with ethyl acetate, the extracts were dried over sodium sulfate and evaporated. The residue was triturated with hexane to give the title compound (3.6 g, 91.58%) as an off white solid. LC-MS: 759 (M+H).

Intermediate 21

(2S,4S)-4-(9H-Fluoren-9-ylmethoxycarbonylamino)-2-[(R)-(1,2,3,4-tetrahydro-naphthalen-1yl)carbamoyl]-pyrrolidine-1-carboxylic acid tert-butyl ester

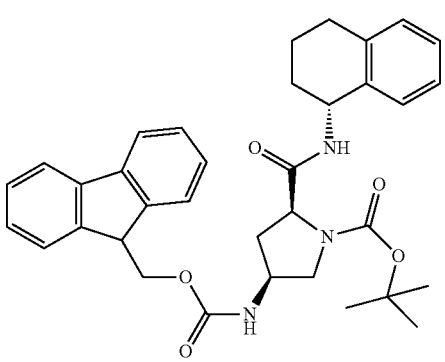 [SMILES: CC(C)(C)OC(=O)N1C[C@@H](NC(=O)OCC2c3ccccc3-c3ccccc32)C[C@H]1C(=O)N[C@@H]1CCCc2ccccc21]

To a solution of (2S,4S)-4-(9H-fluoren-9-ylmethoxycarbonylamino)-pyrrolidine-1,2-dicarboxylic acid 1-tert-butyl ester (Aldrich) (7.5 g, 16.593 mmol) in DMF (100 mL) were added HATU (6.93 g, 18.252 mmol) and DIPEA (14.36 mL, 82.965 mmol) and the mixture was cooled to 0° C. (R)-(1,2,3,4-tetrahydro-naphthalen-1-yl)amine (2.44 g, 16.593 mmol) was added dropwise and the cooling bath removed. After 4 h the mixture was diluted with ethyl acetate, washed with water, dried over sodium sulfate and concentrated to afford the title compound as an off white solid (9.6 g) which was used without purification. LC-MS: 582 (M+H).

Intermediate 22

({(3S,5S)-5-[(R)-(1,2,3,4-Tetrahydro-naphthalen-1-yl)carbamoyl]-pyrrolidin-3-yl}-carbamic acid 9H-fluoren-9-ylmethyl ester trifluoroacetate

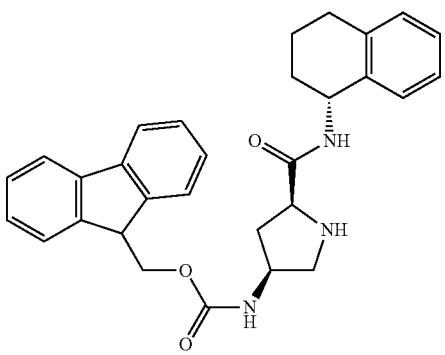 [SMILES: O=C(N[C@@H]1CN[C@H](C(=O)N[C@@H]2CCCc3ccccc32)C1)OCC1c2ccccc2-c2ccccc21]

To a solution of (2S,4S)-4-(9H-fluoren-9-ylmethoxycarbonylamino)-2-[(R)-(1,2,3,4-tetrahydro-naphthalen-1-yl)carbamoyl]-pyrrolidine-1-carboxylic acid tert-butyl ester (Intermediate 21) (9.5 g, 16.35 mmol) in DCM (50 mL) at 0° C. was added TFA (49 mL, 654.045 mmol) dropwise and the cooling bath removed. After 16 h the mixture was concentrated and the residue was triturated with ether to provide the title compound as an off white solid (9.55 g). LC-MS: 482 (M+H).

Intermediate 23

{(3S,5S)-1-((S)-2-tert-butoxycarbonylamino-2-cyclohexyl-acetyl)-5-[(R)-(1,2,3,4-tetrahydro-naphthalen-1-yl)carbamoyl]-pyrrolidin-3-yl}-carbamic acid 9H-fluoren-9-ylmethyl ester

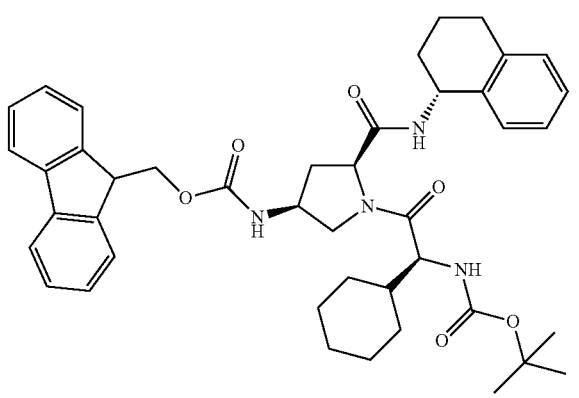 [SMILES: CC(C)(C)OC(=O)N[C@H](C(=O)N1C[C@@H](NC(=O)OCC2c3ccccc3-c3ccccc32)C[C@H]1C(=O)N[C@@H]1CCCc2ccccc21)C1CCCCC1]

To a solution of (S)-tert-butoxycarbonylamino-cyclohexyl-acetic acid (Aldrich) (4.529 g, 17.622 mmol) in DMF (100 mL) were added HATU (6.7 g, 17.622 mmol) followed by DIPEA (13.87 mL, 80.101 mmol). The mixture was cooled to 0° C. and ({(3S,5S)-5-[(R)-(1,2,3,4-tetrahydro-naphthalen-1-yl)carbamoyl]-pyrrolidin-3-yl}-carbamic acid 9H-fluoren-9-ylmethyl ester trifluoroacetate (Intermediate 22) (9.5 g, 16.02 mmol) in DMF (50 mL) was added dropwise and then the cooling bath removed. After 4 h the mixture was diluted with ethyl acetate, washed with water, dried over sodium sulfate and concentrated to give the title compound as an off white solid (10 g) which was used without purification. LC-MS: 721 (M+H).

Intermediate 24

{(3S,5S)-1-((S)-2-Amino-2-cyclohexyl-acetyl)-5-[(R)-(1,2,3,4-tetrahydro-naphthalen-1-yl)carbamoyl]-pyrrolidin-3-yl}-carbamic acid 9H-fluoren-9-ylmethyl ester hydrochloride

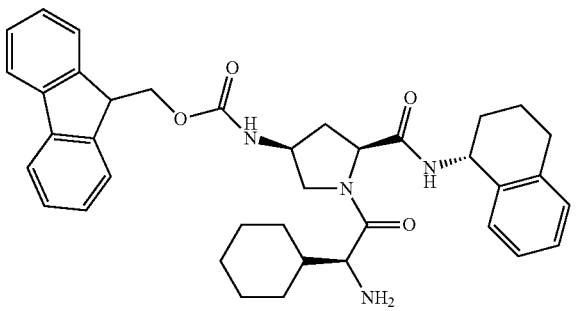 [SMILES: N[C@H](C(=O)N1C[C@@H](NC(=O)OCC2c3ccccc3-c3ccccc32)C[C@H]1C(=O)N[C@@H]1CCCc2ccccc21)C1CCCCC1]

To a stirred solution of {(3S,5S)-1-((S)-2-tert-butoxycarbonylamino-2-cyclohexyl-acetyl)-5-[(R)-(1,2,3,4-tetrahydro-naphthalen-1-yl)carbamoyl]-pyrrolidin-3-yl}-carbamic acid 9H-fluoren-9-ylmethyl ester (Intermediate 23) (6.5 g, 9.03 mmol) in dioxane (25 mL) at 0° C. was added 4 M HCl in dioxane (50 mL) dropwise and then the cooling bath removed. After 6 h the mixture was evaporated and the residue was triturated with ether to provide the title compound (5.58 g) as a white solid. LC-MS: 621 (M+H).

Intermediate 25

{(3S,5S)-1-{(S)-2-[(S)-2-(tert-Butoxycarbonyl-methyl-amino)-propionylamino]-2-cyclohexyl-acetyl}-5-[(R)-(1,2,3,4-tetrahydro-naphthalen-1-yl)carbamoyl]-pyrrolidin-3-yl}-carbamic acid 9H-fluoren-9-ylmethyl ester

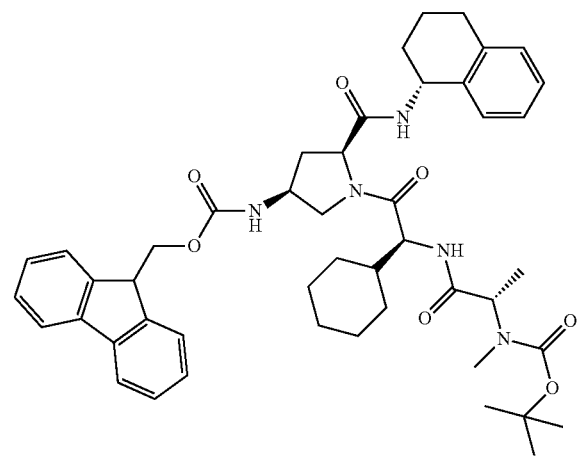 [SMILES: C[C@@H](C(=O)N[C@H](C(=O)N1C[C@@H](NC(=O)OCC2c3ccccc3-c3ccccc32)C[C@H]1C(=O)N[C@@H]1CCCc2ccccc21)C1CCCCC1)N(C)C(=O)OC(C)(C)C]

To a stirred solution of Boc-N-Me-Ala-OH (2.55 g, 12.57 mmol) in DMF (30 mL) were added HATU (4.78 g, 12.57 mmol) and DIPEA (9.9 mL, 57.16 mmol). After 30 min, the mixture was cooled to 0° C. and {(3S,5S)-1-((S)-2-amino-2-cyclohexyl-acetyl)-5-[(R)-(1,2,3,4-tetrahydro-naphthalen-1-yl)carbamoyl]-pyrrolidin-3-yl}-carbamic acid 9H-fluoren-9-ylmethyl ester (Intermediate 24) (7.5 g, 11.43 mmol) in DMF (50 mL) and the cooling bath removed. After 4 h the mixture was diluted with ethyl acetate, washed with water, dried over sodium sulfate and concentrated. The residue was purified by silica gel chromatography to afford the title compound as an off white solid (5.32 g) LC-MS: 806 (M+H).

Intermediate 26

[(S)-1-((S)-2-{(2S,4S)-4-Amino-2-[(R)-(1,2,3,4-tetrahydro-naphthalen-1-yl)carbamoyl]-pyrrolidin-1-yl}-1-cyclohexyl-2-oxo-ethylcarbamoyl)-ethyl]-methyl-carbamic acid tert-butyl ester

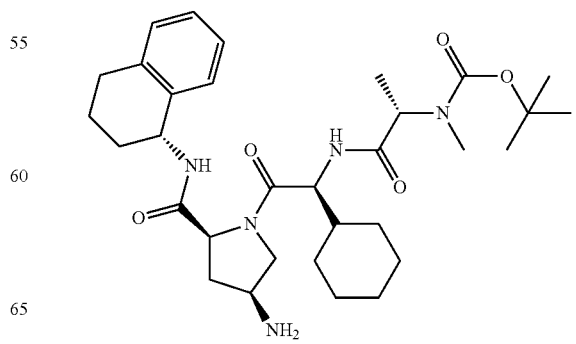

{(3S,5S)-1-{(S)-2-[(S)-2-(tert-Butoxycarbonyl-methylamino)-propionylamino]-2-cyclohexyl-acetyl}-5-[(R)-(1,2,3,4-tetrahydro-naphthalen-1-yl)carbamoyl]-pyrrolidin-3-yl}-carbamic acid 9H-fluoren-9-ylmethyl ester (Intermediate 25) (100 mg, 124 μM) was dissolved in DMF (0.9 mL) at room temperature and piperidine (0.1 mL) was added. The mixture was stirred at room temperature for 30 minutes, concentrated and the residue purified by chromatography over silica gel to give the title compound as white foam (56.7 mg, 78%). LC-MS: 585 (M+H).

Intermediate 27

(2S,4S)-1-{(S)-2-[(S)-2-(tert-Butoxycarbonyl-methyl-amino)-propionylamino]-2-cyclohexyl-acetyl}-4-(9H-fluoren-9-ylmethoxycarbonylamino)-pyrrolidine-2-carboxylic acid

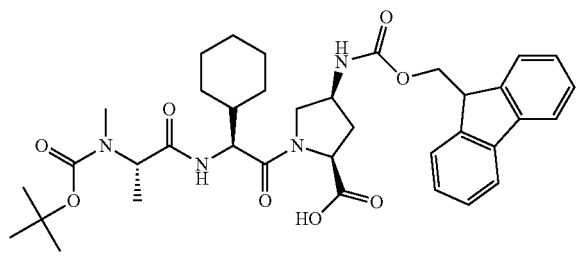 [SMILES: C[C@@H](C(=O)N[C@H](C(=O)N1C[C@@H](NC(=O)OCC2c3ccccc3-c3ccccc32)C[C@H]1C(=O)O)C1CCCCC1)N(C)C(=O)OC(C)(C)C]

Step 1: To a suspension of (2S,4S)-4-(9H-fluoren-9-ylmethoxycarbonylamino)-pyrrolidine-1,2-dicarboxylic acid 1-tert-butyl ester (Aldrich) (1 g, 2.21 mmol) in methanol (6 mL) was added a solution potassium carbonate (153 mg, 1.1 mmol) in water (6 mL) dropwise. The mixture was stirred at room temperature for 1 hour, concentrated, and the residue slurried in toluene and evaporated to dryness 3 times and once from diethyl ether to give a white solid. The solid was mixed with DMF (6 mL), and bromomethyl-benzene (289 μL, 2.43 mmol) was added dropwise at room temperature. After 16 hours the mixture was diluted with water extracted with ethyl acetate. The combined extracts were washed with water, brine and dried over anhydrous magnesium sulfate and concentrated. The residue was purified by silica gel chromatography to give (2S,4S)-4-(9H-fluoren-9-ylmethoxycarbonylamino)-pyrrolidine-1,2-dicarboxylic acid 2-benzyl ester 1-tert-butyl ester (0.92 g, 77%) as a foam.

Step 2: A mixture of 20 mL TFA/DCM (1:1) at 0° C. was added to (2S,4S)-4-(9H-fluoren-9-ylmethoxycarbonylamino)-pyrrolidine-1,2-dicarboxylic acid 2-benzyl ester 1-tert-butyl ester (0.92 g, 0.17 mmol) at 0° C., the cooling bath was removed and the mixture stirred for 2 h. The mixture was concentrated and triturated with diethyl ether to give (2S,4S)-4-(9H-Fluoren-9-ylmethoxycarbonylamino)-pyrrolidine-2-carboxylic acid benzyl ester trifluoroacetate (0.94 g) as a white solid.

Step 3: To a solution of (S)-tert-butoxycarbonylamino-cyclohexyl-acetic acid (Aldrich) (435 mg, 1.69 mmol) in DMF at 0° C. was added DIPEA (1.18 mL, 6.76 mmol) and HATU (674 mg, 1.77 mmol). After 30 minutes (2S,4S)-4-(9H-fluoren-9-ylmethoxycarbonylamino)-pyrrolidine-2-carboxylic acid benzyl ester trifluoroacetate (0.94 g, 1.69 mmol) was added in one portion. The cooling bath was removed and the mixture stirred for 1 h, diluted with water, the resulting white precipitate collected, washed with water and air-dried to give (2S,4S)-1-((S)-2-tert-butoxycarbonylamino-2-cyclo-hexyl-acetyl)-4-(9H-fluoren-9-ylmethoxycarbonylamino)-pyrrolidine-2-carboxylic acid benzyl ester (1.07 g, 93%).

Step 4: (2S,4S)-1-((S)-2-tert-Butoxycarbonylamino-2-cyclohexyl-acetyl)-4-(9H-fluoren-9-ylmethoxycarbonylamino)-pyrrolidine-2-carboxylic acid benzyl ester (1.07 g, 1.77 mmol) was dissolved in 4 M HCl in 1,4-dioxane (6 mL) at 0° C. and stirred for 1 h, the cooling bath removed and the reaction stirred for 1 h. The mixture was concentrated and the residue triturated with diethyl ether to give (2S,4S)-1-((S)-2-amino-2-cyclohexyl-acetyl)-4-(9H-fluoren-9-ylmethoxycarbonylamino)-pyrrolidine-2-carboxylic acid benzyl ester hydrochloride (0.97 g) as a light yellow solid which was used without further purification or characterization.

Step 5: To a solution of Boc-N-Me-Ala-OH (351 mg, 1.73 mmol) in DMF at 0° C. was added DIPEA (1.27 mL, 8.85 mmol) and HATU (626 mg, 1.65 mmol). After 30 min, (2S,4S)-1-((S)-2-amino-2-cyclohexyl-acetyl)-4-(9H-fluoren-9-ylmethoxycarbonylamino)-pyrrolidine-2-carboxylic acid benzyl ester hydrochloride (0.97 g, 1.57 mmol) was added, the cooling bath removed and the reaction stirred for 1 h. The mixture was diluted with ethyl acetate, washed with saturated ammonium chloride solution, saturated sodium bicarbonate solution, water, and brine and dried over anhydrous magnesium sulfate. Concentration gave (2S,4S)-1-{(S)-2-[(S)-2-(tert-butoxycarbonyl-methyl-amino)-propionylamino]-2-cyclohexyl-acetyl}-4-(9H-fluoren-9-ylmethoxycarbonylamino)-pyrrolidine-2-carboxylic acid benzyl ester (1.2 g) as an oil that was used without further purification or characterization.

Step 6: (2S,4S)-1-{(S)-2-[(S)-2-(tert-Butoxycarbonyl-methyl-amino)-propionylamino]-2-cyclohexyl-acetyl}-4-(9H-fluoren-9-ylmethoxycarbonylamino)-pyrrolidine-2-carboxylic acid benzyl ester (1.2 g, 1.56 mmol) was dissolved in methanol (15 mL) and 10% Pd—C (200 mg) was added. The mixture was stirred under hydrogen (1 atm) for 1 h, filtered through Celite and concentrated to give the title compound (800 mg, 76%) as a colorless oil which solidified upon standing and was used without purification.

Intermediate 28

{(S)-1-[(S)-2-((2S,4S)-4-Amino-2-benzylcarbamoyl-pyrrolidin-1-yl)-1-cyclohexyl-2-oxo-ethylcarbamoyl]-ethyl}-methyl-carbamic acid tert-butyl ester

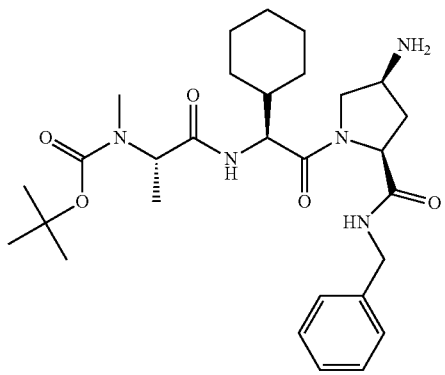 [SMILES: C[C@@H](C(=O)N[C@H](C(=O)N1C[C@@H](N)C[C@H]1C(=O)NCc1ccccc1)C1CCCCC1)N(C)C(=O)OC(C)(C)C]

Step 1: To (2S,4S)-1-{(S)-2-[(S)-2-(tert-butoxycarbonyl-methyl-amino)-propionylamino]-2-cyclohexyl-acetyl}-4--

(9H-fluoren-9-ylmethoxycarbonylamino)-pyrrolidine-2-carboxylic acid (Intermediate 27) in DMF at 0° C. was added DIPEA (116 μL, 0.66 mmol) and HATU (93 mg, 0.24 mmol). The mixture was stirred at 0° C. for 15 minutes and then benzylamine (26.1 mg, 0.24 mmol) in DMF (0.5 mL) was added dropwise, the cooling bath removed and the reaction stirred for 2 h. The mixture was diluted with water and extracted with EtOAc. The combined extracts were washed with saturated ammonium chloride solution, saturated sodium bicarbonate solution, water, and brine and dried over anhydrous magnesium sulfate. Concentration gave ((3S,5S)-5-benzylcarbamoyl-1-{(S)-2-[(S)-2-(tert-butoxycarbonyl-methyl-amino)-propionylamino]-2-cyclohexyl-acetyl}-pyrrolidin-3-yl)-carbamic acid 9H-fluoren-9-ylmethyl ester as a foam which was used without purification.

Step 2: ((3S,5S)-5-Benzylcarbamoyl-1-{(S)-2-[(S)-2-(tert-butoxycarbonyl-methyl-amino)-propionylamino]-2-cyclohexyl-acetyl}-pyrrolidin-3-yl)-carbamic acid 9H-fluoren-9-ylmethyl ester (100 mg, 0.13 mmol) was dissolved in DMF (0.9 mL) at room temperature and piperidine (0.1 mL) was added. The mixture was stirred at room temperature for 30 minutes, concentrated and the residue purified by silica gel chromatography to give the title compound as a white foam (71 mg, 52%).

Intermediate 29

[(S)-1-((S)-2-{(2S,4S)-4-Amino-2-[(S)-(1,2,3,4-tetrahydro-naphthalen-1-yl)carbamoyl]-pyrrolidin-1-yl}-1-cyclohexyl-2-oxo-ethylcarbamoyl)-ethyl]-methyl-carbamic acid tert-butyl ester

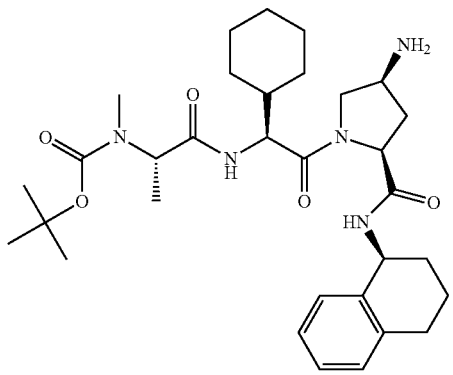 [SMILES: C[C@@H](C(=O)N[C@H](C(=O)N1C[C@@H](N)C[C@H]1C(=O)N[C@H]1CCCc2ccccc21)C1CCCCC1)N(C)C(=O)OC(C)(C)C]

In a similar manner to that described for {(S)-1-[(S)-2-((2S,4S)-4-amino-2-benzylcarbamoyl-pyrrolidin-1-yl)-1-cyclohexyl-2-oxo-ethylcarbamoyl]-ethyl}-methyl-carbamic acid tert-butyl ester (Intermediate 28), (2S,4S)-1-{(S)-2-[(S)-2-(tert-butoxycarbonyl-methyl-amino)-propionylamino]-2-cyclohexyl-acetyl}-4-(9H-fluoren-9-ylmethoxycarbonylamino)-pyrrolidine-2-carboxylic acid (Intermediate 27) (150 mg, 0.22 mmol) and (S)-(1,2,3,4-tetrahydro-naphthalen-1-yl)amine (Aldrich) (33 mg, 0.22 mmol) were converted to the title compound (48 mg, foam).

Intermediate 30

[(S)-1-((S)-2-{(2S,4S)-4-Amino-2-[(R)-(1,2,3,4-tetrahydro-naphthalen-1-yl)carbamoyl]-pyrrolidin-1-yl}-1-cyclohexyl-2-oxo-ethylcarbamoyl)-ethyl]-methyl-carbamic acid tert-butyl ester, alternate preparation

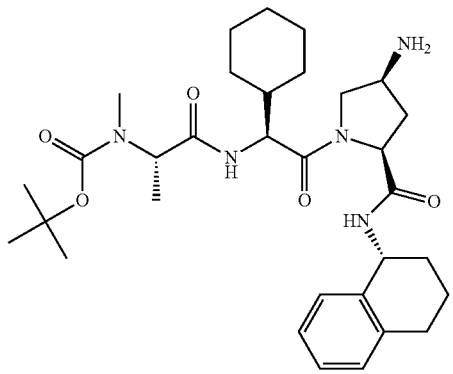 [SMILES: C[C@@H](C(=O)N[C@H](C(=O)N1C[C@@H](N)C[C@H]1C(=O)N[C@@H]1CCCc2ccccc21)C1CCCCC1)N(C)C(=O)OC(C)(C)C]

In a similar manner to that described for {(S)-1-[(S)-2-((2S,4S)-4-amino-2-benzylcarbamoyl-pyrrolidin-1-yl)-1-cyclohexyl-2-oxo-ethylcarbamoyl]-ethyl}-methyl-carbamic acid tert-butyl ester (Intermediate 28, Step 2), {(3S,5S)-1-{(S)-2-[(S)-2-(tert-butoxycarbonyl-methyl-amino)-propionylamino]-2-cyclohexyl-acetyl}-5-[(R)-(1,2,3,4-tetrahydro-naphthalen-1-yl)carbamoyl]-pyrrolidin-3-yl}-carbamic acid 9H-fluoren-9-ylmethyl ester (Intermediate 25) (500 mg, 0.62 mmol) was converted to the title compound (360 mg, foam).

Intermediate 31

{(S)-1-[(S)-2-((2S,4S)-4-Amino-2-cyclohexylcarbamoyl-pyrrolidin-1-yl)-1-cyclohexyl-2-oxo-ethylcarbamoyl]-ethyl}-methyl-carbamic acid tert-butyl ester

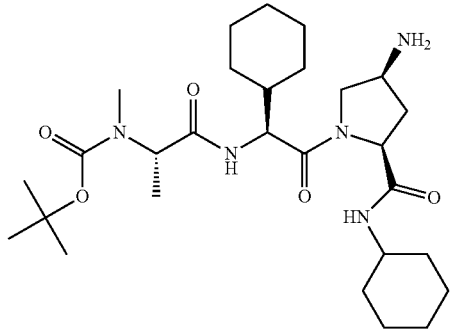 [SMILES: C[C@@H](C(=O)N[C@H](C(=O)N1C[C@@H](N)C[C@H]1C(=O)NC1CCCCC1)C1CCCCC1)N(C)C(=O)OC(C)(C)C]

In a similar manner to that described for {(S)-1-[(S)-2-((2S,4S)-4-amino-2-benzylcarbamoyl-pyrrolidin-1-yl)-1-cyclohexyl-2-oxo-ethylcarbamoyl]-ethyl}-methyl-carbamic acid tert-butyl ester (Intermediate 28), (2S,4S)-1-{(S)-2-[(S)-2-(tert-butoxycarbonyl-methyl-amino)-propionylamino]-2-cyclohexyl-acetyl}-4-(9H-fluoren-9-ylmethoxycarbonylamino)-pyrrolidine-2-carboxylic acid (Intermediate 27) (50 mg, 0.074 mmol) and cyclohexylamine (15 mg, 0.15 mmol) were converted to the title compound (74 mg, foam).

Intermediate 32

{(S)-1-[(S)-2-((2S,4S)-4-Amino-2-isopropylcarbamoyl-pyrrolidin-1-yl)-1-cyclohexyl-2-oxo-ethylcarbamoyl]-ethyl}-methyl-carbamic acid tert-butyl ester

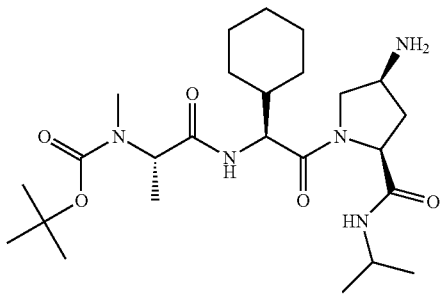 [SMILES: CC(C)NC(=O)[C@@H]1C[C@H](N)CN1C(=O)[C@@H](NC(=O)[C@H](C)N(C)C(=O)OC(C)(C)C)C1CCCCC1]

To (2S,4S)-1-{(S)-2-[(S)-2-(tert-butoxycarbonyl-methyl-amino)-propionylamino]-2-cyclohexyl-acetyl}-4-(9H-fluoren-9-ylmethoxycarbonylamino)-pyrrolidine-2-carboxylic acid (Intermediate 27) (50 mg, 73.9 µmol) in DMF at 0° C. was added DIPEA (29 mg, 222 mol) and HATU (31 mg, 81.3 µmol) and the mixture was stirred at 0° C. for 15 minutes. Isopropylamine (0.10 mL) was added, the cooling bath was removed and the mixture stirred at room temperature for 1 h. The mixture was evaporated to afford the title compound which was used without purification.

Example 1

(2S,4S)-N-Benzyl-4-[[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]pyrrolidine-2-carboxamide dihydrochloride

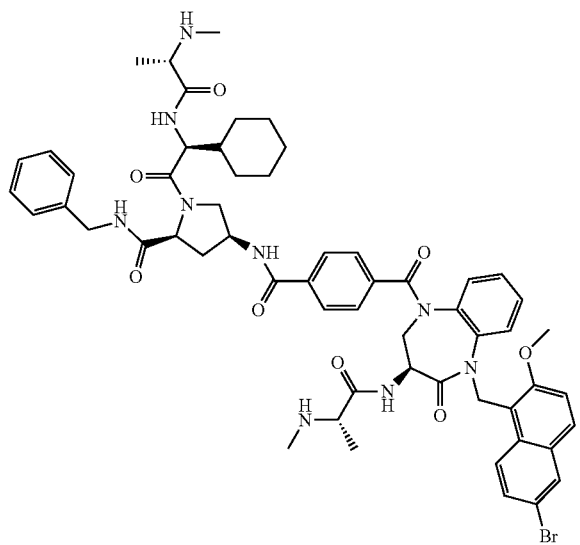 [SMILES: CN[C@@H](C)C(=O)N[C@H]1CN(C(=O)c2ccc(C(=O)N[C@H]3C[C@@H](C(=O)NCc4ccccc4)N(C(=O)[C@@H](NC(=O)[C@H](C)NC)C4CCCCC4)C3)cc2)c2ccccc2N(Cc2c(OC)ccc3cc(Br)ccc23)C1=O]

Step 1: To 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepine-1-carbonyl}-benzoic acid (Intermediate 20) (53 mg, 0.07 mmol) in DMF (3 mL) at 0° C. was added DIPEA and HATU. The mixture was stirred at 0° C. for 30 minutes and {(S)-1-[(S)-2-((2S,4S)-4-amino-2-benzylcarbamoyl-pyrrolidin-1-yl)-1-cyclohexyl-2-oxo-ethylcarbamoyl]-ethyl}-methyl-carbamic acid tert-butyl ester (Intermediate 28) (38 mg, 0.07 mmol) was added in one portion. The cooling bath was removed and the mixture stirred for 1 h, diluted with water and extracted with ethyl acetate. The combined extracts were washed with saturated ammonium chloride solution, saturated sodium bicarbonate solution, water, and brine and dried over anhydrous magnesium sulfate. Concentration gave an oily solid that was purified by chromatography over silica gel to give tert-butyl N-[(1S)-2-[[(1S)-2-[(2S,4S)-2-(benzylcarbamoyl)-4-[[4-[(3S)-5-[(6-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]benzoyl]amino]pyrrolidin-1-yl]-1-cyclohexyl-2-oxo-ethyl]amino]-1-methyl-2-oxo-ethyl]-N-methyl-carbamate (45 mg, 50%) as an oily solid.

Step 2: To tert-butyl N-[(1S)-2-[[(1S)-2-[(2S,4S)-2-(benzylcarbamoyl)-4-[[4-[(3S)-5-[(6-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]benzoyl]amino]pyrrolidin-1-yl]-1-cyclohexyl-2-oxo-ethyl]amino]-1-methyl-2-oxo-ethyl]-N-methyl-carbamate (45 mg, 0.035 mmol) in methanol (2 mL) at room temperature was added acetyl chloride (25 µL, 0.035 mmol) dropwise. The mixture was allowed to stand at room temperature. After 16 h the mixture was concentrated and the residue was triturated with acetonitrile to give the title compound (40 mg, 98%) as a tan solid. MS: m/z 1085 (MH+)

Examples 2-5

Following the procedures described above for the preparation of Example 1, 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepine-1-carbonyl}-benzoic acid (Intermediate 20) and the indicated amines were converted to the compounds shown in Table 2, which were obtained as the dihydrochloride salts.

TABLE 2

| Example | Amine | Product | MS (m/z) |
|---|---|---|---|
| Ex 2 | | | 1125 (MH+) |
| Ex 3 | | | 1125 (MH+) |
| Ex 4 | | | 1078 (MH+) |

TABLE 2-continued

| Example | Amine | Product | MS (m/z) |
|---|---|---|---|
| Ex 5 | | | 1037 (MH+) |

Example 6

(2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide dihydrochloride

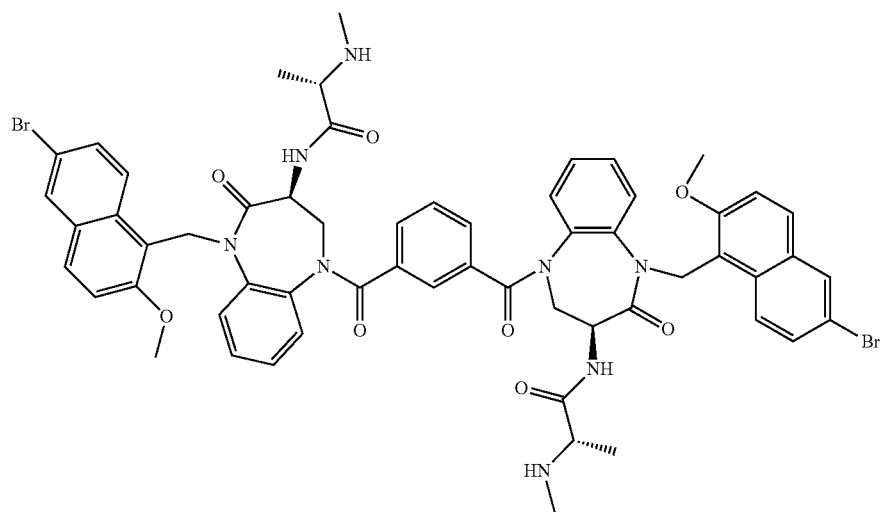 [SMILES: CN[C@@H](C)C(=O)N[C@H]1CN(C(=O)c2cccc(C(=O)N3C[C@H](NC(=O)[C@H](C)NC)C(=O)N(Cc4c(OC)ccc5cc(Br)ccc45)c4ccccc43)c2)c2ccccc2N(Cc2c(OC)ccc3cc(Br)ccc23)C1=O]

Step 1: To a stirred solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 11) (300 mg, 0.49 mmol) in THF (10.0 mL) was added Cs₂CO₃ (320 mg, 0.98 mmol) and stirred at RT for 3 h. The mixture was cooled to 0° C., isophthaloyl dichloride (49 mg, 0.24 mmol) was added, the cooling bath was removed and the mixture was stirred at RT. After 18 h, the mixture was diluted with ethyl acetate, washed with water and brine. The organic layer was evaporated and the residue purified by preparative reverse phase HPLC to afford tert-butyl N-[(1S)-2-[[(3S)-5-[(6-bromo-2-methoxy-1-naphthyl)methyl]-1-[3-[(3S)-5-[(6-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]benzoyl]-4-oxo-2,3-dihydro-1,5-benzodiazepin-3-yl]amino]-1-methyl-2-oxo-ethyl]-N-methyl-carbamate (18 mg, 3%). LC-MS: 1353.8 (M+H), 1370.8 (M+NH₄).

Step 2: To a stirred solution of tert-butyl N-[(1S)-2-[[(3S)-5-[(6-bromo-2-methoxy-1-naphthyl)methyl]-1-[3-[(3S)-5-[(6-bromo-2-methoxy-1-naphthyl)methyl]-3-[[(2S)-2-[tert-butoxycarbonyl(methyl)amino]propanoyl]amino]-4-oxo-2, 3-dihydro-1,5-benzodiazepine-1-carbonyl]benzoyl]-4-oxo-2,3-dihydro-1,5-benzodiazepin-3-yl]amino]-1-methyl-2-oxo-ethyl]-N-methyl-carbamate (15 mg, 0.01 mmol) in dioxane (0.2 mL) at 0° C. was added 4 N HCl in dioxane (0.2 mL), the cooling bath was removed and the mixture was stirred at RT. After 2 h, the mixture was evaporated to provide the title compound (8 mg, 58.9%) as an off white solid. LC-MS: 1153.6 (M+H).

Examples 7-18

Following the procedures described for the preparation of Example 6, {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 11) and the indicated dicarbonyl chlorides were converted to the compounds shown in Table 3, which were obtained as the dihydrochloride salts.

TABLE 3

| Example | Dicarbonyl Chloride | Product | MS (m/z) |
| --- | --- | --- | --- |
| Ex 7 | | | 1354 (M + H) |
| Ex 8 | | | 1354 (M + H) |
| Ex 9 | | | 1203 (M + H) |

TABLE 3-continued
| Example | Dicarbonyl Chloride | Product | MS (m/z) |
|---|---|---|---|
| Ex 10 | 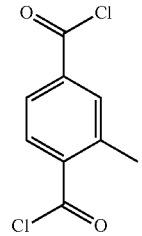 | 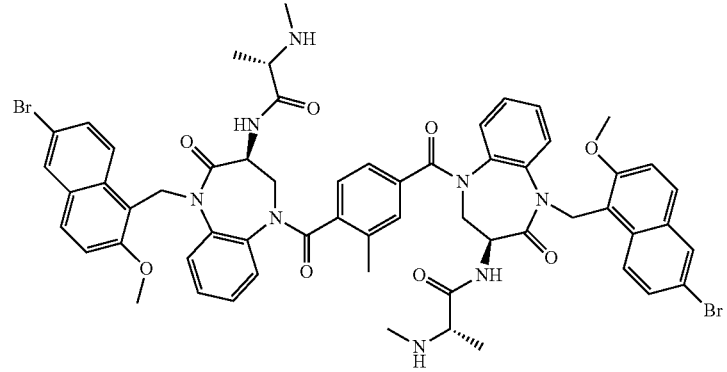 [SMILES: CN[C@@H](C)C(=O)N[C@H]1CN(C(=O)c2ccc(C(=O)N3C[C@H](NC(=O)[C@H](C)NC)C(=O)N(Cc4c(OC)ccc5cc(Br)ccc45)c4ccccc43)c(C)c2)c2ccccc2N(Cc2c(OC)ccc3cc(Br)ccc23)C1=O] | 1167 (M + H) |
| Ex 11 | 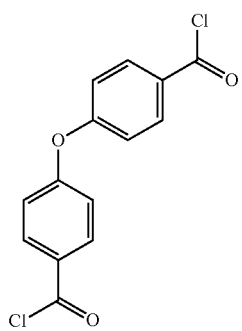 [SMILES: O=C(Cl)c1ccc(Oc2ccc(C(=O)Cl)cc2)cc1] | 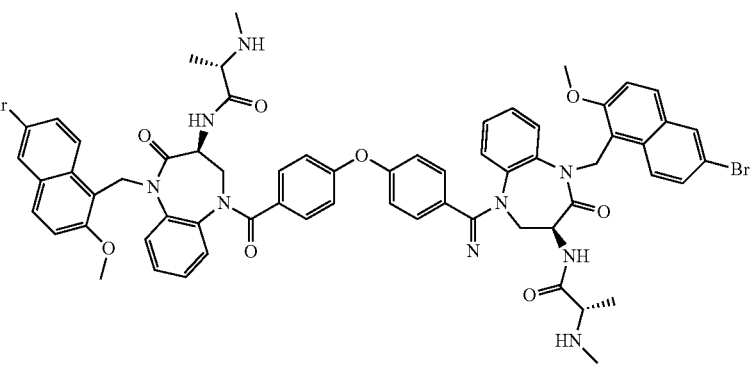 | 1245 (M + H) |
| Ex 12 | 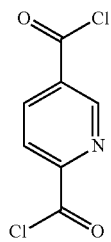 | 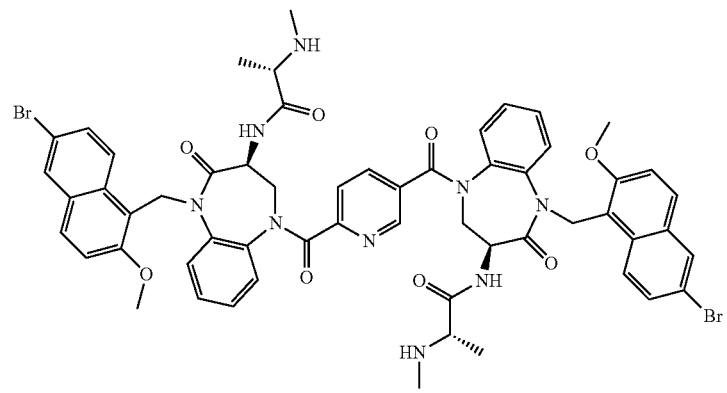 [SMILES: CN[C@@H](C)C(=O)N[C@H]1CN(C(=O)c2ccc(C(=O)N3C[C@H](NC(=O)[C@H](C)NC)C(=O)N(Cc4c(OC)ccc5cc(Br)ccc45)c4ccccc43)nc2)c2ccccc2N(Cc2c(OC)ccc3cc(Br)ccc23)C1=O] | 1154 (M + H) |
| Ex 13 | 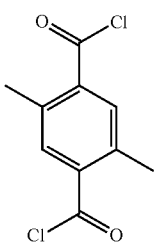 | 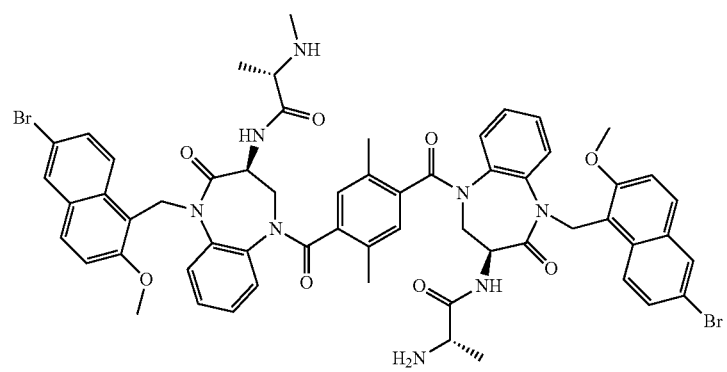 | 1181 (M + H) |

TABLE 3-continued
| Example | Dicarbonyl Chloride | Product | MS (m/z) |
|---|---|---|---|
| Ex 14 | 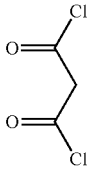 | 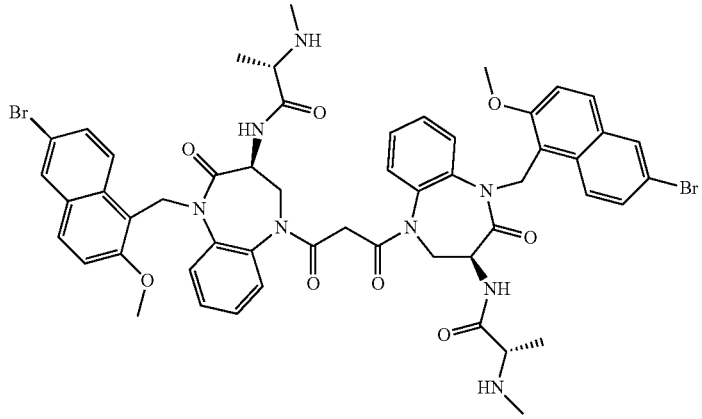 [SMILES: CN[C@@H](C)C(=O)N[C@H]1CN(C(=O)CC(=O)N2C[C@H](NC(=O)[C@H](C)NC)C(=O)N(Cc3c(OC)ccc4cc(Br)ccc34)c3ccccc32)c2ccccc2N(Cc2c(OC)ccc3cc(Br)ccc23)C1=O] | 1091 (M + H) |
| Ex 15 | 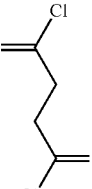 | 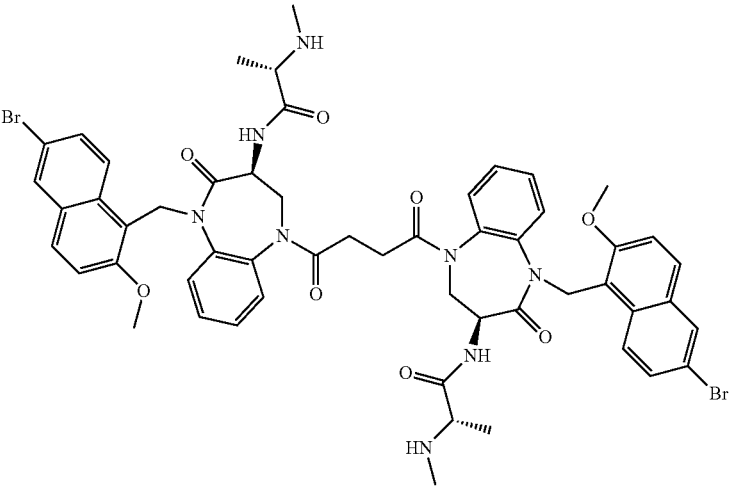 [SMILES: CN[C@@H](C)C(=O)N[C@H]1CN(C(=O)CCC(=O)N2C[C@H](NC(=O)[C@H](C)NC)C(=O)N(Cc3c(OC)ccc4cc(Br)ccc34)c3ccccc32)c2ccccc2N(Cc2c(OC)ccc3cc(Br)ccc23)C1=O] | 1105 (M + H) |
| Ex 16 |  | 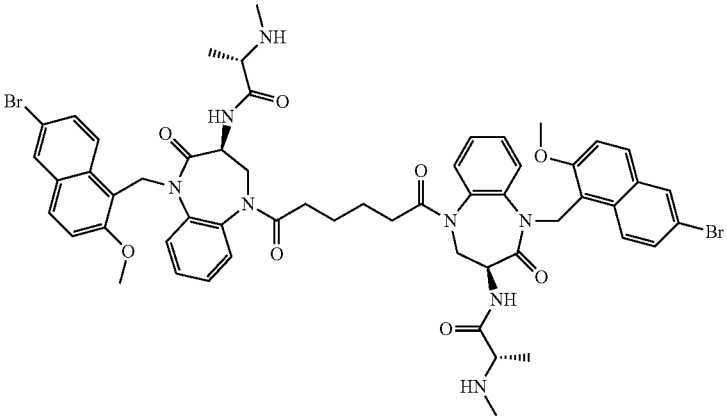 [SMILES: CN[C@@H](C)C(=O)N[C@H]1CN(C(=O)CCCCC(=O)N2C[C@H](NC(=O)[C@H](C)NC)C(=O)N(Cc3c(OC)ccc4cc(Br)ccc34)c3ccccc32)c2ccccc2N(Cc2c(OC)ccc3cc(Br)ccc23)C1=O] | 1134 (M + 2H) |

TABLE 3-continued
| Example | Dicarbonyl Chloride | Product | MS (m/z) |
|---|---|---|---|
| Ex 17 | 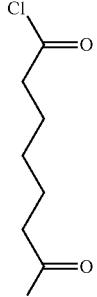 | 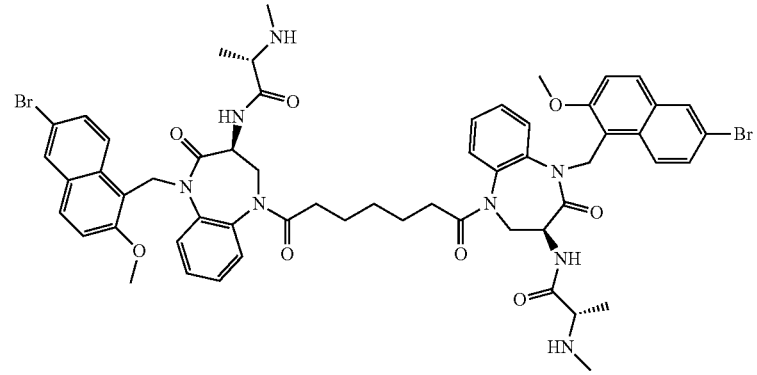 [SMILES: CN[C@@H](C)C(=O)N[C@H]1CN(C(=O)CCCCCC(=O)N2C[C@H](NC(=O)[C@H](C)NC)C(=O)N(Cc3c(OC)ccc4cc(Br)ccc34)c3ccccc32)c2ccccc2N(Cc2c(OC)ccc3cc(Br)ccc23)C1=O] | 1147 (M + H) |
| Ex 18 | 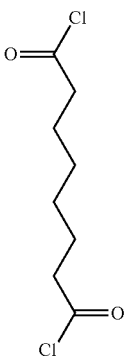 [SMILES: O=C(Cl)CCCCCCC(=O)Cl] | 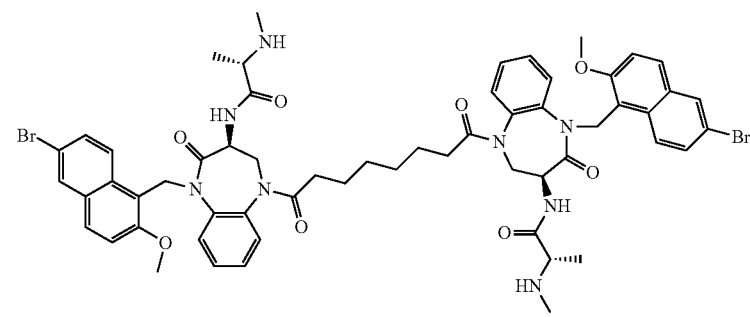 [SMILES: CN[C@@H](C)C(=O)N[C@H]1CN(C(=O)CCCCCCC(=O)N2C[C@H](NC(=O)[C@H](C)NC)C(=O)N(Cc3c(OC)ccc4cc(Br)ccc34)c3ccccc32)c2ccccc2N(Cc2c(OC)ccc3cc(Br)ccc23)C1=O] | 1161 (M + H) |
Example 19
(2S)-N-[(3S)-5-[(6-bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]-2-(methylamino)propanamide dihydrochloride
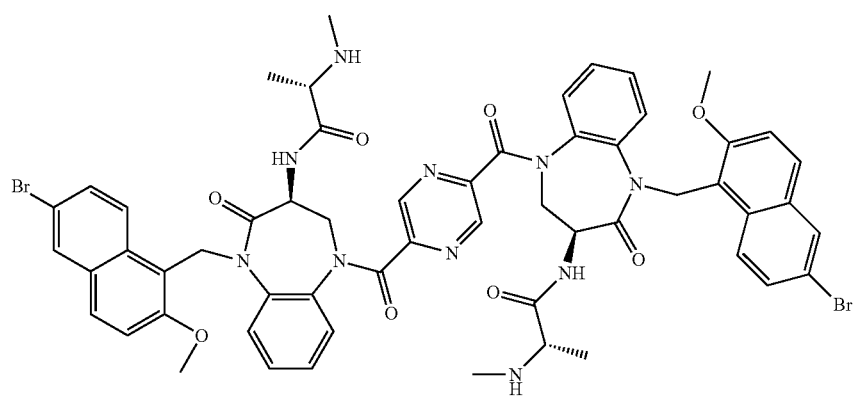 [SMILES: CN[C@@H](C)C(=O)N[C@H]1CN(C(=O)c2cnc(C(=O)N3C[C@H](NC(=O)[C@H](C)NC)C(=O)N(Cc4c(OC)ccc5cc(Br)ccc45)c4ccccc43)cn2)c2ccccc2N(Cc2c(OC)ccc3cc(Br)ccc23)C1=O]

Step 1: To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 11) (300 mg, 0.49 mmol) and pyrazine-2,5-dicarboxylic acid (41.2 mg, 0.24 mmol) in pyridine (5 mL) at 0° C. was added POCl₃ (46 μL, 0.49 mmol) and the cooling bath removed. After 5 h, the mixture was diluted with dichloromethane, washed with water, dried (Na₂SO₄) and concentrated. The residue was purified by preparative reverse phase HPLC to afford tert-butyl N-[(1S)-2-[[(3S)-5-[(6-bromo-2-methoxy-1-naphthyl)methyl]-1-[5-[(3S)-5-[(6-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]amino]-1-methyl-2-oxo-ethyl]-N-methyl-carbamate (52 mg, 7.82%) as an off white solid. LC-MS: 1355.0 (M+H).

Step 2: In a similar manner to that described for Example 6, Step 2, tert-butyl N-[(1S)-2-[[(3S)-5-[(6-bromo-2-methoxy-1-naphthyl)methyl]-1-[5-[(3S)-5-[(6-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]amino]-1-methyl-2-oxo-ethyl]-N-methyl-carbamate (50 mg, 0.04 mmol) was converted to the title compound (32 mg, 71%) obtained as a white solid. LC-MS: 1155.6 (M+H).

Example 20

(2S)-N-[(3S)-5-[(6-bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide dihydrochloride

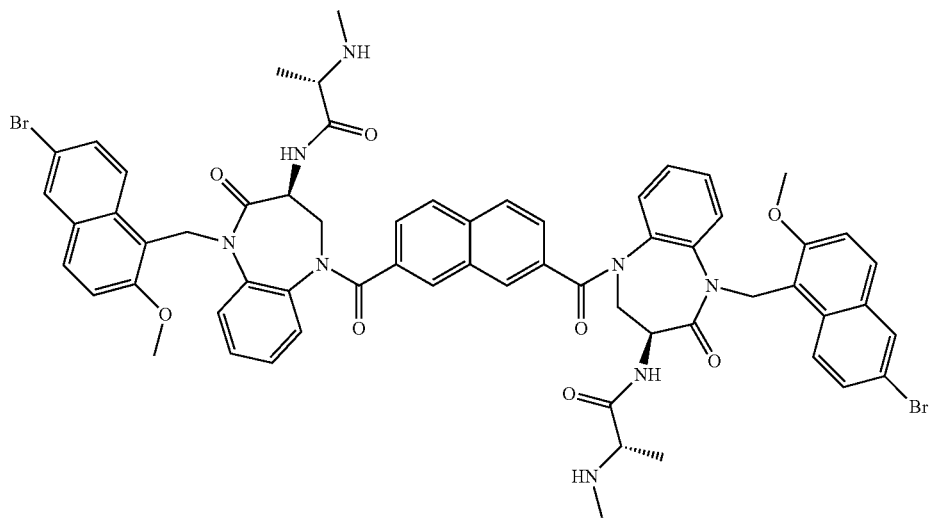 [SMILES: CN[C@@H](C)C(=O)N[C@H]1CN(C(=O)c2ccc3ccc(C(=O)N4C[C@H](NC(=O)[C@H](C)NC)C(=O)N(Cc5c(OC)ccc6cc(Br)ccc56)c5ccccc54)cc3c2)c2ccccc2N(Cc2c(OC)ccc3cc(Br)ccc23)C1=O]

In a similar manner to that described for Example 19, {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 11) (300 mg, 0.49 mmol) and naphthalene-2,7-dicarboxylic acid (54 mg, 0.24 mmol) were converted to the title compound (31 mg) obtained as an off white solid. LC-MS: 1203.6 (M+H).

Example 21

(2S)-N-[(3S)-5-[(6-bromo-2-methoxy-1-naphthyl)methyl]-1-[2-[3-[2-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-2-oxo-ethyl]phenyl]acetyl]-4-oxo-2,3-dihydro-1,5-benzodiazepin-3-yl]-2-(methylamino)propanamide dihydrochloride

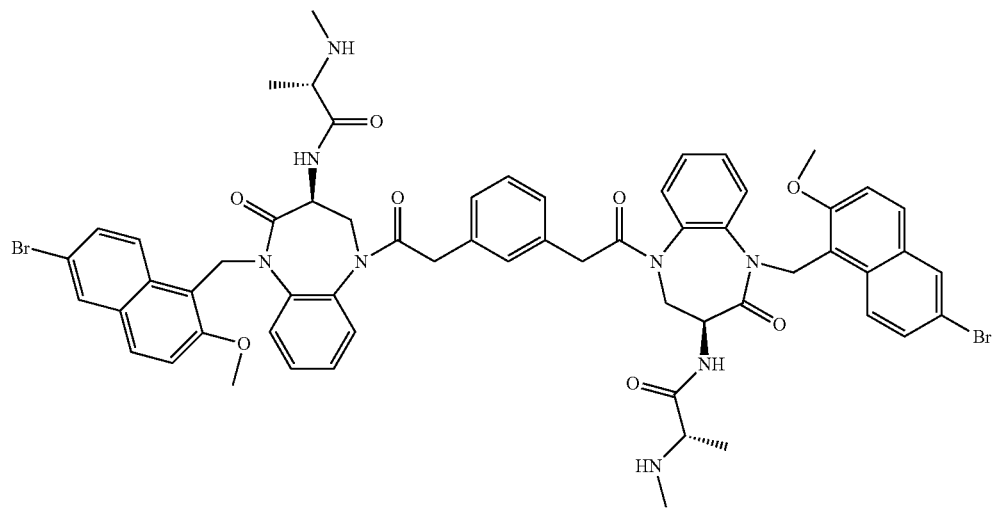 [SMILES: CN[C@@H](C)C(=O)N[C@H]1CN(C(=O)Cc2cccc(CC(=O)N3C[C@H](NC(=O)[C@H](C)NC)C(=O)N(Cc4c(OC)ccc5cc(Br)ccc45)c4ccccc43)c2)c2ccccc2N(Cc2c(OC)ccc3cc(Br)ccc23)C1=O]

In a similar manner to that described for Example 19, {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 11) (300 mg, 0.49 mmol) and (3-carboxymethyl-phenyl)-acetic acid (47.62 mg, 0.24 mmol) were converted to the title compound (86 mg) obtained as an off white solid. LC-MS: 1381.2 (M+H).

Example 22

(2S)-N-[(3S)-5-[(5-Bromo-2-methoxy-1-naphthyl)methyl]-1-[4-[(3S)-5-[(5-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide dihydrochloride

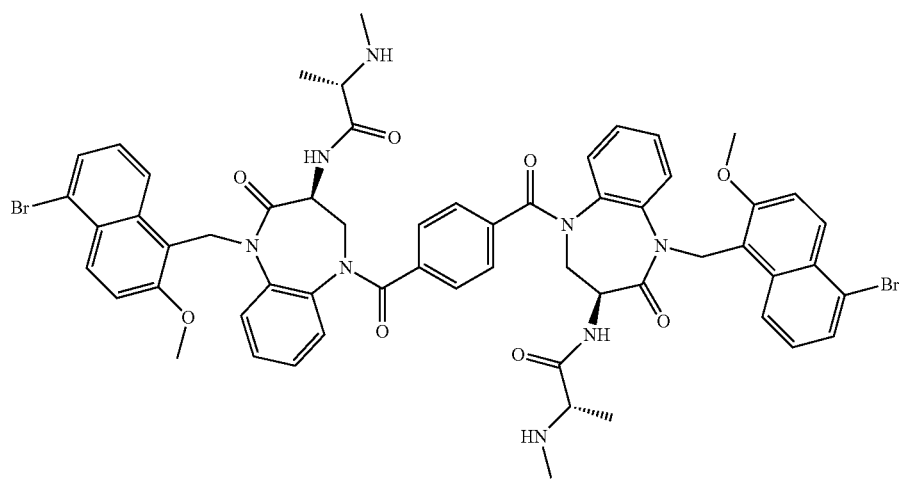 [SMILES: CN[C@@H](C)C(=O)N[C@H]1CN(C(=O)c2ccc(C(=O)N3C[C@H](NC(=O)[C@H](C)NC)C(=O)N(Cc4c(OC)ccc5c(Br)cccc45)c4ccccc43)cc2)c2ccccc2N(Cc2c(OC)ccc3c(Br)cccc23)C1=O]

Step 1: To a stirred solution terephthaloyl chloride (124.591 mg, 0.614 mmol) in dry THF (5 mL) was added triethylamine (0.428 mL, 3.069 mmol) and {(S)-1-[(S)-1-(5-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 12)(750 mg, 1.227 mmol). After 18 h, the mixture was evaporated and the residue purified by silica gel chromatography to afford tert-butyl N-[(1S)-2-[[(3S)-5-[(5-bromo-2-methoxy-1-naphthyl)methyl]-1-[4-[(3S)-5-[(5-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]benzoyl]-4-oxo-2,3-dihydro-1,5-benzodiazepin-3-yl]amino]-1-methyl-2-oxo-ethyl]-N-methyl-carbamate (170 mg, 20.47%) as white solid.

Step 2: To a solution of tert-butyl N-[(1S)-2-[[(3S)-5-[(5-bromo-2-methoxy-1-naphthyl)methyl]-1-[4-[(3S)-5-[(5-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]benzoyl]-4-oxo-2,3-dihydro-1,5-benzodiazepin-3-yl]amino]-1-methyl-2-oxo-ethyl]-N-methyl-carbamate (50 mg, 0.037 mmol) in dioxane (1 mL) at 0° C. was added 4 M HCl in dioxane (0.6 mL) dropwise and the cooling bath removed. After 3 h the mixture was evaporated and the residue was triturated with hexane to afford the title compound (35 mg, 77.2%) as a white solid. LC-MS: 1153.2 (M+H).

Example 23

(2S)-2-(Methylamino)-N-[(3S)-1-[4-[(3S)-3-[[(2S)-2-(methylamino)propanoyl]amino]-5-[(2-methyl-1-naphthyl)methyl]-4-oxo-2,3-dihydro-1,5-benzodiazepine-1-carbonyl]benzoyl]-5-[(2-methyl-1-naphthyl)methyl]-4-oxo-2,3-dihydro-1,5-benzodiazepin-3-yl]propanamide dihydrochloride

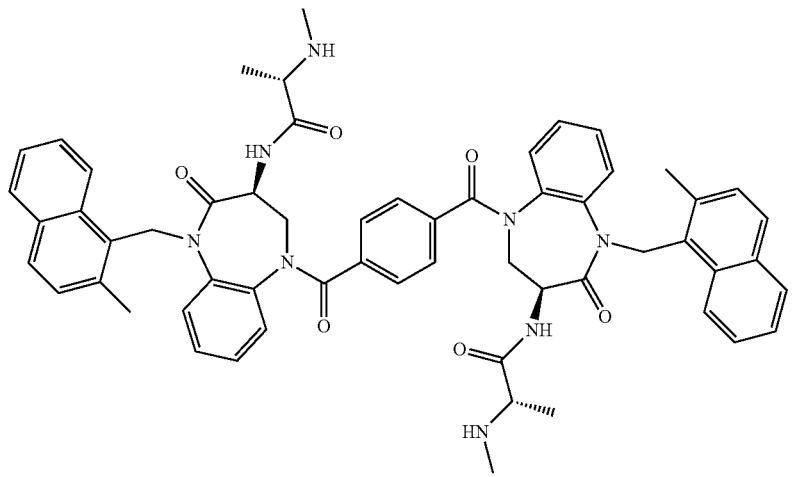 [SMILES: CN[C@@H](C)C(=O)N[C@H]1CN(C(=O)c2ccc(C(=O)N3C[C@H](NC(=O)[C@H](C)NC)C(=O)N(Cc4c(C)ccc5ccccc45)c4ccccc43)cc2)c2ccccc2N(Cc2c(C)ccc3ccccc23)C1=O]

In a similar manner to that described for Example 22, terephthaloyl chloride (60 mg, 0.296 mmol) and methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (Intermediate 15) (305.37 mg, 0.591 mmol) were converted to the title compound (50 mg) as an off white solid. LC-MS: 963.6 (M+H).

Example 24

(2S)-N-[(3S)-5-[[1-(2-Cyanophenyl)indazol-3-yl]methyl]-1-[4-[(3S)-5-[[1-(2-cyanophenyl)indazol-3-yl]methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide dihydrochloride

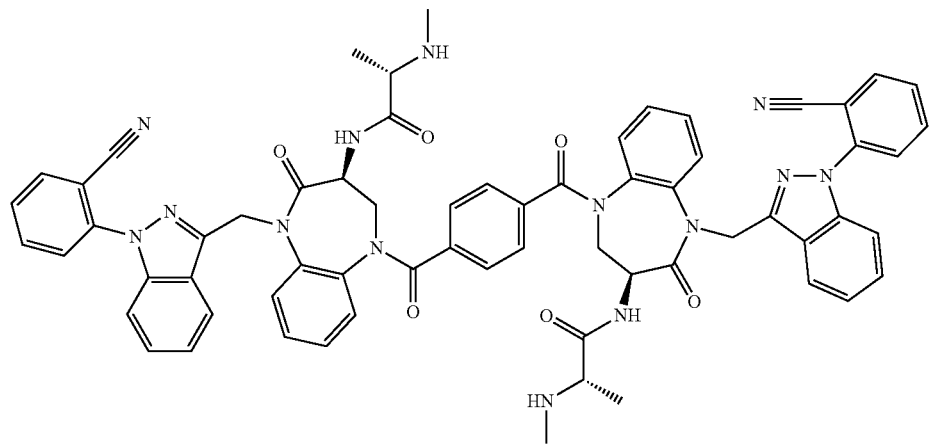 [SMILES: CN[C@@H](C)C(=O)N[C@H]1CN(C(=O)c2ccc(C(=O)N3C[C@H](NC(=O)[C@H](C)NC)C(=O)N(Cc4nn(-c5ccccc5C#N)c5ccccc45)c4ccccc43)cc2)c2ccccc2N(Cc2nn(-c3ccccc3C#N)c3ccccc23)C1=O]

In a similar manner to that described for Example 22, ((S)-1-{(S)-1-[1-(2-cyano-phenyl)-1H-indazol-3-ylmethyl]-2-oxo-2,3,4,5-tetrahydro-1H-benzo[b][1,4]diazepin-3-ylcarbamoyl}-ethyl)-methyl-carbamic acid tert-butyl ester (Intermediate 14) (262.9 mg, 0.443 mmol) and terephthaloyl chloride (45 mg, 0.222 mmol) were converted to the title compound (13 mg) as a white solid. LC-MS: 1118 (M+H).

Example 25

(2S)-N-[(3S)-5-[(2-Methoxy-1-naphthyl)methyl]-1-[4-[(3S)-5-[(2-methoxy-1-naphthyl)methyl]-3-[[(2S)-2-(methylamino) propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide dihydrochloride

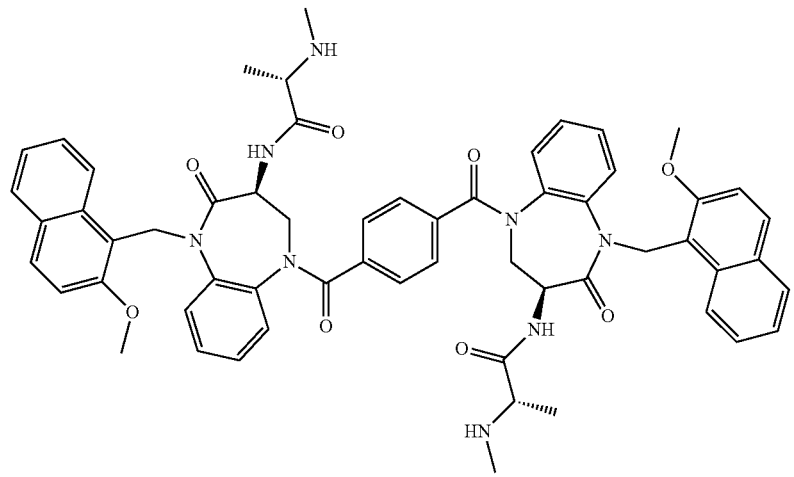 [SMILES: CN[C@@H](C)C(=O)N[C@H]1CN(C(=O)c2ccc(C(=O)N3C[C@H](NC(=O)[C@H](C)NC)C(=O)N(Cc4c(OC)ccc5ccccc45)c4ccccc43)cc2)c2ccccc2N(Cc2c(OC)ccc3ccccc23)C1=O]

Step 1: To a stirred solution {(S)-1-[(S)-1-(2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (51.89 mg, 0.098 mmol) in dry THF (4 mL) was added cesium carbonate (65 mg, 0.2 mmol). After 2 h, terephthaloyl chloride (9 mg, 0.044 mmol) 1.227 mmol) was added and the mixture stirred for 18 h. The mixture was evaporated and the residue was purified by silica gel chromatography to afford tert-butyl N-[(1S)-2-[[(3S)-1-[4-[(3S)-3-[[(2S)-2-[tert-butoxycarbonynyl(methy)amino]propanoyl]amino]-5-[2-methoxy-1-naphthyl)methyl]-4-oxo-2,3-dihydro-1,5-benzodiazepine-1-carbonyl]benzoyl]-5-[(2-methoxy-(2-methoxy-1-naphthyl)methyl]-4-oxo-2,3-dihydro-1,5-benzodiazepin-3-yl]amino]-1-methyl-2-oxo-ethyl]-N-methyl-carbamate (45 mg, 84.9%) as a white solid. LC-MS: 1195.8 (M+H).

Step 2: In a similar manner to that described for Example 6, Step 2, tert-butyl N-[(1S)-2-[[(3)-1-[4-[(3S)-3-[[(2S)-2-[tert-butoxycarbonyl(methyl)amino]propanoyl]amino]-5-[(2-methoxy-1-naphthyl)methyl]-4-oxo-2,3-dihydro-1,5-benzodiazepine-1-carbonyl]benzoyl]-5-[(2-methoxy-1-naphthyl)methyl]-4-oxo-2,3-dihydro-1,5-benzodiazepin-3-yl]amino]-1-methyl-2-oxo-ethyl]-N-methyl-carbamate (40 mg, 0.33 mmol) was converted to the title compound (30 mg, 84%) as a white solid. LC-MS: 996 (M+H).

Example 26

(2S)-N-[(3S)-7-Cyano-5-[4-[(3S)-7-cyano-3-[[(2S)-2-(methylamino)propanoyl]amino]-1-[(2-methyl-1-naphthyl)methyl]-2-oxo-3,4-dihydro-1,5-benzodiazepine-5-carbonyl]benzoyl]-1-[(2-methyl-1-naphthyl)methyl]-2-oxo-3,4-dihydro-1,5-benzodiazepin-3-yl]-2-(methylamino)propanamide dihydrochloride Step 1: To a solution of {(S)-1-[(S)-7-cyano-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (Intermediate 16) (90 mg, 0.166 mmol) in pyridine (1 mL) was added terephthalic acid (13.808 mg, 0.083 mmol). After 10 min the mixture was cooled to 0° C., POCl₃ (0.017 mL, 0.183 mmol) was added and the cooling bath was removed. After 1 h, the mixture was concentrated, the residue was dissolved in ethyl acetate and the mixture was washed with water, NaHCO₃ solution, and brine, dried over sodium sulfate and concentrated. The residue was purified by preparative reverse phase HPLC to provide tert-butyl N-[(1S)-2-[[(3S)-5-[4-[(3S)-3-[[(2S)-2-[tert-butoxycarbonyl(methyl)amino]propanoyl]amino]-7-cyano-1-[(2-methyl-1-naphthyl)methyl]-2-oxo-3,4-dihydro-1,5-benzodiazepine-5-carbonyl]benzoyl]-7-cyano-1-[(2-methyl-1-naphthyl)methyl]-2-oxo-3,4-dihydro-1,5-benzodiazepin-3-yl]amino]-1-methyl-2-oxo-ethyl]-N-methyl-carbamate as white solid (5 mg, 5.32%). LC-MS: 1213.6 (M+H).

Step 2: To a solution of tert-butyl N-[(1S)-2-[[(3S)-5-[4-[(3S)-3-[[(2S)-2-[tert-butoxycarbonyl(methyl)amino]propanoyl]amino]-7-cyano-1-[(2-methyl-1-naphthyl)methyl]-2-oxo-3,4-dihydro-1,5-benzodiazepine-5-carbonyl]benzoyl]-7-cyano-1-[(2-methyl-1-naphthyl)methyl]-2-oxo-3,4-dihydro-1,5-benzodiazepin-3-yl]amino]-1-methyl-2-oxo-ethyl]-N-methyl-carbamate (27 mg, 0.022 mmol) in dioxane (3 mL) at 0° C. was added 4 M HCl in dioxane (2 mL). The mixture was stirred at 0° C. for 10 min, and the cooling bath was removed. After 16 h, the mixture was concentrated and the residue was triturated with diethyl ether to afford the title compound as a white solid (19 mg, 78.69%). LC-MS: 1013.8 (M+H).

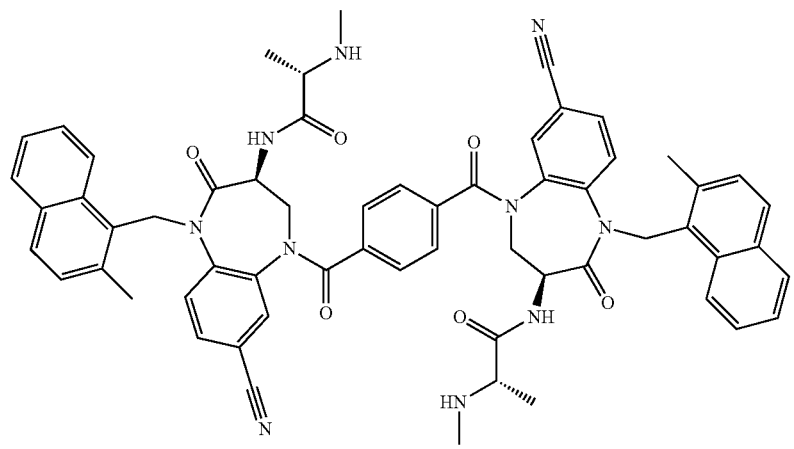 [SMILES: CN[C@@H](C)C(=O)N[C@H]1CN(C(=O)c2ccc(C(=O)N3C[C@H](NC(=O)[C@H](C)NC)C(=O)N(Cc4c(C)ccc5ccccc45)c4ccc(C#N)cc43)cc2)c2cc(C#N)ccc2N(Cc2c(C)ccc3ccccc23)C1=O]

Example 27

(2S)-N-[(3S)-1-[(6-Bromo-2-methoxy-1-naphthyl)methyl]-5-[4-[(3S)-1-[(6-bromo-2-methoxy-1-naphthyl)methyl]-7-cyano-3-[[(2S)-2-(methylamino)propanoyl]amino]-2-oxo-3,4-dihydro-1,5-benzodiazepine-5-carbonyl]benzoyl]-7-cyano-2-oxo-3,4-dihydro-1,5-benzodiazepin-3-yl]-2-(methylamino)propanamide dihydrochloride

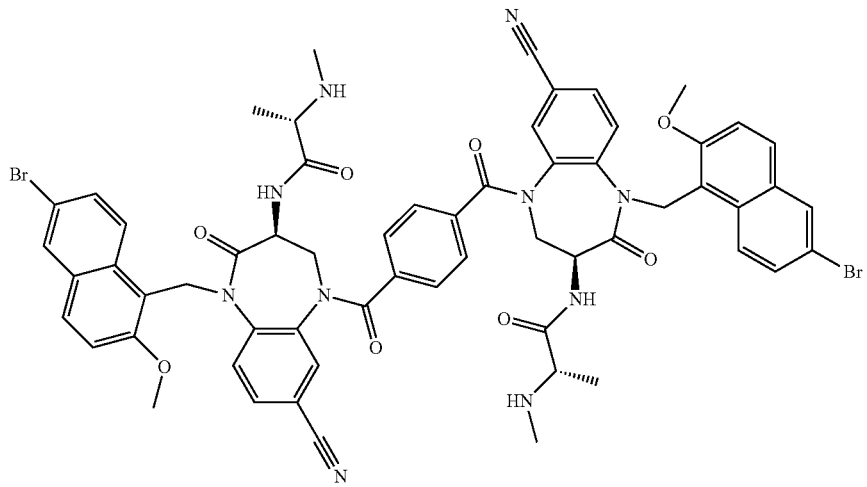 [SMILES: CN[C@@H](C)C(=O)N[C@H]1CN(C(=O)c2ccc(C(=O)N3C[C@H](NC(=O)[C@H](C)NC)C(=O)N(Cc4c(OC)ccc5cc(Br)ccc45)c4ccc(C#N)cc43)cc2)c2cc(C#N)ccc2N(Cc2c(OC)ccc3cc(Br)ccc23)C1=O]

Step 1: To a solution of {(S)-1-[(S)-1-(6-bromo-2-methoxy-naphthalen-1-ylmethyl)-7-cyano-2-oxo-2,3,4,5-tetrahydro-1H-benzo[b][1,4]diazepin-3-ylcarbamoyl]-ethyl}-methyl-carbamic acid tert-butyl ester (Intermediate 4) (120 mg, 0.189 mmol) in pyridine (2 mL) was added terephthalic acid (20.604 mg, 0.113 mmol). After 10 min, the mixture was cooled to 0° C., POCl$_3$ (0.036 mL, 0.396 mmol) was added and the cooling bath was removed. After 1 h, the mixture was concentrated, the residue was diluted with ethyl acetate and filtered. The filtrate was concentrated and the residue was purified by preparative HPLC to provide tert-butyl N-[(1S)-2-[[(3S)-1-[(6-bromo-2-methoxy-1-naphthyl)methyl]-5-[4-[(3S)-1-[(6-bromo-2-methoxy-1-naphthyl)methyl]-3-[[(2S)-2-[tert-butoxycarbonyl(methyl)amino]propanoyl]amino]-7-cyano-2-oxo-3,4-dihydro-1,5-benzodiazepine-5-carbonyl]benzoyl]-7-cyano-2-oxo-3,4-dihydro-1,5-benzodiazepin-3-yl]amino]-1-methyl-2-oxo-ethyl]-N-methyl-carbamate (6 mg, 1%) as an off white solid. LC-MS: 1403.2 (M+H).

Step 2: In a similar manner to that described for Example 26, Step 2, tert-butyl N-[(1S)-2-[[(3S)-1-[(6-bromo-2-methoxy-1-naphthyl)methyl]-5-[4-[(3S)-1-[(6-bromo-2-methoxy-1-naphthyl)methyl]-3-[[(2S)-2-[tert-butoxycarbonyl(methyl)amino]propanoyl]amino]-7-cyano-2-oxo-3,4-dihydro-1,5-benzodiazepine-5-carbonyl]benzoyl]-7-cyano-2-oxo-3,4-dihydro-1,5-benzodiazepin-3-yl]amino]-1-methyl-2-oxo-ethyl]-N-methyl-carbamate (6 mg, 0.0042 mmol) was converted to the title compound (4.5 mg, 76.6%) as a white solid. LC-MS: 1203.2 (M+H).

Example 28

(2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide dihydrochloride

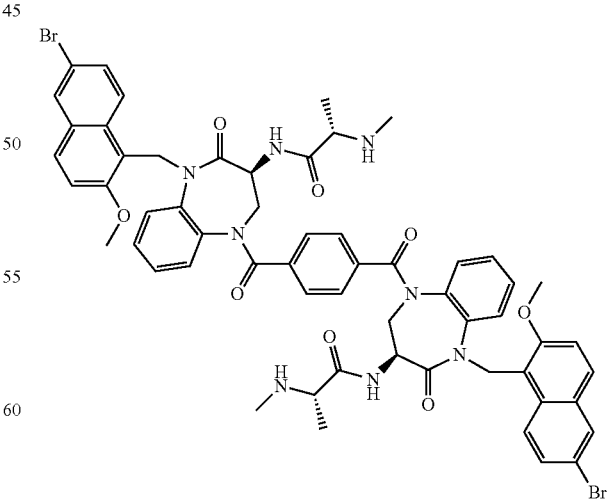

Step 1: To ((S)-2-oxo-2,3,4,5-tetrahydro-1H-benzo[b][1,4]diazepin-3-yl)-carbamic acid tert-butyl ester (Intermediate 2) (57.9 mg, 0.209 mmol) and triethylamine (29.1 μL, 0.209 mmol) in anhydrous THF (1 mL) was added terephthaloyl dichloride (21.2 mg, 0.104 mmol). The resulting suspension was stirred at room temperature for 4 h. The mixture was concentrated and the residue was triturated with water. The solid was collected, washed with water and purified by silica gel chromatography to provide tert-butyl N-[(3S)-5-[4-[(3S)-3-(tert-butoxycarbonylamino)-2-oxo-3,4-dihydro-1H-1,5-benzodiazepine-5-carbonyl]benzoyl]-2-oxo-3,4-dihydro-1H-1,5-benzodiazepin-3-yl]carbamate as a white solid (27.6 mg, 39%).

Step 2: tert-Butyl N-[(3S)-5-[4-[(3S)-3-(tert-butoxycarbonylamino)-2-oxo-3,4-dihydro-1H-1,5-benzodiazepine-5-carbonyl]benzoyl]-2-oxo-3,4-dihydro-1H-1,5-benzodiazepin-3-yl]carbamate (27.6 mg, 0.0403 mmol), 6-bromo-1-(chloromethyl)-2-methoxynaphthalene (25.3 mg, 0.0887 mmol), and cesium carbonate (39.4 mg, 0.121 mmol) where combined in DMF (2 mL) and stirred at room temperature for 16 h. The mixture was diluted with ethyl acetate, washed with water, brine and dried over anhydrous magnesium sulfate. Concentration gave an oil that was chromatographed over silica gel to give tert-butyl N-[(3S)-5-[(6-bromo-2-methoxy-1-naphthyl)methyl]-1-[4-[(3S)-5-[(6-bromo-2-methoxy-1-naphthyl)methyl]-3-(tert-butoxycarbonylamino)-4-oxo-2,3-dihydro-1,5-benzodiazepine-1-carbonyl]benzoyl]-4-oxo-2,3-dihydro-1,5-benzodiazepin-3-yl]carbamate (31 mg, 65%) as a white foam.

Step 3: tert-Butyl N-[(3S)-5-[(6-bromo-2-methoxy-1-naphthyl)methyl]-1-[4-[(3S)-5-[(6-bromo-2-methoxy-1-naphthyl)methyl]-3-(tert-butoxycarbonylamino)-4-oxo-2,3-dihydro-1,5-benzodiazepine-1-carbonyl]benzoyl]-4-oxo-2,3-dihydro-1,5-benzodiazepin-3-yl]carbamate (31 mg, 0.026 mmol) and acetyl chloride (9.3 μL, 0.131 mmol) were combined in MeOH (2 mL) and stirred at room temperature for 16 h. The mixture was concentrated to give (3S)-3-amino-1-[4-[(3S)-3-amino-5-[(6-bromo-2-methoxy-1-naphthyl)methyl]-4-oxo-2,3-dihydro-1,5-benzodiazepine-1-carbonyl]benzoyl]-5-[(6-bromo-2-methoxy-1-naphthyl)methyl]-2,3-dihydro-1,5-benzodiazepin-4-one dihydrochloride as a white solid (27 mg, 98%) that was used without further purification.

Step 4: (3S)-3-Amino-1-[4-[(3S)-3-amino-5-[(6-bromo-2-methoxy-1-naphthyl)methyl]-4-oxo-2,3-dihydro-1,5-benzodiazepine-1-carbonyl]benzoyl]-5-[(6-bromo-2-methoxy-1-naphthyl)methyl]-2,3-dihydro-1,5-benzodiazepin-4-one dihydrochloride (27 mg, 0.026 mmol), Boc-N-Me-Ala-OH (10.9 mg, 0.0537 mmol), N,N-diisopropylethylamine (44.7 μL, 0.256 mmol), and HATU (20.4 mg, 0.0537 mmol) were combined in CH$_2$Cl$_2$ (2 mL) and stirred at room temperature for 5 days. The mixture was partitioned between saturated ammonium chloride solution and dichloromethane. The organic layer was separated and washed with water, saturated sodium bicarbonate solution, brine and dried over anhydrous magnesium sulfate. Concentration gave an oil that was chromatographed over silica gel to give tert-butyl N-[(1S)-2-[[(3S)-5-[(6-bromo-2-methoxy-1-naphthyl)methyl]-1-[4-[(3S)-5-[(6-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]benzoyl]-4-oxo-2,3-dihydro-1,5-benzodiazepin-3-yl]amino]-1-methyl-2-oxo-ethyl]-N-methyl-carbamate (24.5 mg, 71%) as an oil.

Step 5: tert-Butyl N-[(1S)-2-[[(3S)-5-[(6-bromo-2-methoxy-1-naphthyl)methyl]-1-[4-[(3S)-5-[(6-bromo-2-methoxy-1-naphthyl)methyl]-3-[[(2S)-2-[tert-butoxycarbonyl(methyl)amino]propanoyl]amino]-4-oxo-2,3-dihydro-1,5-benzodiazepine-1-carbonyl]benzoyl]-4-oxo-2,3-dihydro-1,5-benzodiazepin-3-yl]amino]-1-methyl-2-oxo-ethyl]-N-methyl-carbamate (24 mg, 0.018 mmol) and acetyl chloride (6.3 μL, 0.089 mmol) were combined in MeOH (2 mL) and stirred at room temperature overnight. The mixture was concentrated and the residue triturated with acetonitrile to give the title compound (18.3 mg, 84%) as a solid. LC-MS: 1149 [M−H].

Example 29

Biochemical Assays
TR-FRET Assay for BIR2 and BIR3
The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(ε-biotin)-OH 1:2 TFA ("Peptide A") was identified as a substrate for the TR-FRET assay by screening the 6× Histidine-tagged BIR2 domain and BIR3 domain of XIAP against a set of 29 peptides synthesized based on sequences reported by Sweeny et al. (*Biochemistry*, 2006, 45, 14740 14748). The peptides were labeled with the fluorescent tags FITC or TAMRA and Kd values were determined by fluorescence polarization assay. The sequence AVPIAQKSEK was identified as optimal for using in an assay. The peptide sequence was derivatized with biotin to provide AVPIAQKSEK-(ε-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is MRHHHHHH-HRDHFALDRPSETHADYLLRTGQVVDISDTIYPRNPA-MYSEEARLKSFQNWPDYAHLTPRELASAGLYYTGIG-DQVQCFACGGKLKNWEPGDRAWSEHRRHFPNCFFV-LGRNLNIRSE.

The sequence of the BIR3 domain used for the TR-FRET assay is MRHHHHHHRSDAVS SDRNFPNSTNLPRNPS-MADYEARIFTFGTWIYSVNKEQLARAGFYALGEGD-KVKCFHCGGGLTDWKPSEDPWEQHAKWYPGCKYL-LEQKGQEYINNIHLTHSLEECLVRTT.

Ten nanomolar of 6× Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(ε-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an IC$_{50}$ value for each test compound.

These values are listed below in Table 4.

TABLE 4

| Example | Compound Name | BIR2 Ic50 (μM) | BIR3 Ic50 (μM) |
|---|---|---|---|
| Ex 28 | (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino-4-oxo-2,3-dihydro-1,5-benzodiazepine-1-carbonyl]benzoyl]-4-oxo-2,3-dihydro-1,5-benzodiazepin-3-yl]-2-(methylamino)propanamide | 0.000289 | 1.9065 |
| Ex 2 | (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1R)-tetralin-1-yl]pyrrolidine-2-carboxamide | 0.00311 | 0.00733 |
| Ex 1 | (2S,4S)-N-Benzyl-4-[[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]pyrrolidine-2-carboxamide | 0.00125 | 0.0272 |
| Ex 3 | (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1S)-tetralin-1-yl]pyrrolidine-2-carboxamide | 0.001705 | 0.063533333 |
| Ex 23 | (2S)-2-(Methylamino)-N-[(3S)-1-[4-[(3S)-3-[[(2S)-2-(methylamino)propanoyl]amino] -5-[(2-methyl-1-naphthyl)methyl]-4-oxo-2,3-dihydro-1,5-benzodiazepine-1-carbonyl]benzoyl]-5-[(2-methyl-l-naphthyl)methyl]-4-oxo-2,3-dihydro-1,5-benzodiazepin-3-yl]propanamide | 0.000429 | 10.28 |
| Ex 22 | (2S)-N-[(3S)-5-[(5-Bromo-2-methoxy-1-naphthyl)methyl]-1-[4-[(3S)-5-[(5-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide | 0.00032 | 34.66 |
| Ex 9 | (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide | <5.1E−5 | 1.15 |
| Ex 4 | (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-N-cyclohexyl-1-[(2S)-2-cyclohexyl-2-[[(2S)-2-(methylamino)propanoyl]amino]acetyl]pyrrolidine-2-carboxamide | 0.004585 | 0.471 |
| Ex 5 | (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-isopropyl-pyrrolidine-2-carboxamide | 0.00298 | 0.495 |
| Ex 15 | (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-4-oxo-butanoyl]-4-oxo-2,3-dihydro-1,5-benzodiazepin-3-yl]-2-(methylamino)propanamide | 0.00102 | 8.107 |
| Ex 16 | (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-6-oxo-hexanoyl]-4-oxo-2,3-dihydro-1,5-benzodiazepin-3-yl]-2-(methylamino)propanamide | 0.000375 | 5.959 |

TABLE 4-continued

| Example | Compound Name | BIR2 Ic50 (μM) | BIR3 Ic50 (μM) |
|---|---|---|---|
| Ex 24 | (2S)-N-[(3S)-5-[[1-(2-Cyanophenyl)indazol-3-yl]methyl]-1-[4-[(3S)-5-[[1-(2-cyanophenyl)indazol-3-yl]methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide | 0.00158 | 17.03 |
| Ex 21 | (2S)-N-[(3S)-5-[(6-Bromo-2-methoxy-1-naphthyL)methyl]-1-[2-[3-[2-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-2-oxo-ethyl]phenyl]acetyl]-4-oxo-2,3-dihydro-1,5-benzodiazepin-3-yl] -2-(methylamino)propanamide | | 0.738 |
| Ex 19 | (2S)-N-[(3S)-5-[(6-Bromo-2-methoxy-1-naphthyl)methyl]-1-[5-[(3S)-5-[(6-bromo-2-methoxy-1-naphthyl)methyl]-3- [[(2S)-2-(methylamino)propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]-2-(methylamino)propanamide | 0.000325 | 0.572 |
| Ex 26 | (2S)-N-[(3S)-7-Cyano-5-[4-[(3S)-7-cyano-3-[[(2S)-2-(methylamino)propanoyl]amino]-1-[(2-methyl-1-naphthyl)methyl]-2-oxo-3,4-dihydro-1,5-benzodiazepine-5-carbonyl]benzoyl]-1-[(2-methyl-1-naphthyl)methyl]-2-oxo-3,4-dihydro-1,5-benzodiazepin-3-yl]-2-(methylamino)propanamide | 0.000815 | 3.178 |
| Ex 14 | (2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-3-oxo-propanoyl]-4-oxo-2,3-dihydro-1,5-benzodiazepin-3-yl]-2-(methylamino)propanamide | 0.00143 | 5.134 |
| Ex 17 | (2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-7-oxo-heptanoyl]-4-oxo-2,3-dihydro-1,5-benzodiazepin-3-yl]-2-(methylamino)propanamide | 0.000307 | 6.652 |
| Ex 7 | (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-2-carbonyl]-4-oxo-2,3-dihydro-1,5-benzodiazepin-3-yl]-2-(methylamino)propanamide | 0.00087 | 11.08 |
| Ex 18 | (2S)-N-[(3S)-5-[(6-Bromo-2-methoxy-1-naphthyl)methyl]-1-[8-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-8-oxo-octanoyl]-4-oxo-2,3-dihydro-1,5-benzodiazepin-3-yl]-2-(methylamino)propanamide | 0.0008715 | >5.48 |
| Ex 20 | (2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide | 0.00123 | 4.976 |
| Ex 11 | (2S)-N-[(3S)-5-[(6-Bromo-2-methoxy-1-naphthyl)methyl]-1-[4-[4-(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]phenoxy]benzoyl]-4-oxo-2,3-dihydro-1,5-benzodiazepin-3-yl]-2-(methylamino)propanamide | 0.0012 | >5.48 |
| Ex 12 | (2S)-N-R3S)-5-[(6-Bromo-2-methoxy-1-naphthyl)methyl]-1-[6-[(3S)-5-[(6-bromo-2-methoxy-1-naphthyl)methyl]-3- [[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl] -2-(methylamino)propanamide | | |

TABLE 4-continued

| Example | Compound Name | BIR2 Ic50 (μM) | BIR3 Ic50 (μM) |
|---|---|---|---|
| Ex 25 | (2S)-N-[(3S)-5-[(2-Methoxy-1-naphthyl)methyl]-1-[4-[(3S)-5-[(2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide | 0.000452 | >5.48 |
| Ex 10 | (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-3-methyl-benzoyl]-4-oxo-2,3-dihydro-1,5-benzodiazepin-3-yl]-2-(methylamino)propanamide | 0.001375 | >5.48 |
| Ex 13 | (2S)-2-Amino-N-[(3S)-5-[(6-bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-2,5-dimethyl-benzoyl]-4-oxo-2,3-dihydro-1,5-benzodiazepin-3-yl]propanamide | 0.000801 | >5.48 |
| Ex 6 | (2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide | 0.0008995 | >5.48 |
| Ex 8 | (2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide | 0.001325 | >5.48 |
| Ex 27 | (2S)-N-[(3S)-1-[(6-Bromo-2-methoxy-1-naphthyl)methyl]-5-[4-[(3S)-1-[(6-bromo-2-methoxy-1-naphthyl)methyl]-7-cyano-3-[[(2S)-2-(methylamino)propanoyl]amino]-2-oxo-3,4-dihydro-1,5-benzodiazepine-5-carbonyl]benzoyl]-7-cyano-2-oxo-3,4-dihydro-1,5-benzodiazepin-3-yl]-2-(methylamino)propanamide | 0.001165 | 4.495 |

The invention claimed is:

1. A compound of Formula I

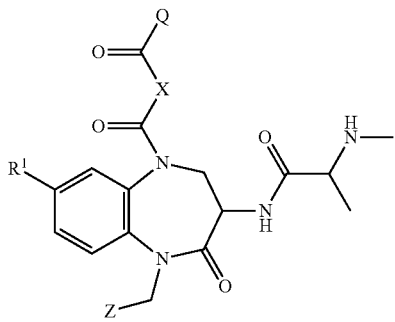

wherein
Z is selected from the group
 a) aryl that optionally is substituted with $OR^3$, halogen and $C_{1-6}$-alkyl, and
 b) heteroaryl that optionally is substituted with aryl that optionally is substituted with cyano;
X is selected from the group
 a) $C_{1-6}$-alkyl,
 b) $C_{1-6}$-alkyl-aryl-$C_{1-6}$-alkyl
 c) aryl that optionally is substituted with $C_{1-6}$-alkyl and -O-aryl, and
 d) heteroaryl;
Q is selected from

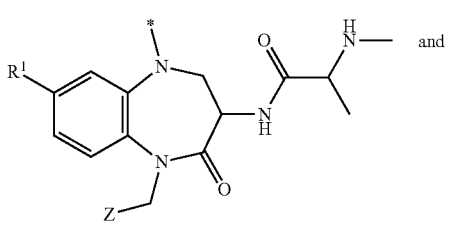

-continued

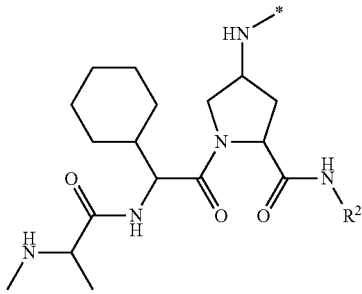

B

R¹ is selected from the group H and cyano;
R² is selected from the group
  a) C$_{1-6}$-alkyl that optionally is substituted with aryl,
  b) C$_{3-7}$-cycloalkyl that optionally is fused with phenyl,
  c) phenyl, and
  d) C$_{3-7}$-cycloalkylaryl; and
R³ is C$_{1-6}$-alkyl;
or a pharmaceutically acceptable salt thereof.

2. The compound of claim 1 wherein
Z is selected from the group
  a) aryl that optionally is substituted with O—C$_{1-6}$-alkyl, halogen and C$_{1-6}$-alkyl, and
  b) heteroaryl that optionally is substituted with cyano-phenyl;
X is selected from the group
  a) C$_{1-6}$-alkyl,
  b) C$_{1-6}$-alkyl-aryl-C$_{1-6}$-alkyl
  c) aryl that optionally is substituted with C$_{1-6}$-alkyl and —O-aryl, and
  d) heteroaryl;
Q is selected from

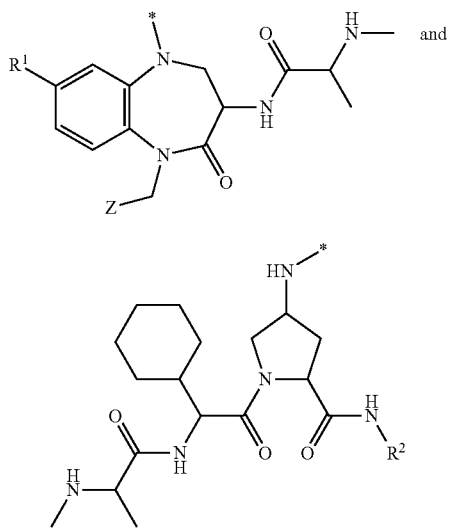

A and

B

R¹ is selected from the group H and cyano;
R² is selected from the group
  a) C$_{1-6}$-alkyl that optionally is substituted with aryl,
  b) C$_{3-7}$-cycloalkyl,
  c) phenyl, and
  d) tetralinyl, and
or a pharmaceutically acceptable salt thereof.

3. The compound of claim 1, wherein Z is aryl that optionally is substituted with O—C$_{1-6}$-alkyl, halogen and C$_{1-6}$-alkyl.

4. The compound of claim 1, wherein Z is naphthyl that optionally is substituted with bromo, methoxy and methyl.

5. The compound of claim 1, wherein Z is 6-bromo-2-methoxy-1-naphthyl.

6. The compound of claim 1, wherein X is C$_{1-6}$-alkyl, heteroaryl, aryl, aryl substituted by C$_{1-6}$-alkyl, C$_{1-6}$-alkyl-phenyl-C$_{1-6}$-alkyl or phenyl-O-phenyl.

7. The compound of claim 1, wherein X is phenyl or naphthyl.

8. The compound of claim 1, wherein X is pyrazinyl or pyridinyl.

9. The compound of claim 1, wherein Q is A.

10. The compound of claim 1, wherein R¹ is H.

11. The compound of claim 1, wherein Q is B.

12. The compound of claim 1, wherein R² is tetralinyl.

13. The compound of claim 1, selected from the group consisting of:
  (2S)-2-(Methylamino)-N-[(3S)-1-[4-[(3S)-3-[[(2S)-2-(methylamino)propanoyl]amino]5-[(2-methyl-1-naphthyl)methyl]-4-oxo-2,3-dihydro-1,5-benzodiazepine-1-carbonyl]benzoyl]-5-[(2-methyl-1-naphthyl)methyl]-4-oxo-2,3-dihydro-1,5-benzodiazepin-3-yl]propanamide,
  (2S)-2-Amino-N-[(3S)-5-[(6-bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-2,5-dimethyl-benzoyl]-4-oxo-2,3-dihydro-1,5-benzodiazepin-3-yl]propanamide,
  (2S)-N-[(3S)-1-[(6-Bromo-2-methoxy-1-naphthyl)methyl]-5-[4-[(3S)-1-[(6-bromo-2-methoxy-1-naphthyl)methyl]-7-cyano-3-[[(2S)-2-(methylamino)propanoyl]amino]-2-oxo-3,4-dihydro-1,5-benzodiazepine-5-carbonyl]benzoyl]-7-cyano-2-oxo-3,4-dihydro-1,5-benzodiazepin-3-yl]-2-(methylamino)propanamide,
  (2S)-N-[(3S)-5-[(2-Methoxy-1-naphthyl)methyl]-1-[4-[(3S)-5-[(2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide,
  (2S)-N-[(3S)-5-[(5-Bromo-2-methoxy-1-naphthyl)methyl]-1-[4-[(3S)-5-[(5-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide,
  (2S)-N-[(3S)-5-[(6-Bromo-2-methoxy-1-naphthyl)methyl]-1-[2-[3-[-2-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-yl]-2-oxo-ethyl]phenyl]acetyl]-4-oxo-2,3-dihydro-1,5-benzodiazepin-3-yl]-2-(methylamino)propanamide,
  (2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]3-oxo-propanoyl]-4-oxo-2,3-dihydro-1,5-benzodiazepin-3-yl]-2-(methylamino)propanamide,
  (2S)-N-[(3S)-5-[(6-Bromo-2-methoxy-1-naphthyl)methyl]-1-[3-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-carbonyl]

benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-4-oxo-butanoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]-3-methyl-benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[4-[4-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]phenoxy]benzoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyrazine-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[5-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-6-oxo-hexanoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[6-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]pyridine-3-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-7-oxo-heptanoyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[7-[(3S)-5-[(6-bromo-2-methoxy-1-naphthyl)methyl]-3-[[(2S)-2-(methylamino)propanoyl]amino]-4-oxo-2,3-dihydro-1,5-benzodiazepine-1-carbonyl]naphthalene-2-carbonyl]-4-oxo-2,3-dihydro-1,5-benzodiazepin-3-yl]-2-(methylamino)propanamide, (2S)-N-[(3S)-5-[(6-Bromo-2-methoxy-1-naphthyl)methyl]-1-[8-[(3S)-5-[(6-bromo-2-methoxy-1-naphthyl)methyl]-3-[[(2S)-2-(methylamino)propanoyl]amino]-4-oxo-2,3-dihydro-1,5-benzodiazepin-1-yl]-8-oxo-octanoyl]-4-oxo-2,3-dihydro-1,5-benzodiazepin-3-yl]-2-(methylamino)propanamide, (2S)-N-[(3S)-5-[[1-(2-Cyanophenyl)indazol-3-yl]methyl]-1-[4-[(3S)-5-[[1-(2-cyanophenyl)indazol-3-yl]methyl]-3-[[(2S)-2-(methylamino)propanoyl]amino]-4-oxo-2,3-dihydro-1,5-benzodiazepine-1-carbonyl]benzoyl]-4-oxo-2,3-dihydro-1,5-benzodiazepin-3-yl]-2-(methylamino)propanamide, (2S)-N-[(3S)-7-Cyano-5-[4-[(3S)-7-cyano-3-[[(2S)-2-(methylamino)propanoyl]amino]-1-[(2-methyl-1-naphthyl)methyl]-2-oxo-3,4-dihydro-1,5-benzodiazepine-5-carbonyl]benzoyl]-1-[(2-methyl-1-naphthyl)methyl]-2-oxo-3,4-dihydro-1,5-benzodiazepin-3-yl]-2-(methylamino)propanamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1R)-tetralin-1-yl]pyrrolidine-2-carboxamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-[(1S)-tetralin-1-yl]pyrrolidine-2-carboxamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-N-cyclohexyl-1-[(2S)-2-cyclohexyl-2-[[(2S)-2-(methylamino)propanoyl]amino]acetyl]pyrrolidine-2-carboxamide, (2S,4S)-4-[[4-[(3S)-5-[(6-Bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]-N-isopropyl-pyrrolidine-2-carboxamide, and (2S,4S)-N-Benzyl-4-[[4-[(3S)-5- [(6-bromo-2-methoxy-1-naphthyl)methyl]-3-[[(2S)-2-(methylamino)propanoyl]amino]-4-oxo-2,3-dihydro-1,5-benzodiazepine-1-carbonyl]benzoyl]amino]-1-[(2S)-2-cyclohexyl-2-[[(2S)-2-(methylamino)propanoyl]amino]acetyl]pyrrolidine-2-carboxamide, or a pharmaceutically acceptable salt thereof.

14. A pharmaceutical composition comprising a therapeutically effective amount of a compound according to claim 1, or a pharmaceutically acceptable salt thereof, as an active ingredient together with a pharmaceutically acceptable carrier or excipient.

* * * * *